US012636711B2

(12) United States Patent
Sweitzer et al.

(10) Patent No.: US 12,636,711 B2
(45) Date of Patent: May 26, 2026

(54) QUICK CONNECT FOR A MEDICAL DEVICE

(71) Applicant: Shukla Medical, St. Petersburg, FL (US)

(72) Inventors: Zachary Robert Sweitzer, Keyport, NJ (US); Nicholas Christopher Keach, Lutz, FL (US)

(73) Assignee: Shukla Medical, St. Petersburg, FL (US)

( * ) Notice: Subject to any disclaimer, the term of this patent is extended or adjusted under 35 U.S.C. 154(b) by 906 days.

(21) Appl. No.: 17/236,746

(22) Filed: Apr. 21, 2021

(65) Prior Publication Data

US 2021/0322081 A1 Oct. 21, 2021

Related U.S. Application Data

(60) Provisional application No. 63/013,123, filed on Apr. 21, 2020.

(51) Int. Cl.
*B23B 31/107* (2006.01)
*A61B 17/00* (2006.01)
(Continued)

(52) U.S. Cl.
CPC .. *B23B 31/107* (2013.01); *A61B 2017/00477* (2013.01); *A61B 17/92* (2013.01);
(Continued)

(58) Field of Classification Search
CPC ... B23B 31/107; B23B 31/16; B23B 31/1078; B23B 2231/58; Y10T 279/17188; Y10T 279/17761; Y10T 279/32; B25B 23/141
See application file for complete search history.

(56) References Cited

U.S. PATENT DOCUMENTS 2,348,380 A * 5/1944 Graham ................. B21D 28/34
                                                   279/905
2,948,173 A * 8/1960 Herrmann ............. B25B 23/141
                                                   464/36
(Continued)

FOREIGN PATENT DOCUMENTS

EP        009061690-0001        6/2022
GB          6193461            1/2022
(Continued)

OTHER PUBLICATIONS

Karcher anti-twist adapter, Karcher, [Post date Unknown], [Site seen May 16, 2023], Seen at URL: https://www.deindeal.ch/en/home-living/karcher/high-pressure-cleaners-and-accessories/karcher-anti-twist-adapter-loosens-loops-in-the-high-pressure%E2%80%A6 (Year: 2023).
(Continued)

*Primary Examiner* — Eric A. Gates
(74) *Attorney, Agent, or Firm* — Kim IP Law Group LLC

(57) ABSTRACT

A quick connect is disclosed for a medical device. The quick connect includes a housing, a slide lock mounted within the housing, and a locking assembly mounted within the housing. The slide lock is for receiving a cooperating connection adapter. The locking assembly includes a substantially annular member having a superiorly facing sloped recess. The substantially annular member is movable along a longitudinal axis of the housing upon rotation of the substantially annular member.

20 Claims, 60 Drawing Sheets

(51) Int. Cl.

| | | |
|---|---|---|
| *A61B 17/92* | (2006.01) | |
| *B23B 31/16* | (2006.01) | |
| *B25D 17/08* | (2006.01) | |

(52) U.S. Cl.

CPC ........... *B23B 31/16* (2013.01); *B23B 2231/58* (2021.01); *B25D 17/088* (2013.01); *Y10T 279/17188* (2015.01); *Y10T 279/17761* (2015.01); *Y10T 279/32* (2015.01)

(56) References Cited

U.S. PATENT DOCUMENTS

| | | | | |
|---|---|---|---|---|
| 3,020,789 A * | 2/1962 | Etzkorn | ................ | B25B 23/141 |
| | | | | 81/474 |
| 4,262,501 A * | 4/1981 | Vaughn | .................... | F16D 7/08 |
| | | | | 464/36 |
| 4,303,357 A * | 12/1981 | Makar | ................... | B23B 31/113 |
| | | | | 408/226 |
| 4,305,597 A * | 12/1981 | McCarty | ............. | B23B 31/1253 |
| | | | | 279/22 |
| 6,260,857 B1 * | 7/2001 | Wienhold | ........... | B23B 31/1238 |
| | | | | 279/140 |
| D460,522 S | 7/2002 | Flinchbaugh | | |
| D488,866 S | 4/2004 | O'Dell | | |
| D543,509 S | 5/2007 | Mctor | | |
| D546,946 S | 7/2007 | Blake et al. | | |
| D550,624 S | 9/2007 | McCann | | |
| D558,673 S | 1/2008 | Easley | | |
| D566,653 S | 4/2008 | Sakamoto | | |
| D567,180 S | 4/2008 | Sakamoto | | |
| D574,781 S | 8/2008 | Chawgo et al. | | |
| 7,517,179 B2 * | 4/2009 | Miller | .................... | B23B 31/06 |
| | | | | 408/239 R |
| D654,166 S | 2/2012 | Lair | | |
| 8,882,113 B2 * | 11/2014 | Porter | ................. | B25B 23/0035 |
| | | | | 279/22 |
| D746,448 S | 12/2015 | Wu et al. | | |
| D775,683 S | 1/2017 | Shipard | | |
| 9,755,351 B1 | 9/2017 | Nicholson | | |
| D847,752 S | 5/2019 | Barrefelt et al. | | |
| D861,161 S | 9/2019 | Schuessler | | |
| D912,245 S | 3/2021 | Grudo et al. | | |
| D923,788 S | 6/2021 | Sweitzer et al. | | |
| D930,123 S | 9/2021 | Garcia | | |
| D932,291 S | 10/2021 | Grøndal | | |
| 11,224,472 B2 * | 1/2022 | Rodriguez | ......... | A61B 17/7082 |
| D948,441 S | 4/2022 | Takano et al. | | |
| 11,499,467 B2 | 11/2022 | Nelson | | |
| 11,512,760 B2 | 11/2022 | Pachys | | |
| D975,273 S | 1/2023 | Theriot | | |
| 2018/0297184 A1 * | 10/2018 | Bailey | ...................... | F16D 7/08 |

FOREIGN PATENT DOCUMENTS

| | | | | |
|---|---|---|---|---|
| JP | D1727184 | 10/2022 | | |
| WO | WO-2012121601 A1 * | 9/2012 | ........... | B23B 31/107 |

OTHER PUBLICATIONS

Hyper Tough 3-Piece Quick Connect Socket Adapter Set AU85043K, Hyper Tough, Wal mart.com, [Post date unknown], [Site seen May 16, 2023], Seen at URL: https://www.walmart.com/ip/Hyper-Tough-3-Piece-Quick-Connect-Socket-Adapter-Set-AU85043K/ 17 4619262 (Year: 2023).

United Stated Patent and Trademark Office, Notice of Allowance received in counterpart U.S. Appl. No. 29/877,866 dated Jul. 30, 2024.

* cited by examiner

QUICK CONNECT FOR A MEDICAL DEVICE

CROSS-REFERENCE TO RELATED APPLICATIONS

This application claims the benefit under 35 U.S.C. § 119(e) to U.S. Provisional Application No. 63/013,123, filed Apr. 21, 2020 and entitled "Quick Connect for a Medical Device," the entire disclosure of which is hereby incorporated by reference for all purposes.

FIELD OF THE DISCLOSURE

Exemplary embodiments of the subject disclosure relate generally to a quick connect device. In particular, the exemplary embodiments of the subject disclosure relate to a device to which a medical device such as an implant extraction tool extension handle may be quickly and firmly connected.

BACKGROUND OF THE DISCLOSURE

Conventional quick connect devices permit play or wobbling of a device connected thereto. That is, there is no suitably rigid connection between a connected device, e.g., an implant extraction tool, to the quick connect device. As such, this results in an undesirably loose fit of the implant extraction tool to the quick connect device which can cause the implant extraction tool to move about during an implant extraction procedure. As a result, the implant extraction tool, which is commonly struck by a striking tool during implant extraction, does not effectively convey the striking force of the striking tool from the implant extraction tool through the quick connect. Consequently, the implant extraction tool may require a greater number of strikes and/or more forceful strikes than would be necessary if there were a suitably rigid connection between the implant extraction tool and the quick connect device, and any subsequently connected tool attached to the quick connect, e.g., a working tool on an end of the quick connect opposite the implant extraction tool. Therefore, in addition to prolonging the implant extraction procedure, a user, e.g., a surgeon or other medical provider, must exert more energy than necessary to extract an implant from bone along with exposing the bone to unnecessary striking forces.

BRIEF SUMMARY OF THE DISCLOSURE

In accordance with an exemplary embodiment of the subject disclosure, a quick connect is provided for a medical device. The quick connect includes a housing, a slide lock mounted within the housing, and a locking assembly mounted within the housing. The slide lock is for receiving a cooperating connection adapter. The locking assembly includes a substantially annular member having a superiorly facing sloped recess. The substantially annular member is movable along a longitudinal axis of the housing upon rotation of the substantially annular member.

The locking assembly can further include a ball mounted within the superiorly facing sloped recess. The locking assembly also includes a plurality of plates movable along the longitudinal axis of the housing upon movement of the substantially annular member, where one of the plurality of plates extends beyond an inferior surface of the housing. In other words, the locking assembly can further include a plate movable along the longitudinal axis of the housing upon movement of the substantially annular member. The plate can extend beyond an inferior end of the housing. The housing can include a recess for receiving a ball. The substantially annular member can include a recess about its inferior end for receiving a ball. The locking assembly can further include a sleeve circumscribed by the housing and includes a plurality of splines. The locking assembly can further include a biasing member biasing the substantially annular member. The slide lock includes a first clamping portion and a second clamping portion moveable relative to the first clamping portion. The slide lock can further include a biasing member for biasing the first and second clamping portions. The slide lock can extend between opposing lateral sides of the housing and the quick connect can further include a cooperating connection adapter for releasably connecting with the slide lock.

In accordance with another exemplary embodiment, the subject disclosure provides a quick connect for a medical device. The quick connect includes a housing, a slide locking mechanism mounted within the housing, and a collar assembly. The slide locking mechanism is movable between a locked position and an unlocked position. The collar assembly includes a collar lock engaging the housing and a base mounted to the housing. The collar lock is movable along a longitudinal axis of the housing upon rotation therewith. The base includes a biasing device extending proud from a superior facing surface of the base for engaging the collar lock.

The biasing device can include a shaft and a biasing member biasing the shaft. The biasing device can bias the collar lock. The housing can include external threads and internal threads about its inferior end. The collar lock can threadedly engage the external threads of the housing. The base can threadedly engage the internal threads of the housing. The quick connect can further include a cooperating connection adapter for releasably connecting with the slide locking mechanism. The quick connect can further include a fastener extending from a superior end of the housing. The base can include a central through hole for receiving a cooperating connection adapter.

Other features and advantages of the subject disclosure will be apparent from the following more detailed description of the exemplary embodiments.

BRIEF DESCRIPTION OF THE SEVERAL VIEWS OF THE DRAWINGS

The foregoing summary, as well as the following detailed description of the exemplary embodiments of the subject disclosure, will be better understood when read in conjunction with the appended drawings. For the purpose of illustrating the present disclosure, there are shown in the drawings exemplary embodiments. It should be understood, however, that the subject application is not limited to the precise arrangements and instrumentalities shown.

In the drawings:

FIGS. 4A-4D are various views of the quick connect of FIG. 1A in a locked or disengaged state with certain components omitted and/or in phantom for purposes of illustration;

Figure 1A:
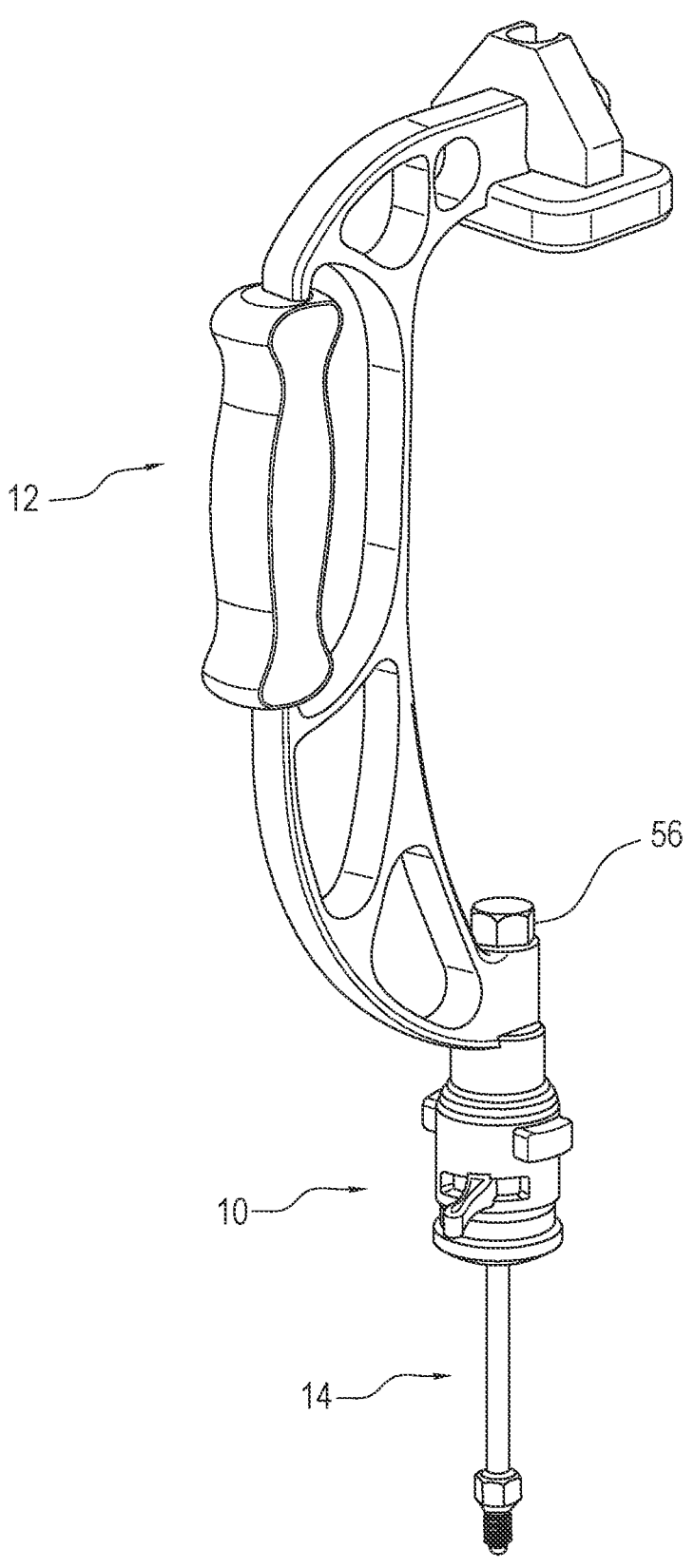
FIGS. 1A-1B are perspective views of an exemplary quick connect in accordance with an exemplary embodiment of the subject disclosure.
Figure 1B:
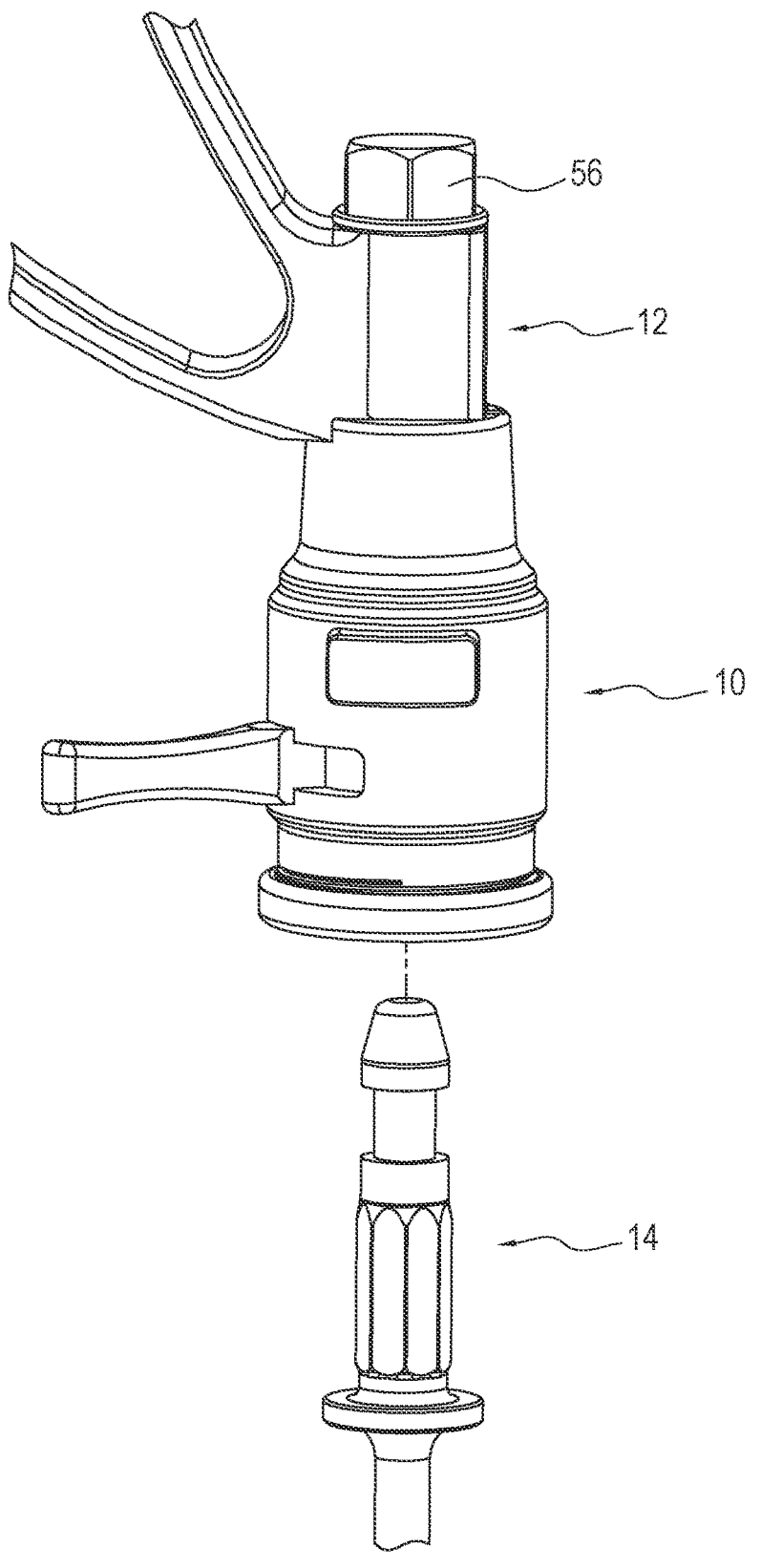

DETAILED DESCRIPTION OF THE
DISCLOSURE

Reference will now be made in detail to the various exemplary embodiments of the subject disclosure illustrated in the accompanying drawings. Wherever possible, the same or like reference numbers will be used throughout the drawings to refer to the same or like features. It should be noted that the drawings are in simplified form and are not drawn to precise scale. Certain terminology is used in the following description for convenience only and is not limiting. Directional terms such as top, bottom, left, right, above, below and diagonal, are used with respect to the accompanying drawings. The term "superior" refers to a direction towards an upper, or "head," end of the body. The term "inferior" refers to a direction towards a lower end of the body and/or away from the "superior" end. The terms "inwardly" and "outwardly" refer to directions toward and away from, respectively, the geometric center of the identified element and designated parts thereof. Such directional terms used in conjunction with the following description of the drawings should not be construed to limit the scope of the subject application in any manner not explicitly set forth. Additionally, the term "a," as used in the subject disclosure, means "at least one." The terminology includes the words above specifically mentioned, derivatives thereof, and words of similar import.

"About" as used herein when referring to a measurable value such as an amount, a temporal duration, and the like, is meant to encompass variations of ±20%, ±10%, ±5%, ±1%, or ±0.1% from the specified value, as such variations are appropriate.

"Substantially" as used herein shall mean considerable in extent, largely but not wholly that which is specified, or an appropriate variation therefrom as is acceptable within the field of art. "Exemplary" as used herein shall mean serving as an example.

Throughout the subject disclosure, various aspects thereof can be presented in a range format. It should be understood that the description in range format is merely for convenience and brevity and should not be construed as an inflexible limitation on the scope of the subject disclosure. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Furthermore, the described features, advantages and characteristics of the exemplary embodiments of the subject disclosure may be combined in any suitable manner in one or more embodiments. One skilled in the relevant art will recognize, in light of the description herein, that the subject disclosure can be practiced without one or more of the specific features or advantages of a particular exemplary embodiment. In other instances, additional features and advantages may be recognized in certain embodiments that may not be present in all exemplary embodiments of the present disclosure.

FIG. 1A illustrates an exemplary embodiment of a quick connect 10 for a medical device in accordance with the subject disclosure. The quick connect is engageable with a cooperating connection adapter 14. The quick connect allows a user to quickly connect and release the connection adapter thereto, which is also intended to be connectable to other various medical devices. The quick connect can also be connected to another instrument, e.g., a C-frame device 12, at an end opposite the quick connect end.

The quick connect 10 is configured as shown in FIGS. 1A, 1B, 4A, and 4B and includes a superior end 16, an inferior end 18, a housing 20, a slide lock 22 mounted within the housing, and a locking assembly 24 mounted within the housing. The quick connect is cooperatively engageable with, e.g., a C-frame 12, and the connection adapter 14. The C-frame is an extension handle for an implant extraction tool.

Figure 18A:
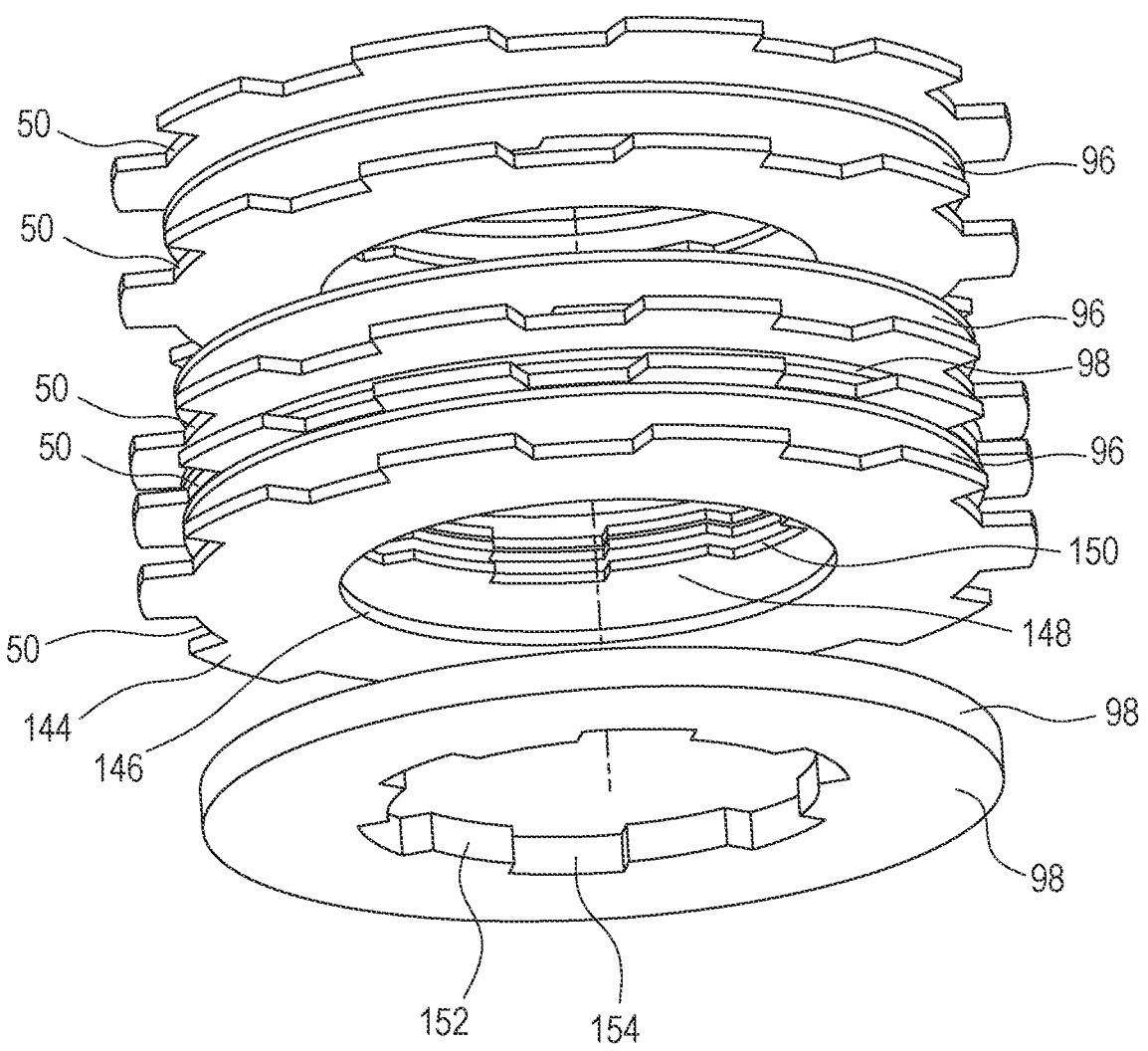
FIGS. 18A-18C and 19 are various views of various plates of the quick connect of FIG. 1A.
Figure 18B:
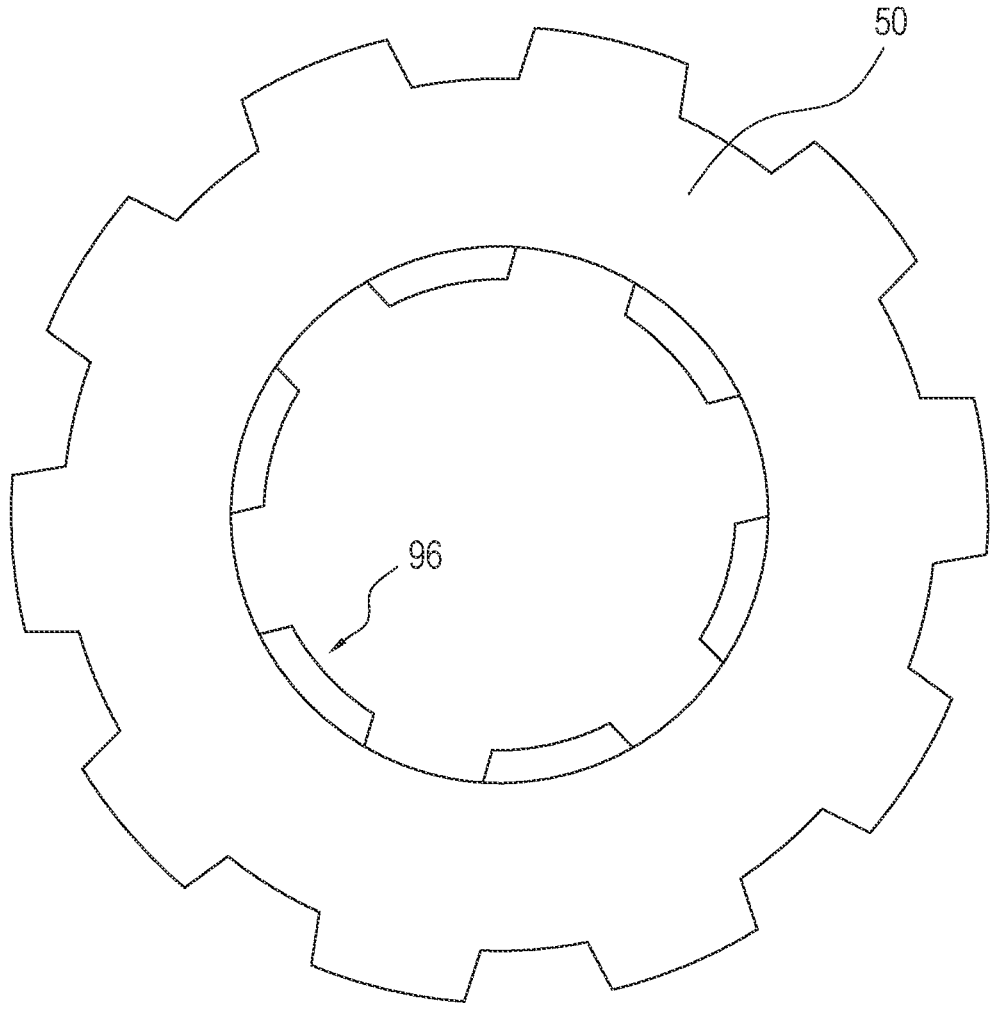
Figure 18C:
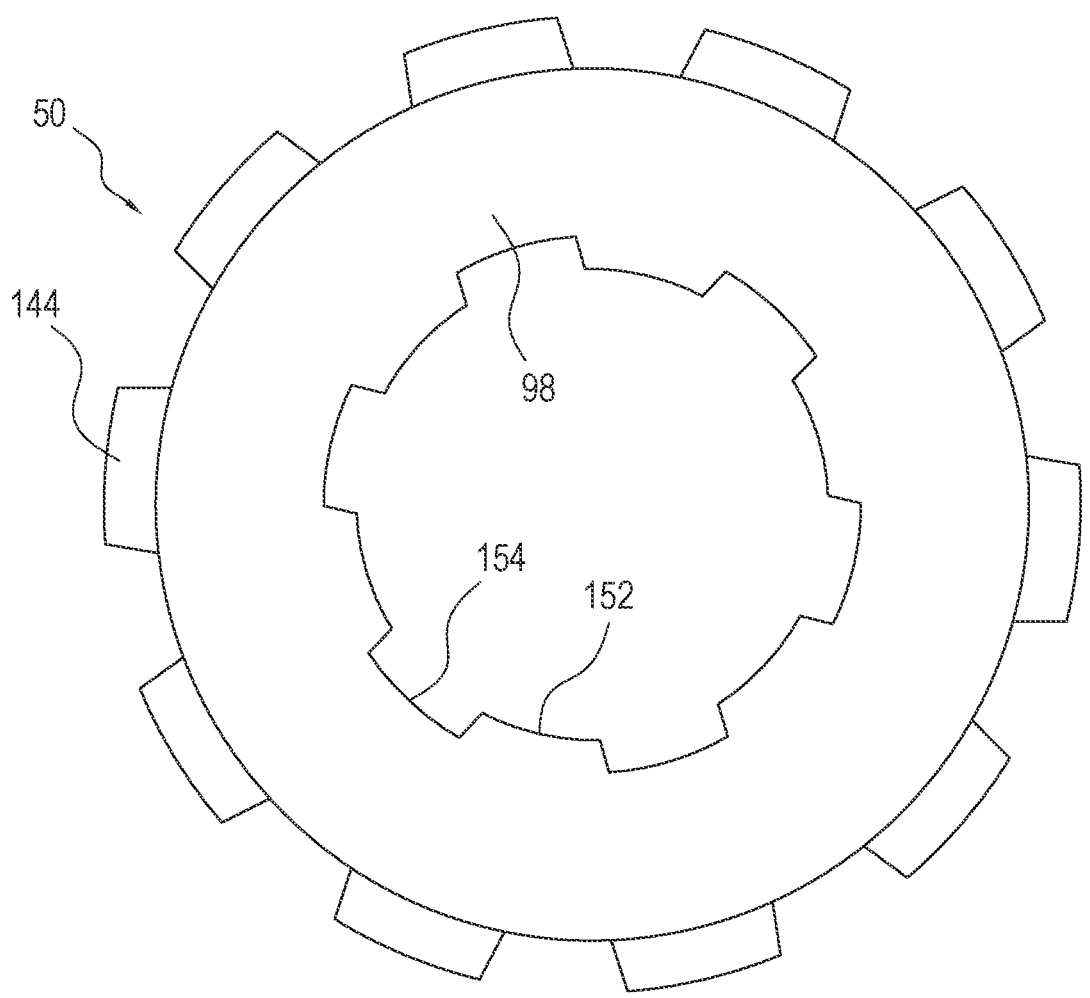
Figure 19:
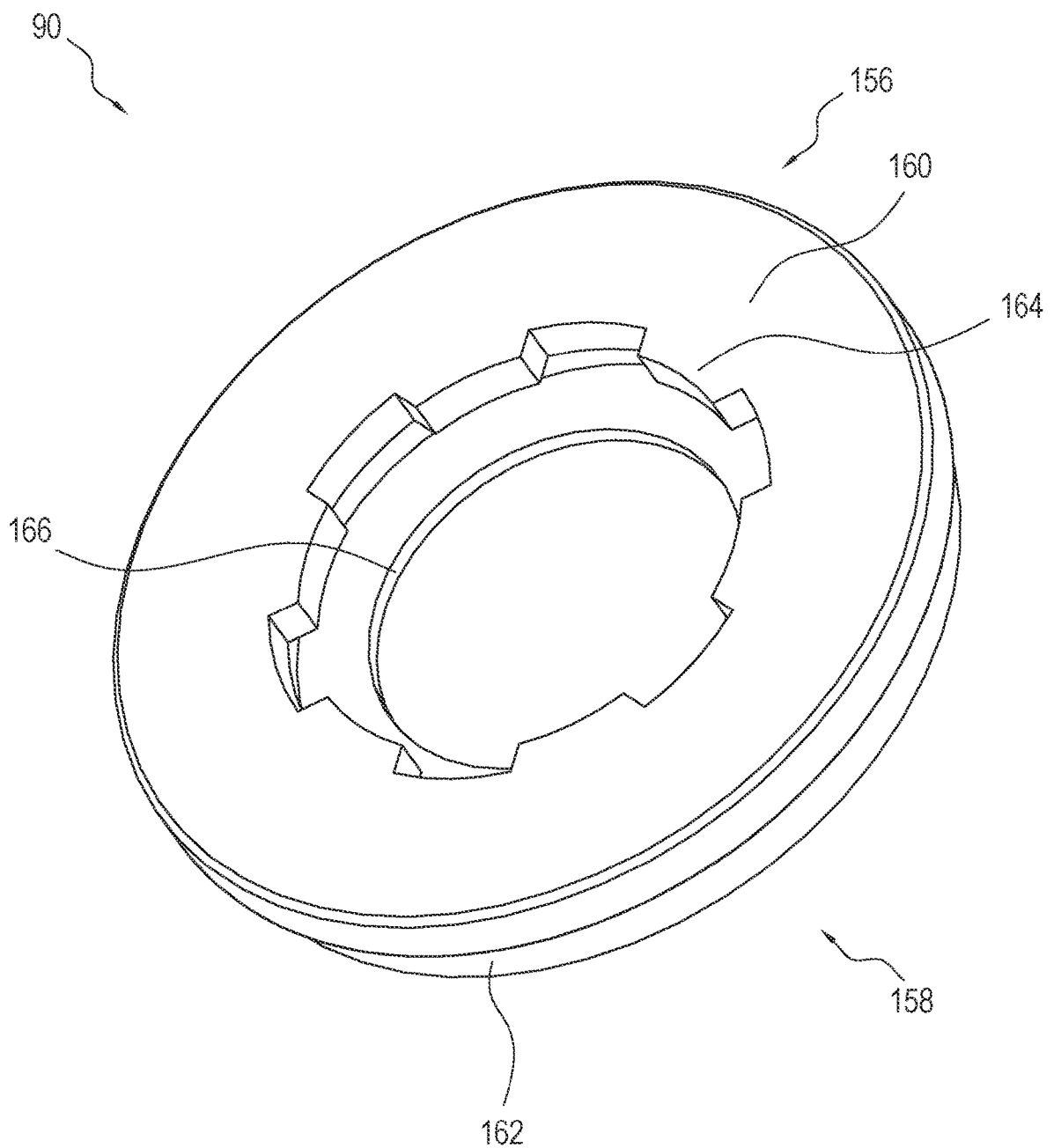

Referring to FIGS. 5A, 5B, 5D, and 11A-11C, the housing 20 of the quick connect 10 has a superior end 26 and an inferior end 28. The housing includes a central through hole 30 and one or more through holes 32 laterally spaced from the central through hole. The housing also includes a slot or elongated window 34 for receiving an arm 36 extending from a substantially annular member 38 and one or more lateral through holes 40 for receiving one or more lock buttons 42 of the slide lock 22. The housing further includes one or more recesses 44 for receiving one or more balls 46, internal splines 48 about its inferior end for cooperating engagement with one or more clutch discs 50 (FIG. 18A), and external threads 52 about its inferior end for threaded engagement with a base 54 (FIG. 20) of the quick connect.

The central through hole 30 of the housing 20 is adapted for receiving a fastener 56. The fastener can be a bolt having a stem 58 that is securely received in the central through hole. The bolt connects the housing to a secondary instrument, e.g., a C-frame, that extends from the superior end of the housing.

The through holes 32 of the housing are arranged on opposing lateral sides of and laterally spaced from the central through hole 30. Each through hole 32 is adapted to receive a pin that operates to limit the lateral movement (e.g., travel) of each lock button of the slide lock, as described in further detail below. Alternatively, the through holes can be configured as counterbores.

The slot 34 of the housing provides access to the arm 36 extending from the substantially annular member 38. The slot is adapted to limit rotation of the arm about a longitudinal axis of the housing so as to limit corresponding rotation of the substantially annular member. For example, the slot is configured to have an arc length of about 30 to 90 degrees, including 20, 25, 30, 35, 40, 45, 50, 55, 60, 65, 70, 75, 80, 85, 90, 95, and 100 degrees.

Figure 5A:
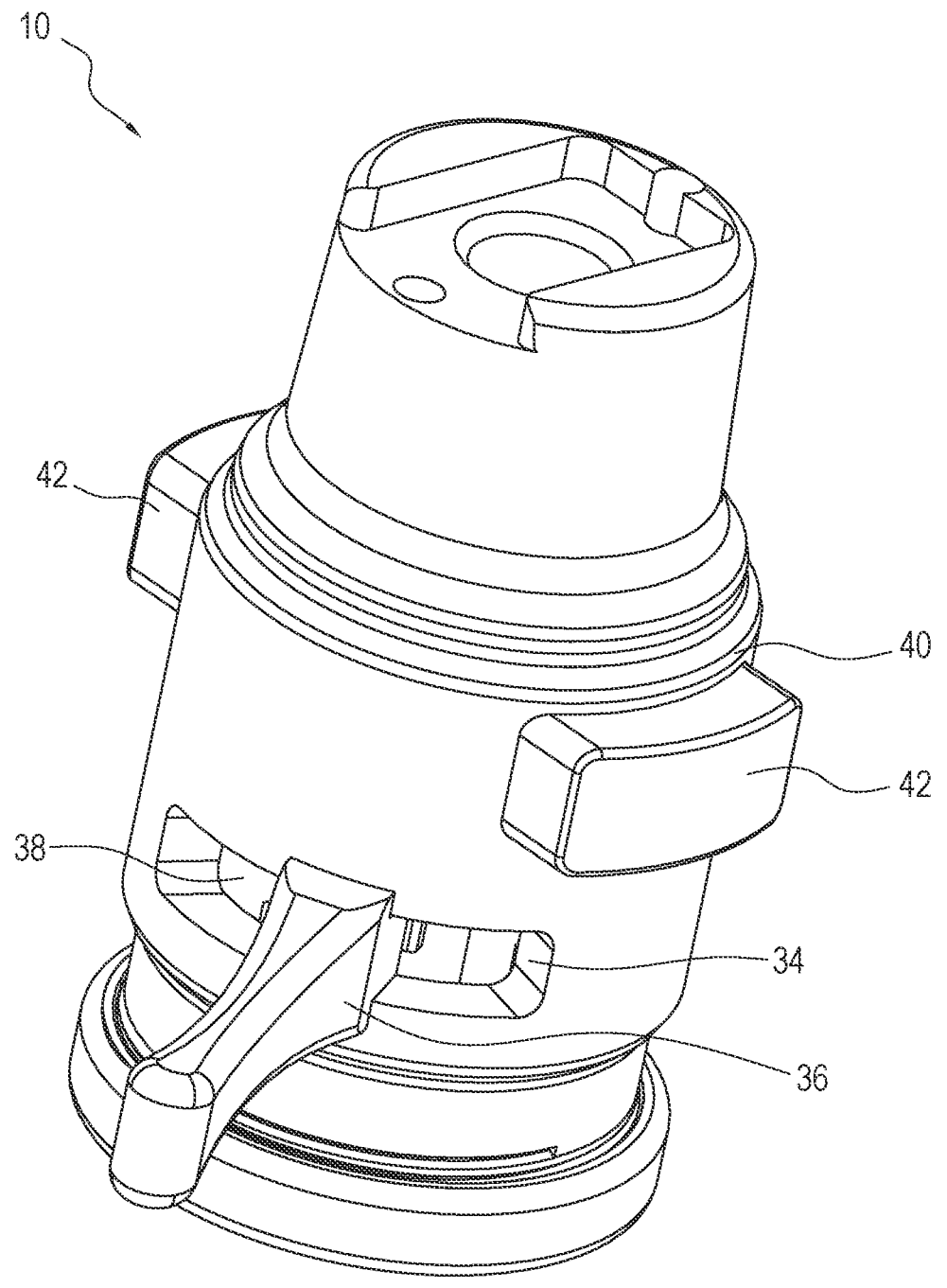
FIGS. 5A-5D are various views of the quick connect of FIG. 1A in transition to an engaged, disengaged, or unlocked state with certain components omitted and/or in phantom for purposes of illustration.
Figure 5B:
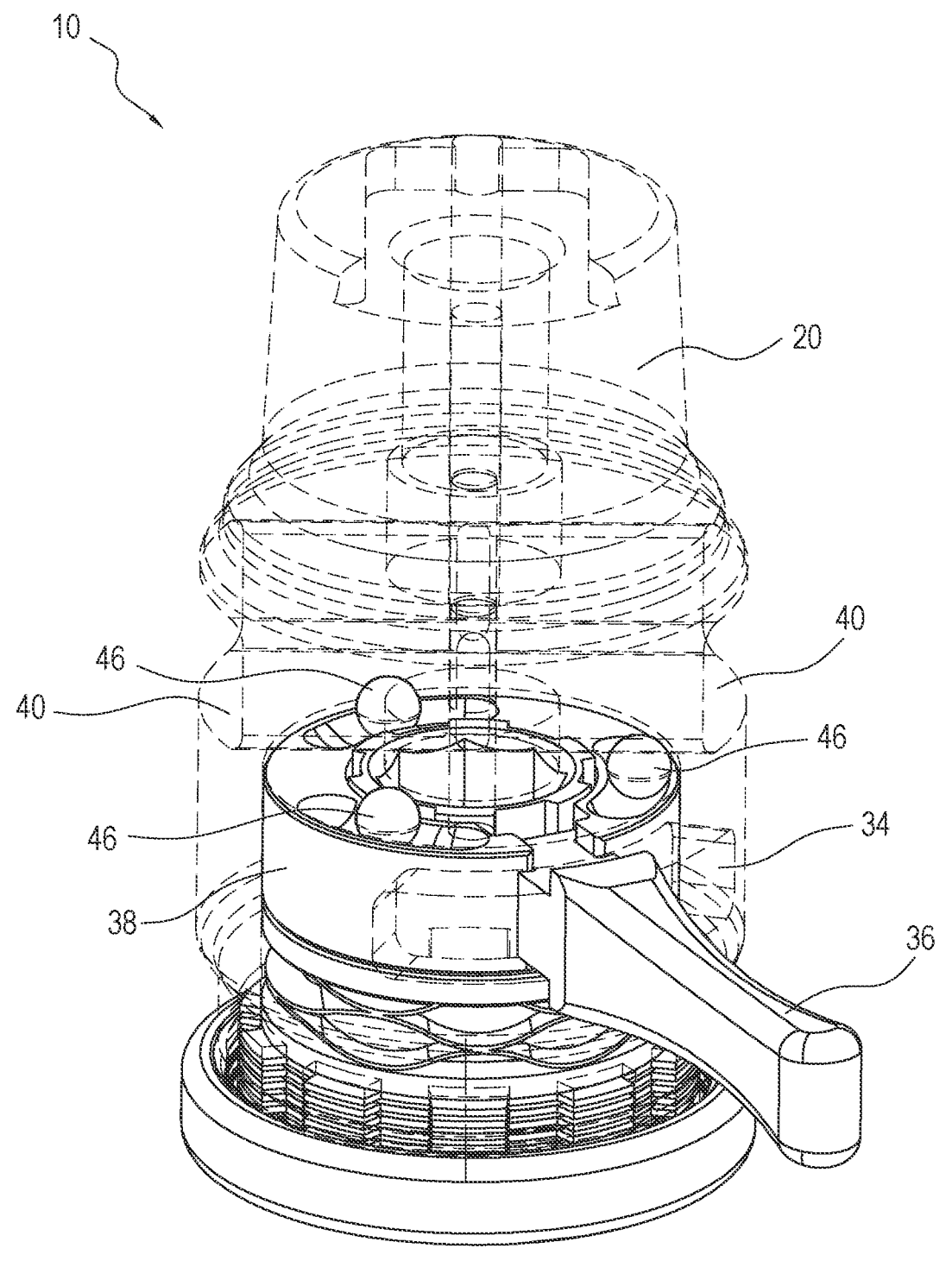

The recesses 44 of the housing are adapted to receive a corresponding ball 46 (FIG. 5B). Each recess fixes a ball in position relative to the substantially annular member that is rotatable relative to the housing. The interaction of the ball fixed in the recess with the rotation of the substantially annular member operates to move the substantially annular member along a length of a longitudinal axis A (FIGS. 4A-4B) of the housing, and as described in further detail below.

Referring to FIGS. 4A-4C, 5A and 7A-7B, the slide lock 22 of the quick connect 10 is mounted within the housing 20 for receiving the cooperating connection adapter 14. The slide lock includes one or more lock buttons 42 and one or more biasing members 60. The slide lock extends between opposing lateral sides of the housing. The slide lock is movable from a first position to a second position. The first position can be a locked position and the second position can be an unlocked position (FIGS. 12B-12C). In the first position (FIGS. 4C, 5A), the lock buttons extend between opposing lateral sides of the housing once the quick connect is connected to the connection adapter. In the second position (FIGS. 7A-7B), the user depresses each lock button inwardly which operates to release the quick connect from the connection adapter.

Figure 12A:
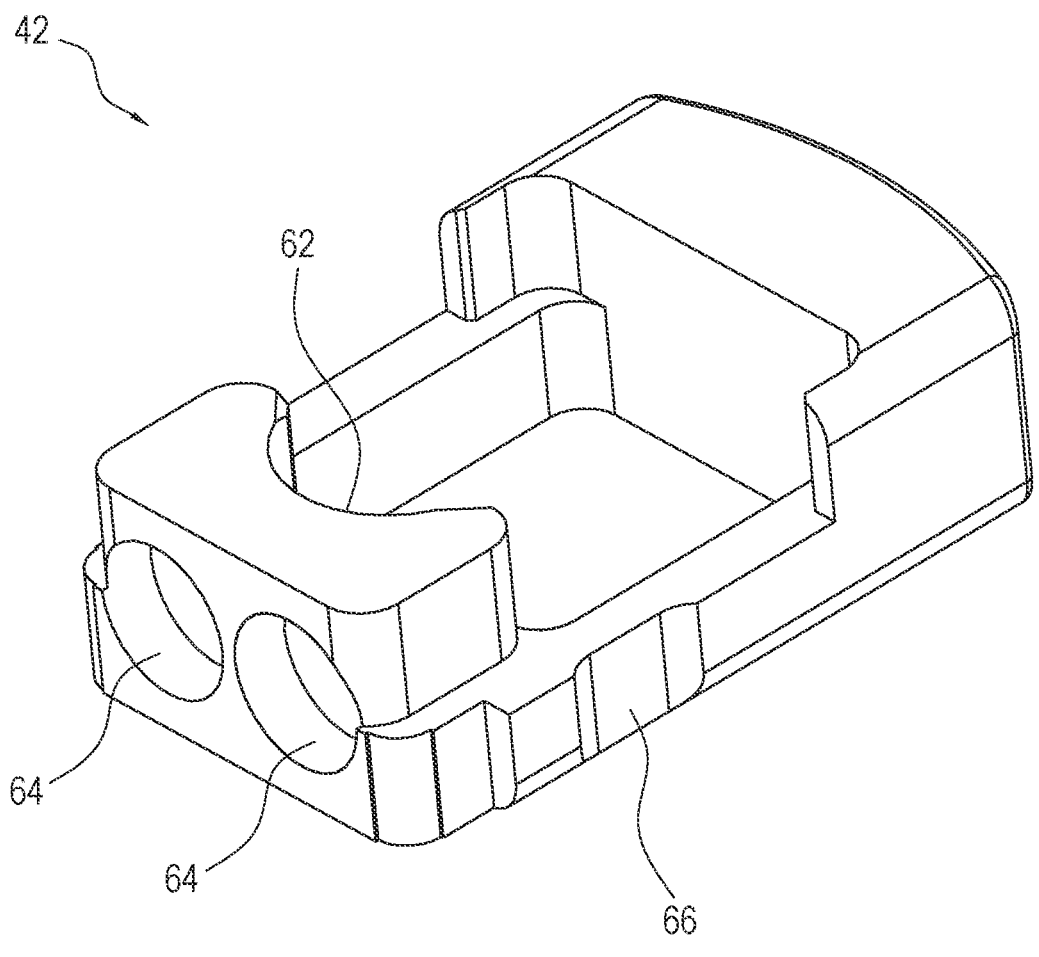
FIGS. 12A-12C are various views of a slide lock of the quick connect of FIG. 1A.
Figure 12B:
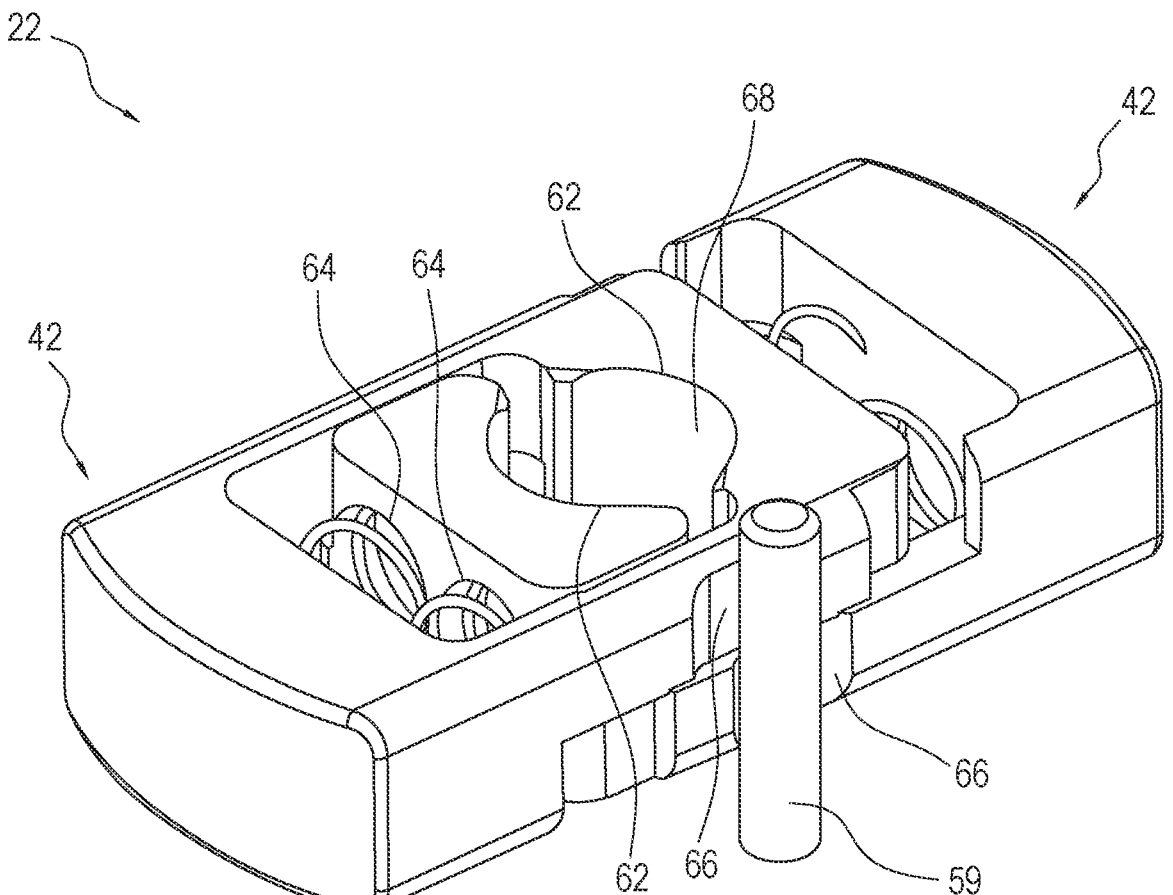
Figure 12C:
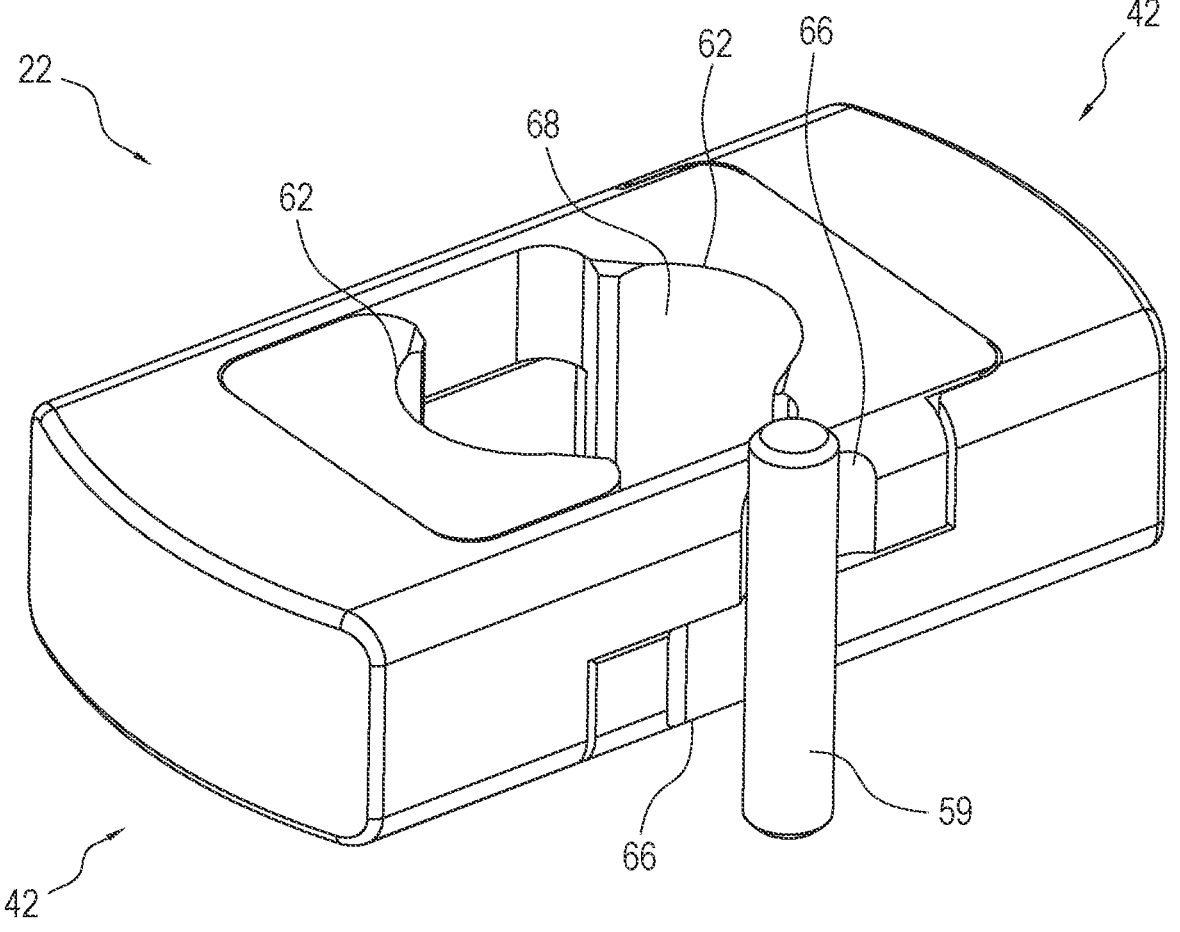

Referring to FIGS. 12A-12C, the lock buttons 42 of the slide lock 22 each have a clamping face 62, one or more blind holes 64, and a lateral recess 66. Each clamping face is configured with a recess, e.g., a substantially semi-circular recess. One of the lock buttons can be a first clamping portion and the other lock button can be a second clamping portion. The first and second clamping portions are movable relative to each other. When the slide lock is in the first position (FIG. 12B), the clamping faces of the cooperating lock buttons 42 are configured to define a central through hole 68. The central through hole of the slide lock is operable to receive the cooperating connection adapter. When the slide lock is transitioning from the first to the second position, the lock buttons move relative to one another. In the second position (FIGS. 7B, 12C) the size of the central through hole or spacing between the clamping faces enlarge due to the relative position of each clamping face so as to release the connection adapter or allow the connection adapter to pass through.

The blind holes of the lock button are adapted to receive the biasing members 60. In the first position the biasing members bias the lock buttons outwardly or towards the locking position. The recess 66 of the lock button is adapted to limit movement (e.g., travel) of each lock button between the first position (FIG. 12B) and the second position (FIG. 12C) by creating a limited travel path along which the lock buttons can travel without interfering with the pins 59 that are fixed in position.

Figure 2:
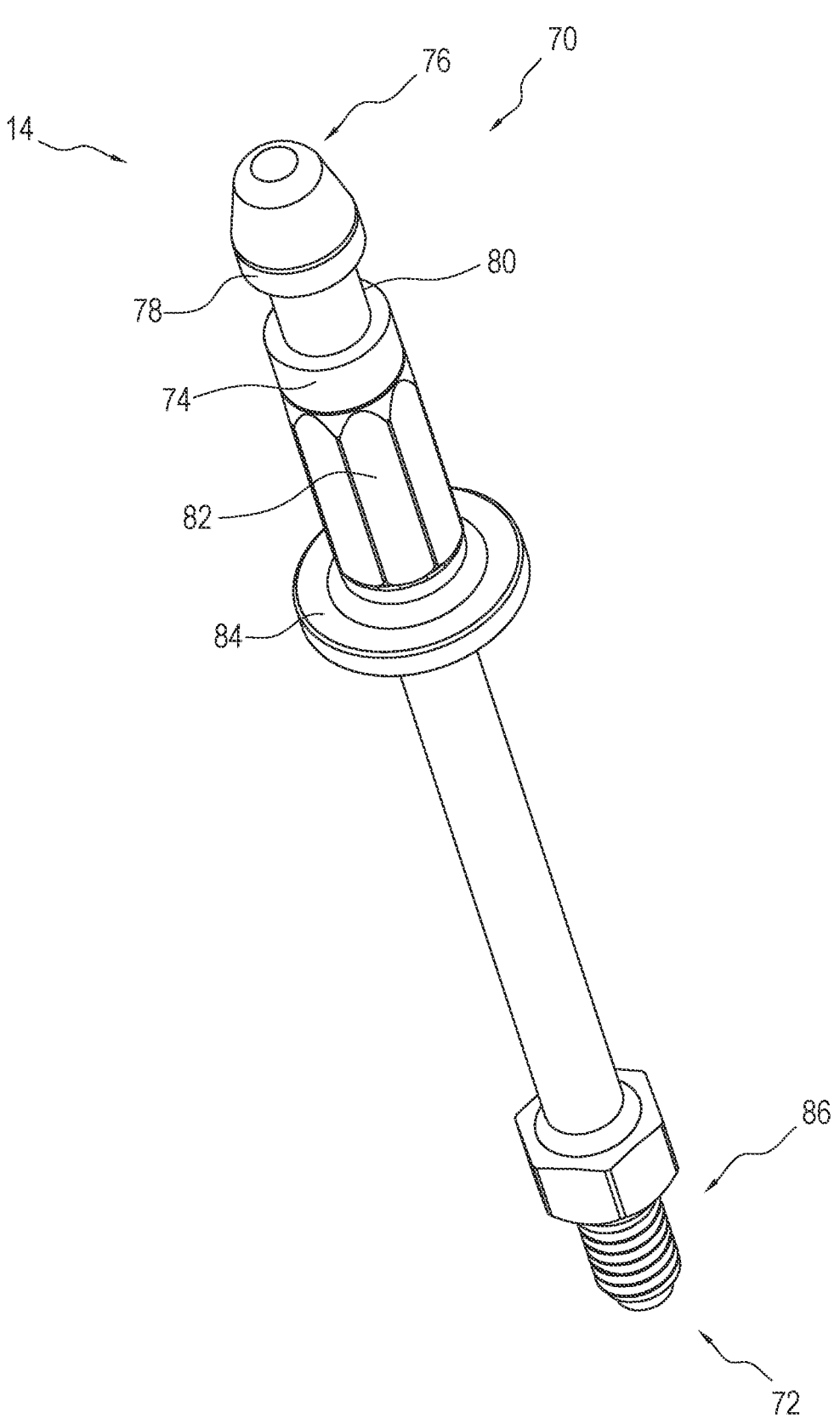
FIG. 2 is a perspective view of a connection adapter for cooperating engagement with the quick connect of FIG. 1A.
Figure 4A:
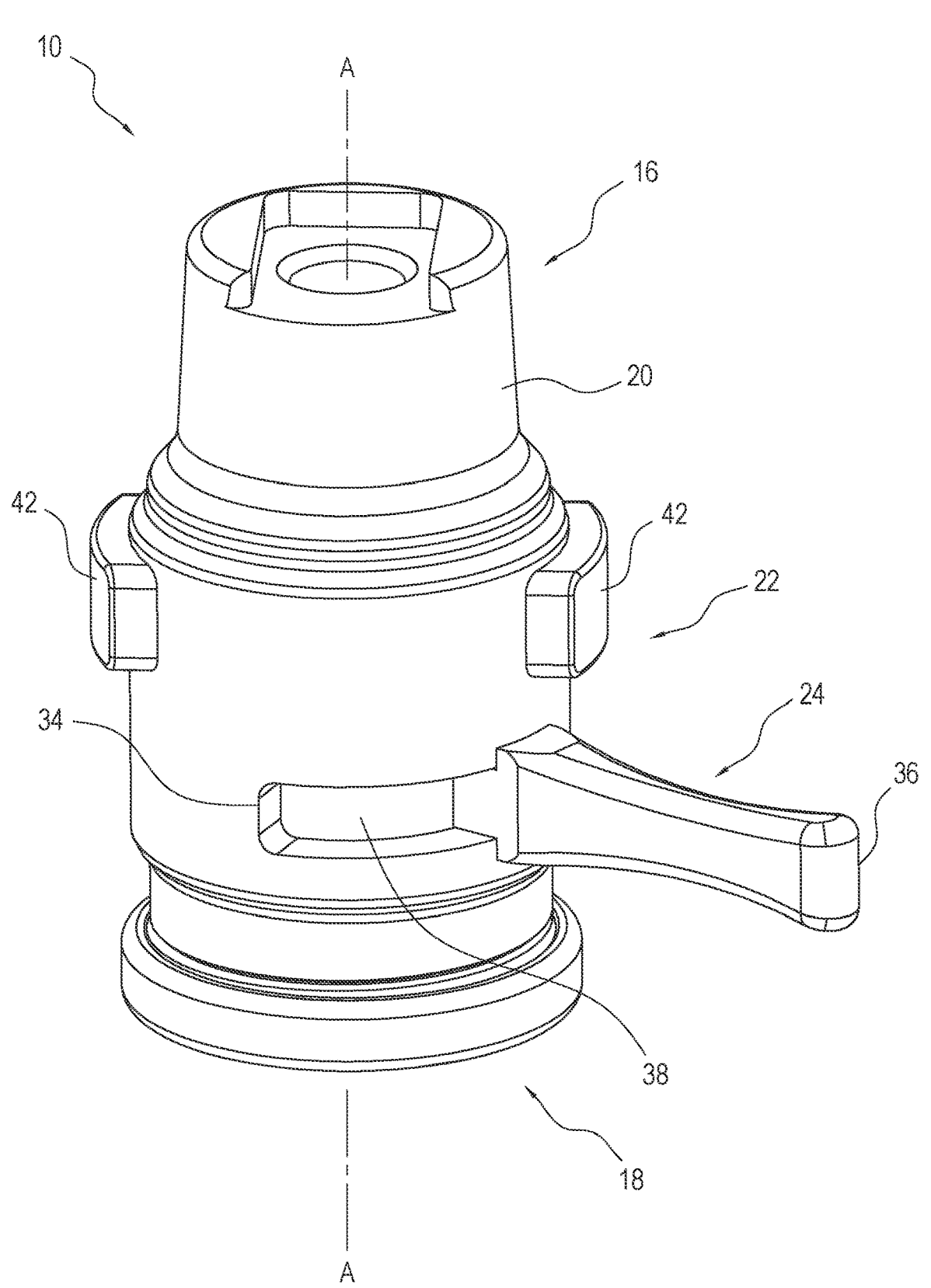
Figure 4B:
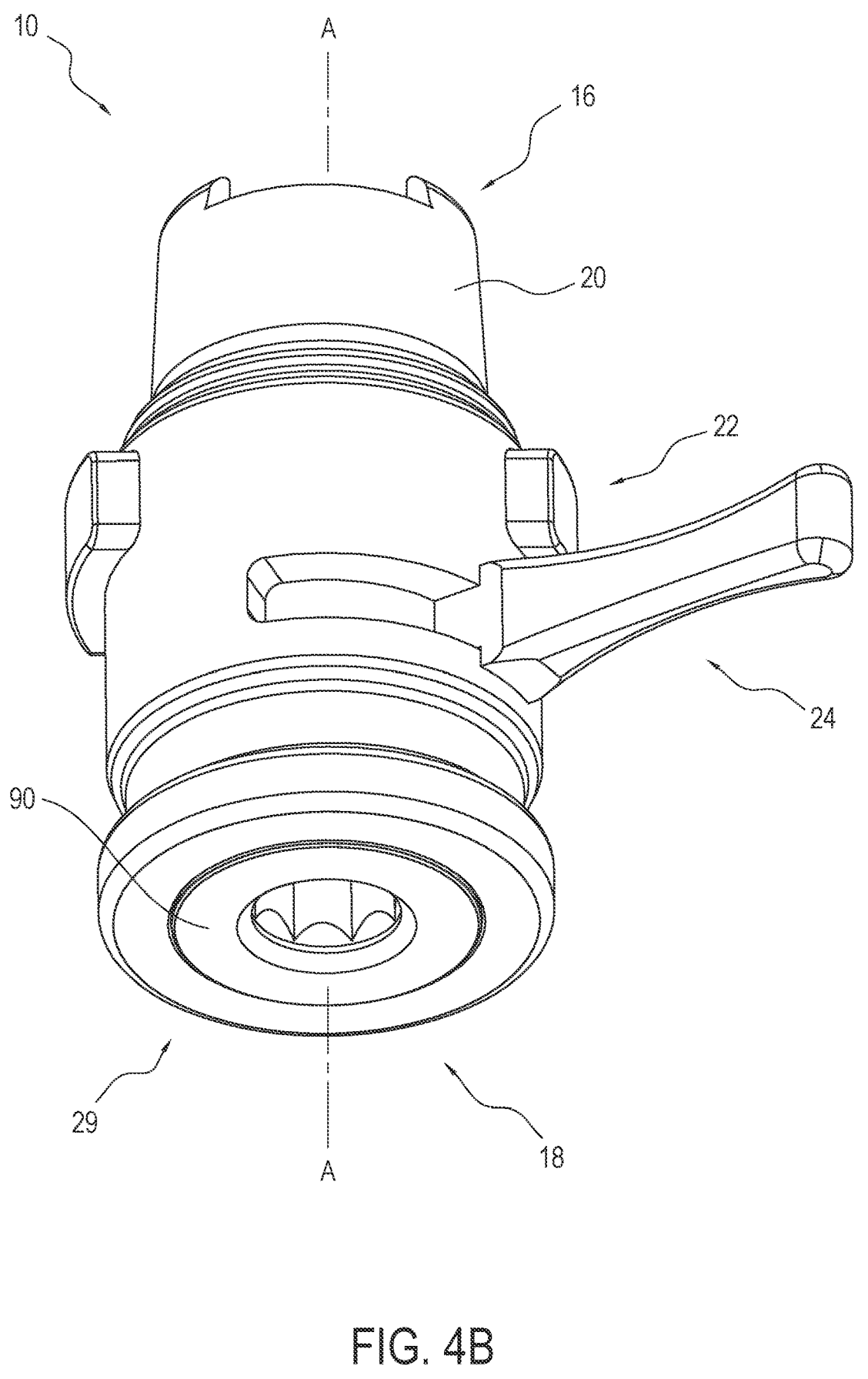
Figure 4C:
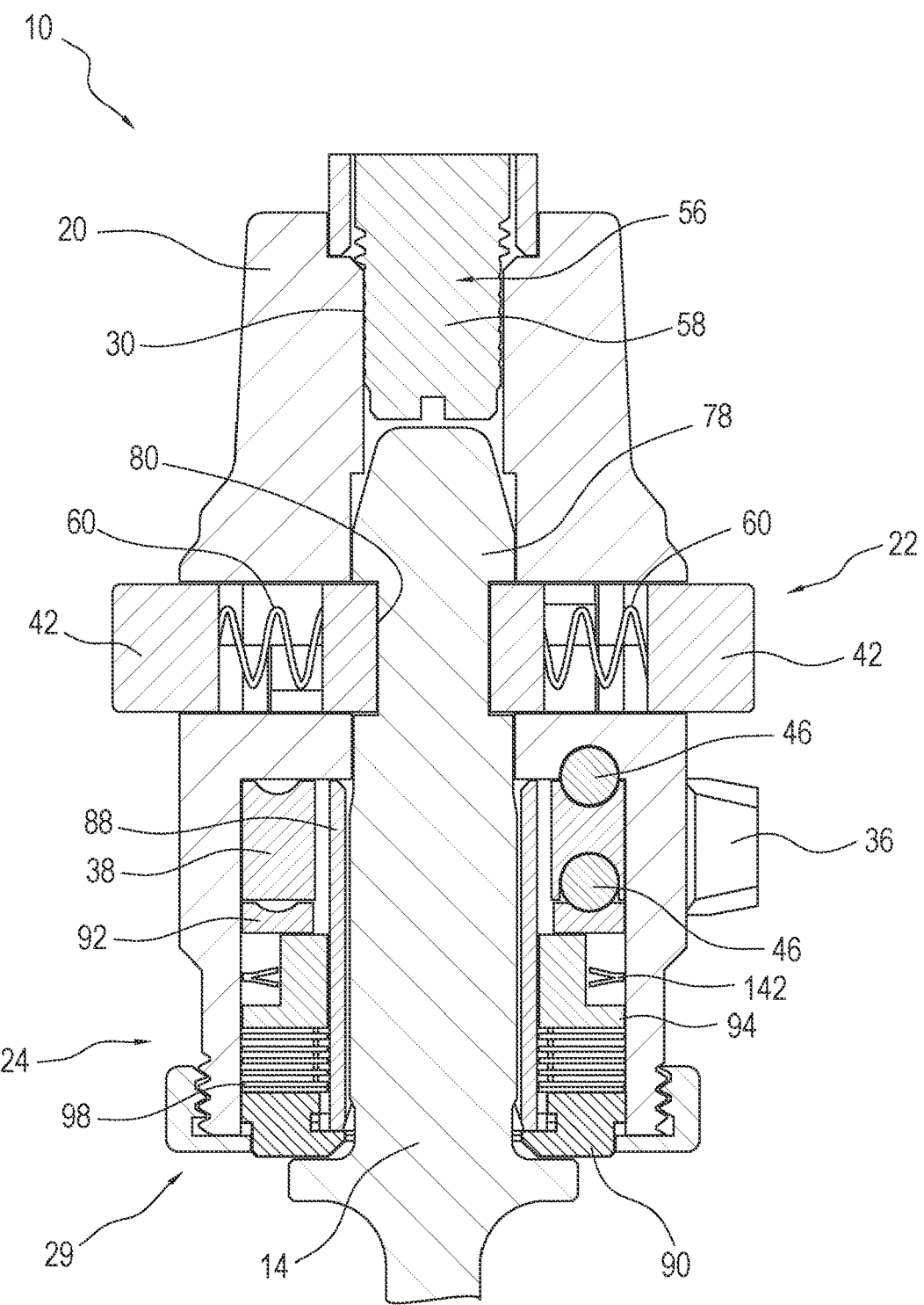

Referring to FIG. 2, the cooperating connection adapter 14 has a superior end 70 and an inferior end 72. The connection adapter can sometimes be referred to as a connection rod or a connection adapter. The connection adapter includes a shaft 74 having a frustoconical or conical end 76 about its superior end with a cylindrical base 78 and a reduced diameter portion 80. Referring to FIG. 4C, the reduced diameter portion 80 of the connection adapter operates in combination with the slide lock to keep the quick connect connected to the connection adapter. The connection adapter also includes a plurality of planar wall segments 82 defining a substantially octagonal longitudinal cross-section and a flange 84 about its superior end. The flange is positioned distal to the conical end 76. The connection adapter also includes a fastener 86 about its inferior end which is distal to the frustoconical end. The fastener allows the connection adapter to connect to a medical tool, e.g., an extraction tool. The frustoconical end 76 of the connection adapter is operable to push the lock buttons of the slide lock outwardly upon insertion of the connection adapter to the quick connect.

The planar wall segments 82 of the connection adapter are configured to be complementary to a sleeve 88 of the locking assembly 24 of the quick connect, as shown in FIG. 4C. Referring to FIG. 2, the planar wall segments are shown defining a substantially octagonal longitudinal cross-section. Alternatively, the planar wall segments can be arranged in any shape suitable to limit undesired rotation of the quick connect relative to the connection adapter via the sleeve. For example, the planar wall segments can have a triangular, square, pentagonal, hexagonal, heptagonal, nonagonal, decagonal, or other suitable longitudinal cross-section shape.

Figure 3A:
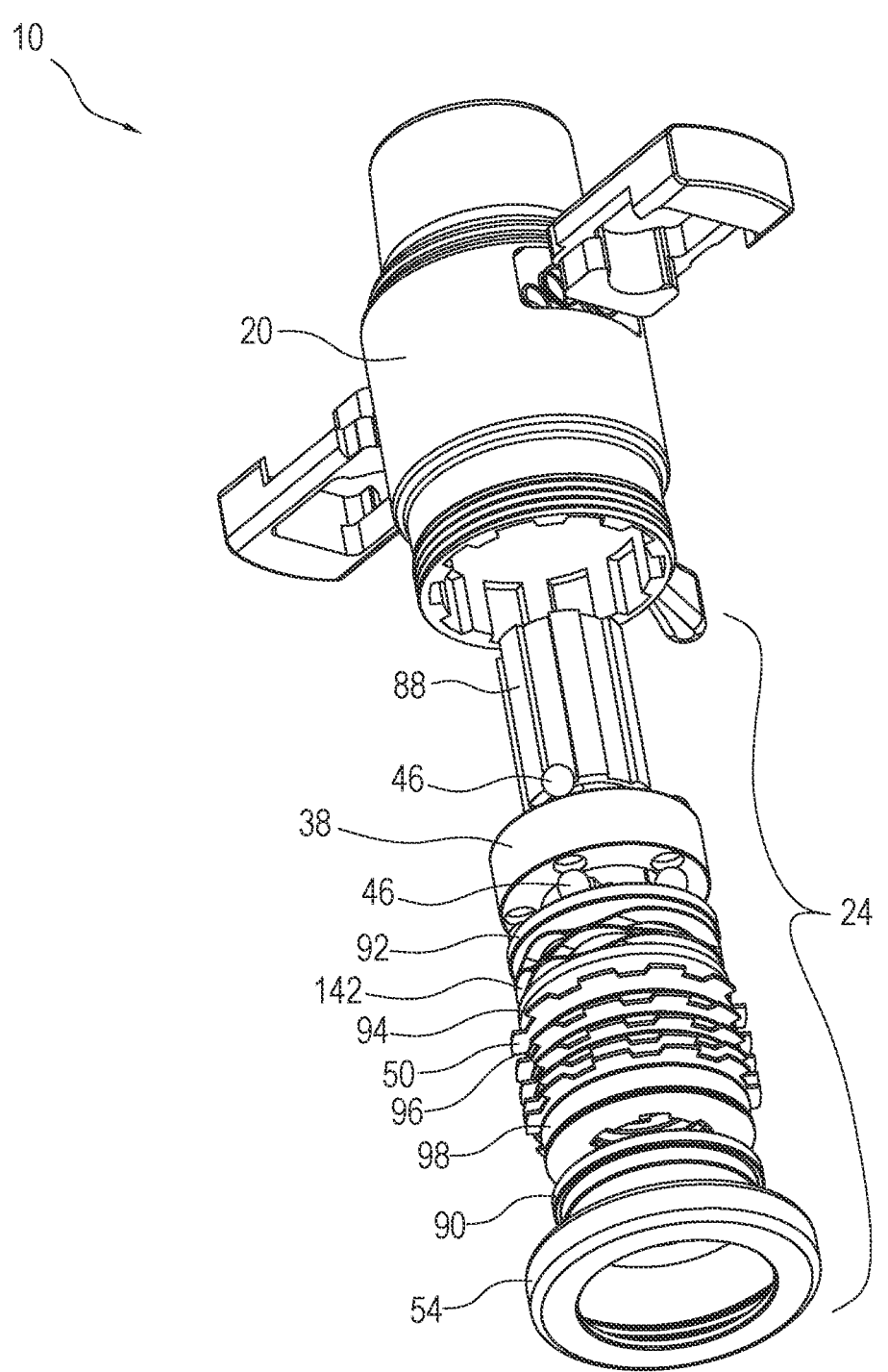
FIGS. 3A-3B are exploded views of the quick connect of FIG. 1A.
Figure 3B:
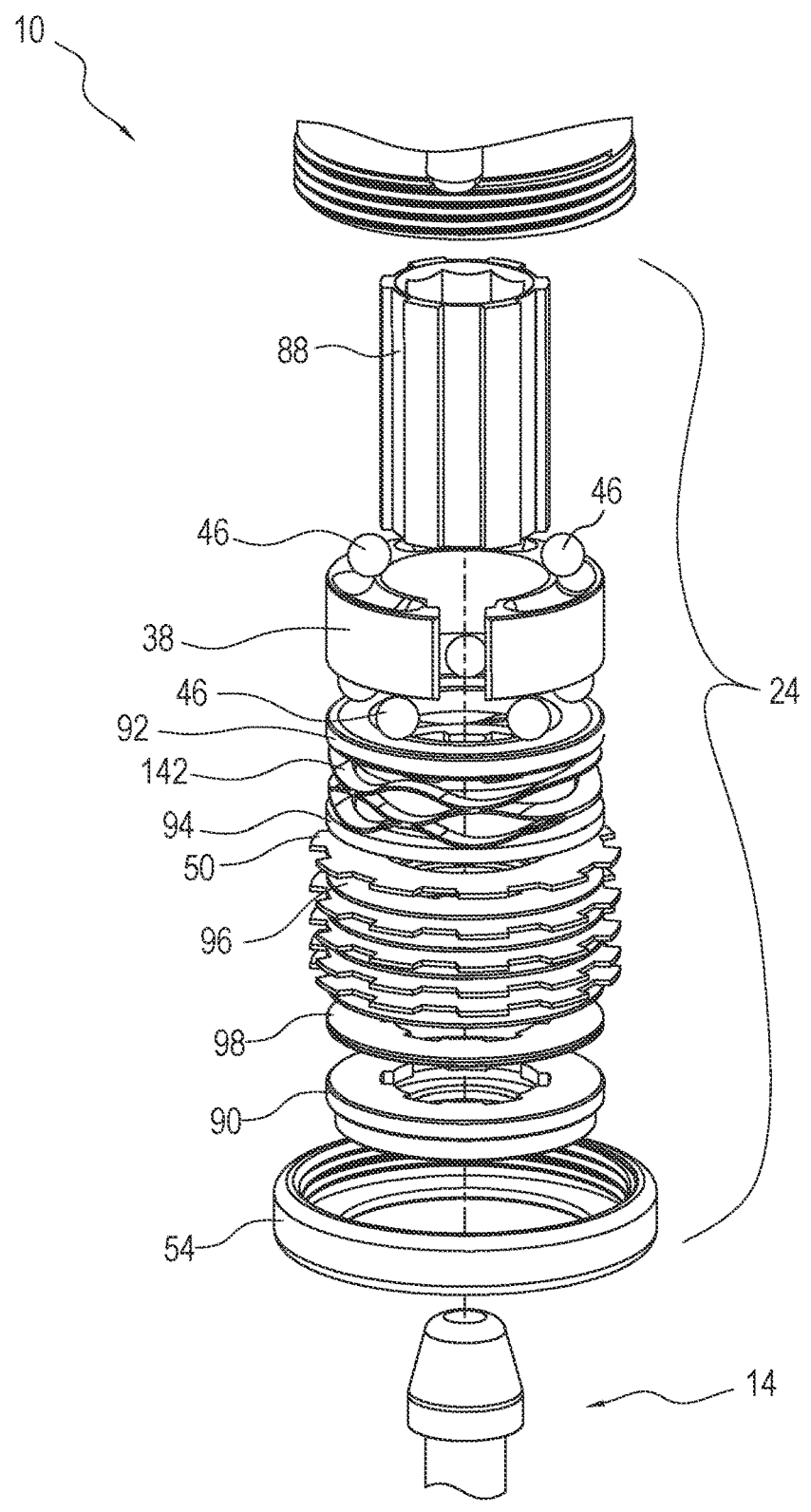

Referring to FIGS. 3A and 3B, the locking assembly 24 of the quick connect 10 is mounted within the housing 20. The locking assembly includes a substantially annular member 38, one or more balls 46, and a plurality or one or more plates 50, 90, 92, 94, 96, 98. The locking assembly locks the housing 20 of the quick connect to the connection adapter 14. Specifically, the locking assembly is movable along a longitudinal axis A (FIGS. 4A-4B) of the housing upon rotation of the substantially annular member to securely lock the quick connect to the connection adapter.

Figure 4D:
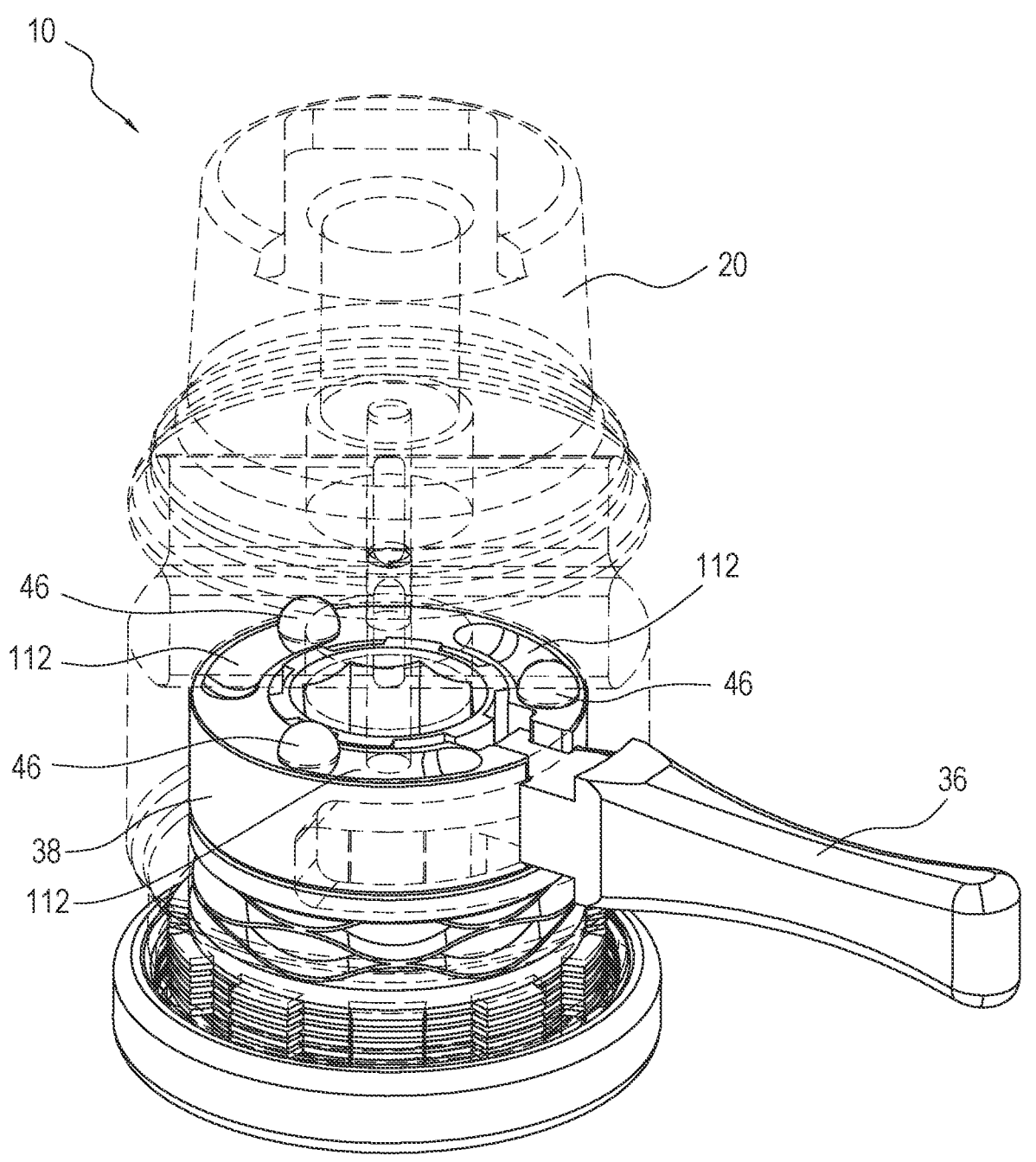
Figure 13A:
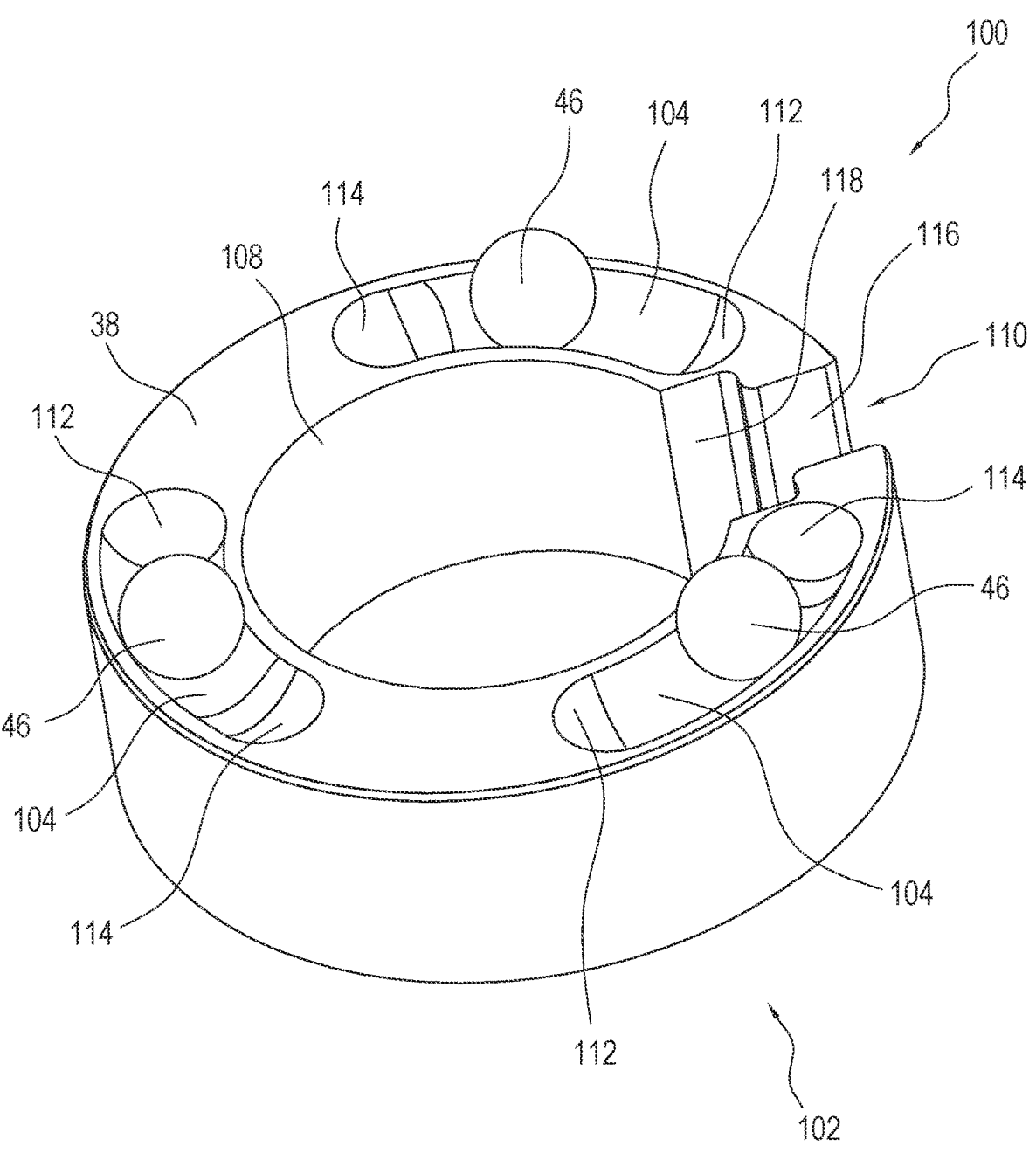
FIGS. 13A-13B are various perspective views of a substantially annular member of the quick connect of FIG. 1A.
Figure 13B:
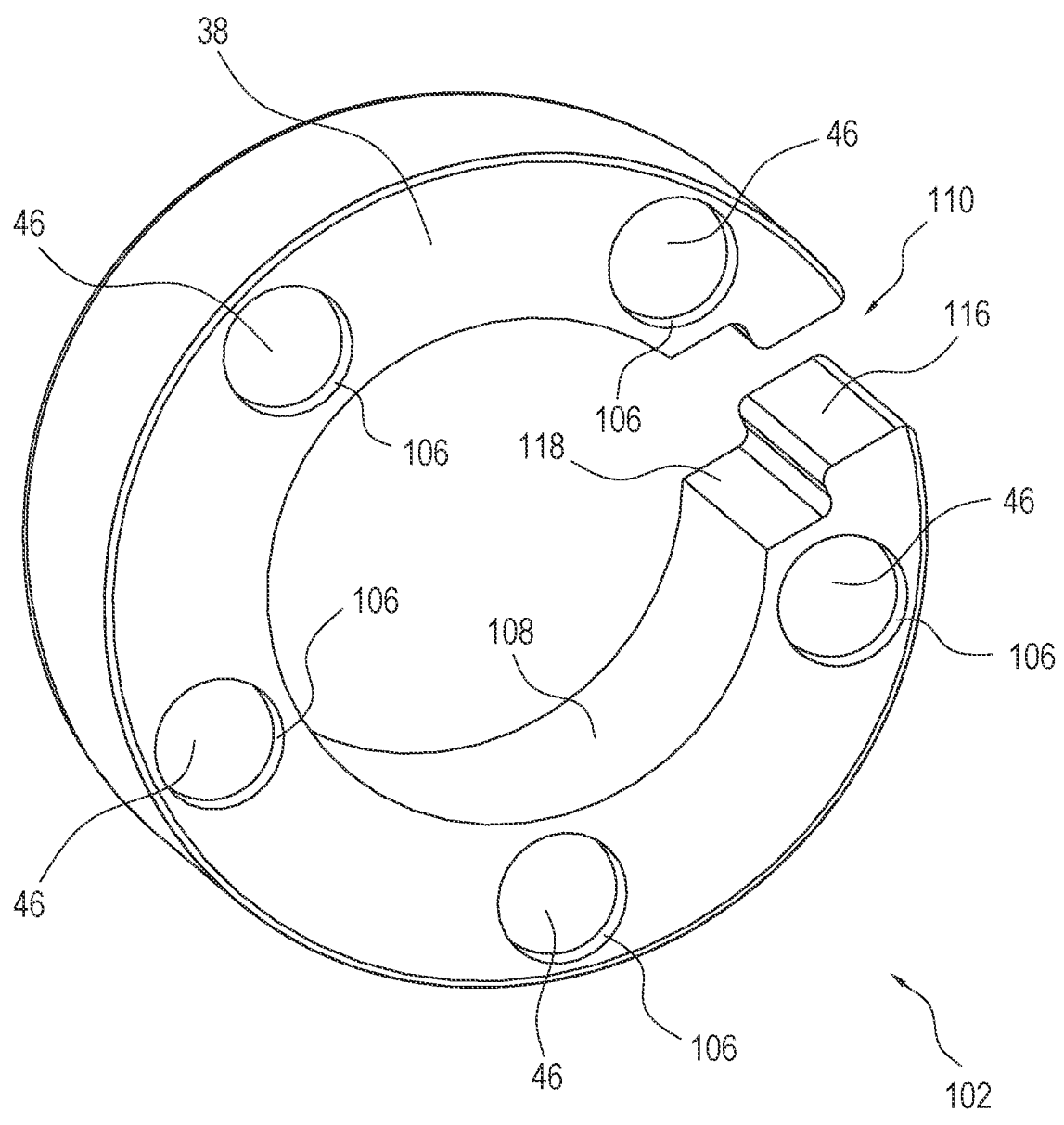
Figure 14:
FIG. 14 is a top plan view of an arm of the quick connect of FIG. 1A.

Referring to FIGS. 13A-13B, the substantially annular member 38 of the locking assembly has a superior end 100 and an inferior end 102. The substantially annular member is adapted to transmit torque from rotation of the arm extending from the substantially annular member into linear movement of the locking assembly along the longitudinal axis of the housing. The substantially annular member includes one or more superiorly facing sloped recesses or camming surfaces 104 (FIG. 13A) about its superior end and one or more recesses 106 (FIG. 13B) about its inferior end for receiving respective balls 46. The substantially annular member also includes a central longitudinal through hole 108 and an opening 110 for receiving and engaging the arm. Referring to FIGS. 4D, 5B, and 6B, the central through hole 108 of the substantially annular member is adapted for engagement with the sleeve 88 of the locking assembly 24. The opening is configured as a stepped or grooved opening for mating engagement with the arm extending radially outwardly from the substantially annular member (FIGS. 4D, 5B). The opening includes a smaller rectangular portion 116 and a larger rectangular portion 118 adapted for mating engagement with a flange of the arm.

Referring to FIG. 13A, the superiorly facing sloped recesses 104 of the substantially annular member 38 each have a deep end 112 and a shallow end 114, with the shallow end having a depth less than the deep end, thereby defining a sloped configuration. The locking assembly further includes the ball 46 mounted within each superiorly facing sloped recess. As described above in connection with the housing, each recess 44 (FIG. 11C) in the housing holds a corresponding ball fixed relative to the substantially annular member which is rotatable relative to the housing about its central longitudinal axis. Referring to FIG. 4D, in the unlocked position (e.g., disengaged from the cooperating connection adapter) the substantially annular member begins with the deep end of each superiorly facing sloped recess abutting a corresponding ball. In operation as the substantially annular member rotates, the superiorly facing sloped recess moves relative to the ball so that when the arm completes its clockwise rotation (when viewed from a top plan view of the housing) relative to the housing, the shallow end of the superiorly facing sloped recess abuts the ball thereby moving the locking assembly in the inferior direction along the longitudinal axis of the housing and closer to the connection adapter (FIGS. 5B, 6B).

Referring to FIG. 13B, the recesses 106 about the inferior end 102 of the substantially annular member 38 are for receiving the balls 46, e.g., ball bearings. The balls are operable to reduce undesired friction that might otherwise be caused by rotation of the substantially annular member. Although FIG. 13B illustrates the substantially annular member as having five recesses, the substantially annular member can have 1, 2, 3, 4, 6, 7, 8, 9, 10, or any number of recesses suitable to reduce friction between the substantially annular member and the remainder of the locking assembly.

Referring to FIGS. 4D-5B and 14, the arm 36 extends laterally or radially outwardly from the substantially annular member 38. The arm includes a groove 120 and a flange 122. The groove of the arm matingly engages the larger rectangular portion 118 of the opening 110 of the substantially annular member 38 (FIGS. 13A, 13B). The flange of the arm matingly engages the smaller rectangular portion 116 of the substantially annular member. The arm can alternatively be configured with a dovetail groove configuration for engaging a cooperatively configured dovetail configuration on the substantially annular member.

Figure 15:
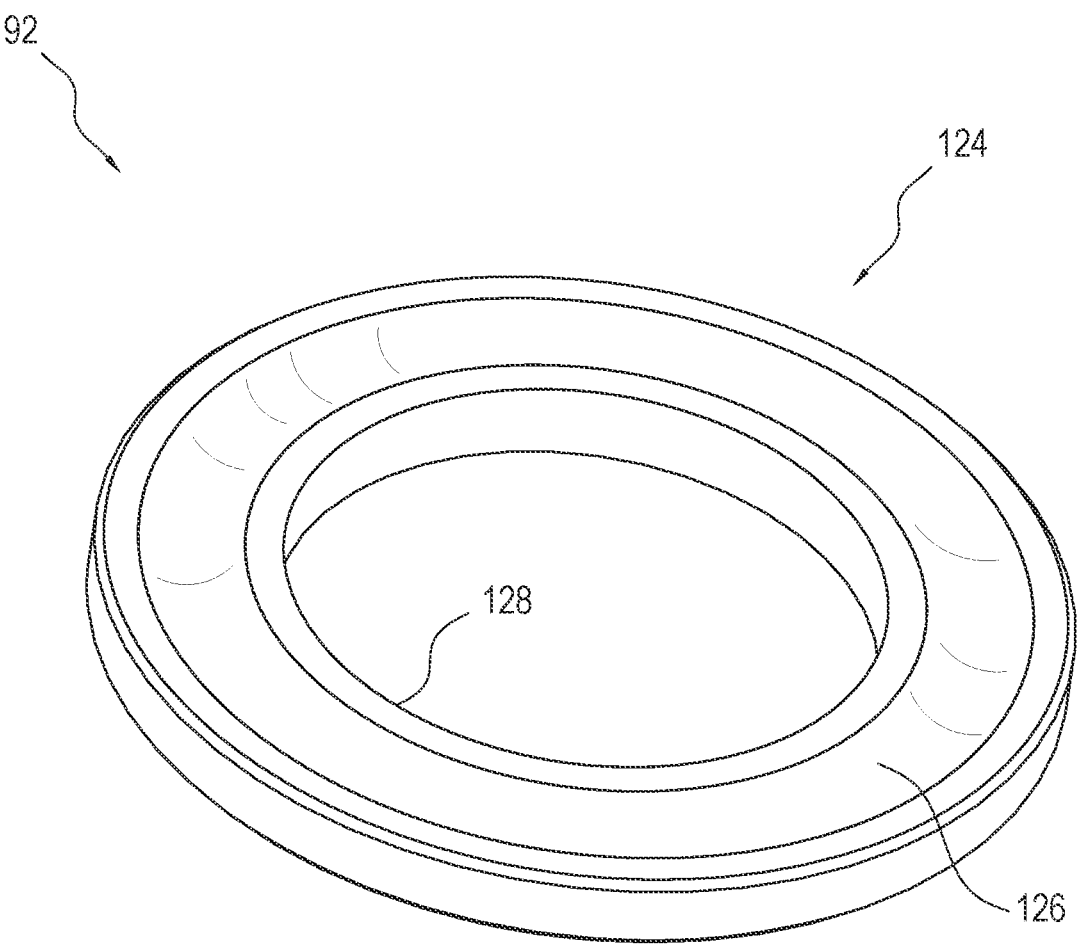
FIGS. 15-16 are perspective views of various plates of the quick connect of FIG. 1A.

Referring to FIGS. 3A-4C, the plate 92 of the locking assembly 24 engages and supports the balls 46 disposed about the inferior end of the substantially annular member 38. The plate can be an annular shim or a pressure plate. Referring to FIG. 15, the annular shim has a superior end 124. The annular shim includes an annular groove 126 defining a race about its superior end and a central through hole 128. The balls disposed about the inferior end of the substantially annular member 38 are mounted within the annular race.

Figure 17:
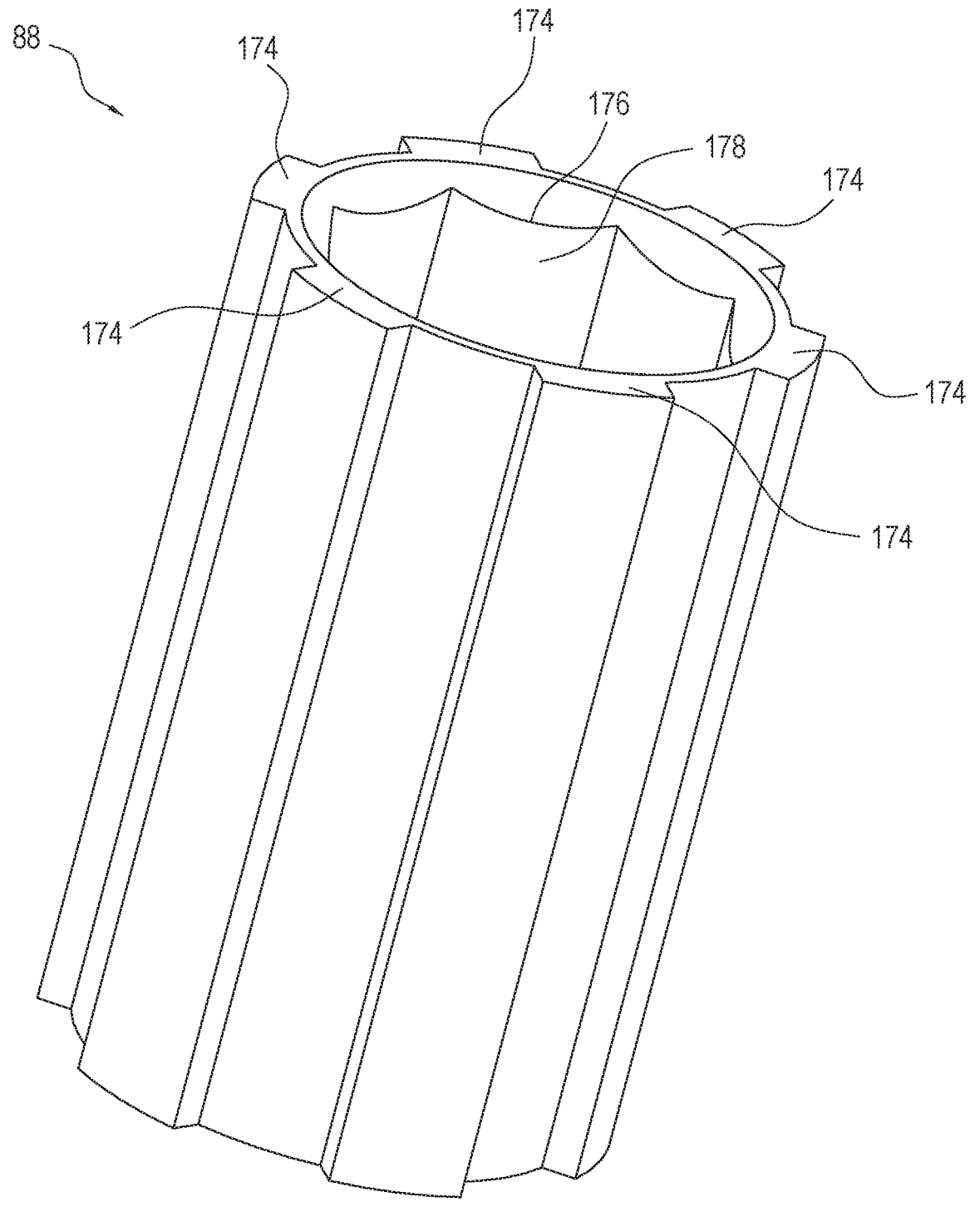
FIG. 17 is a perspective view of a sleeve of the quick connect of FIG. 1A.

The sleeve 88 of the locking assembly is configured as best shown in FIG. 17 and extends through the central through hole of the annular shim 92. The sleeve includes a central through hole 176 and a plurality of external splines 174 that extend longitudinally, substantially parallel to a central longitudinal axis of the sleeve. The external splines of the sleeve engage with various corresponding internal splines of the plates 90, 96, 98 of the locking assembly. The central through hole also includes internal planar side walls 178 for corresponding engagement or alignment with the planar wall segments of the connection adapter. In the present exemplary embodiment, the sleeve includes eight planar side walls forming an octagonal longitudinal cross-sectional shape.

Figure 8:
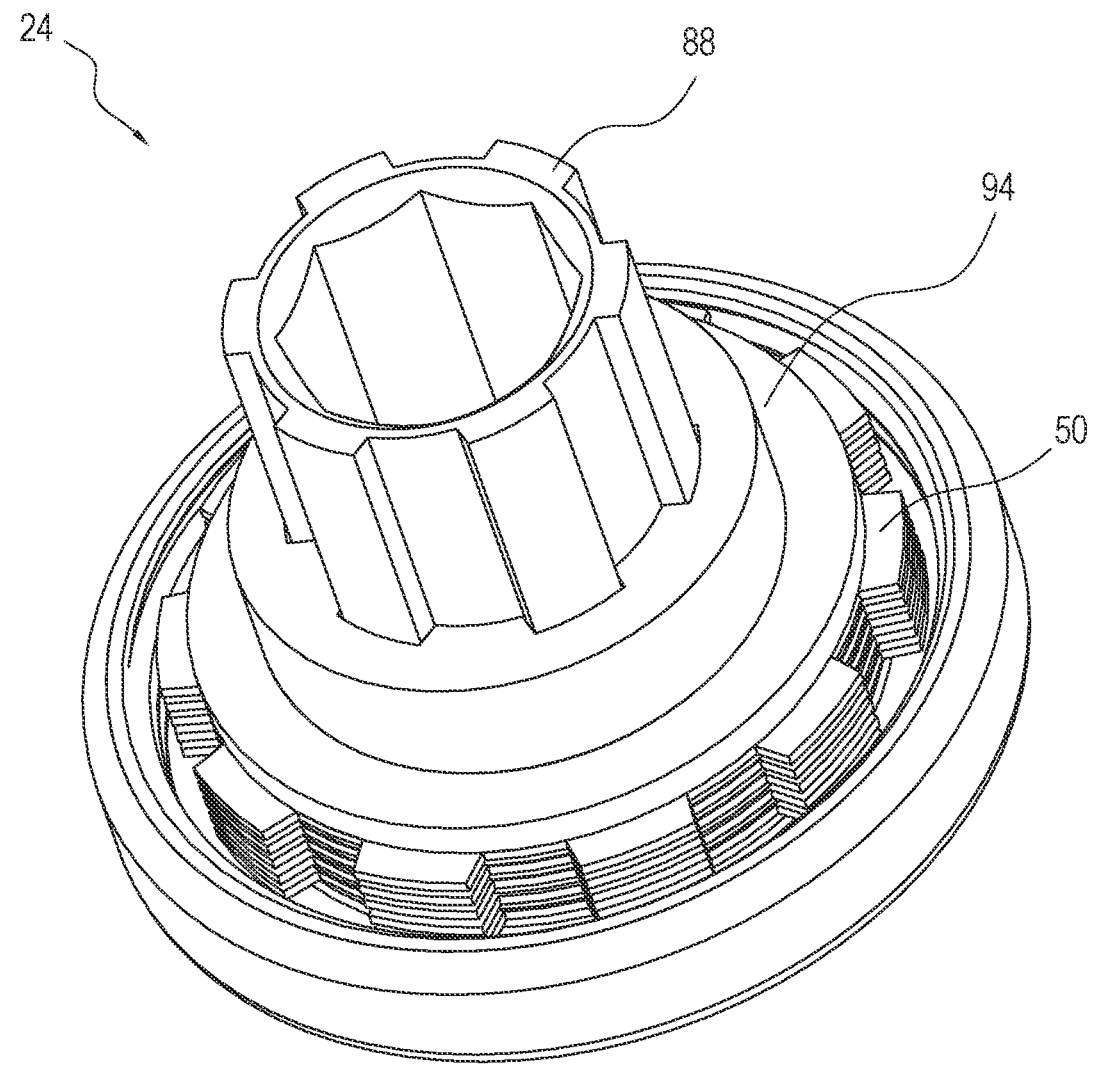
FIGS. 8-10 are various views of the quick connect of FIG. 1A with certain components omitted for purposes of illustration.
Figure 16:
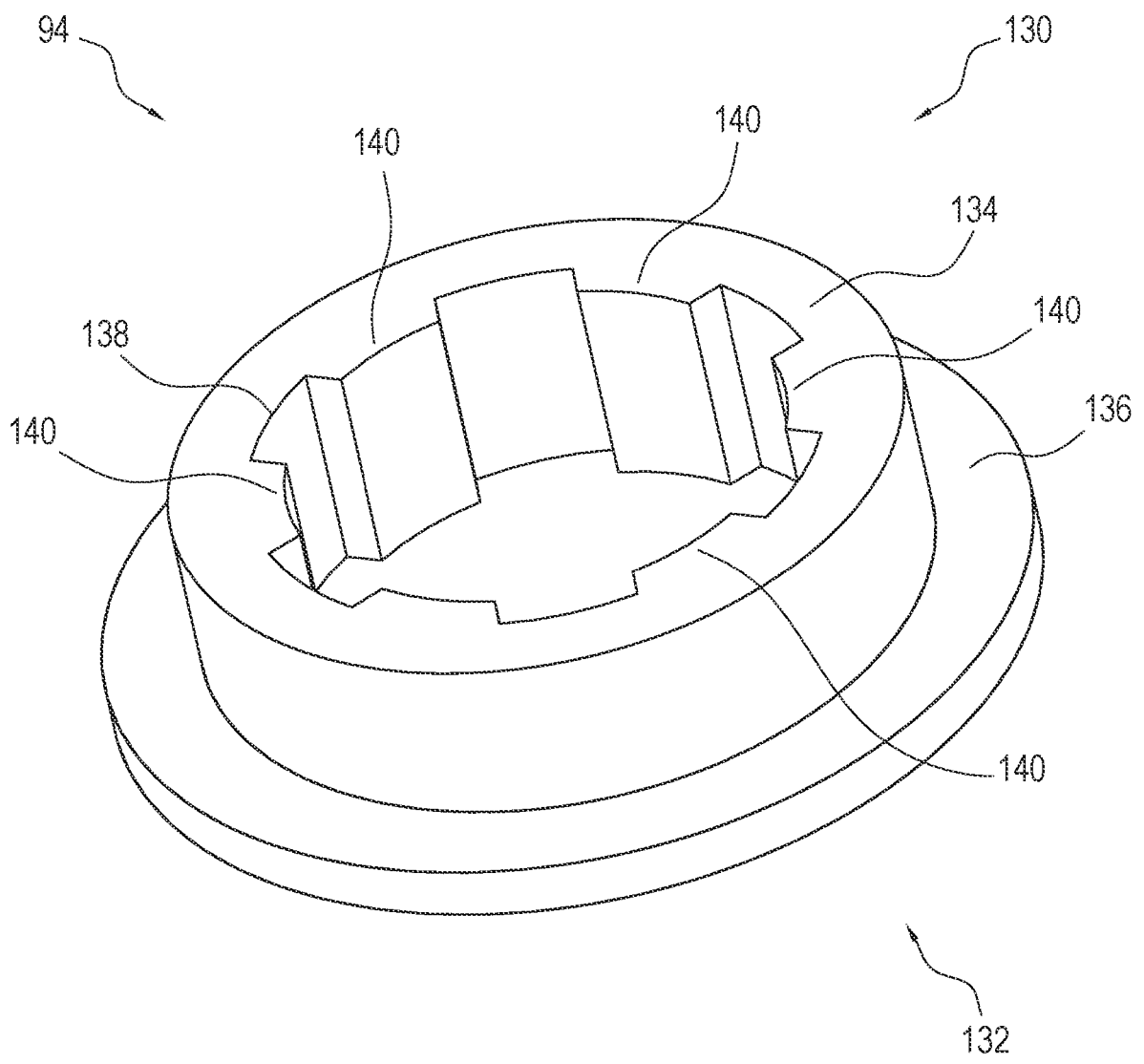

Referring to FIGS. 4C, 8, and 16, the plate 94 is configured as an annular flange and circumscribes the sleeve. The annular flange has a superior end 130 and an inferior end 132. The annular flange has an annular portion 134 about its superior end and a flange 136 extending from its inferior end. The annular flange has a central through hole 138 with a plurality of internal splines 140 complementary to the external splines 174 on the sleeve 88. That is, the internal splines of the annular flange matingly engage the external splines of the sleeve (FIG. 8).

Referring to FIGS. 3A, 3B, and 4C, a biasing member 142 circumscribes the annular portion 134 of the plate 94. The biasing member can be an annular leaf spring or the like. The biasing member biases the plate 92 superiorly relative to the housing 20 so as to keep the balls 46 mounted in the inferior recesses of the substantially annular member 38 engaged with the plate 92 and the housing.

Referring to FIGS. 3A, 3B, and 18A-18B, the plates 50, 96 of the locking assembly 24 are arranged in alternating fashion relative to one another. The plates 50, 96 are washer or clutch discs. The plates 50 have external splines 144 and a central through hole 146. The external splines 144 of the plates 50 engage the internal splines 48 (FIG. 11C) of the housing 20. The sleeve 88 of the locking assembly extends through the central through hole 146. The plates 96 have internal splines 148 and a central through hole 150. The internal splines 148 of the plates 96 engage external splines of the sleeve which extends through the central through hole 150. The plates 50, 96 are formed from differing materials. By way of example and not limitation, one set of plates 50 is formed from a suitably compressible material and the other set of plates 96 is formed from a suitably incompressible material. The plates 50 can be formed from a rigid polymer and the plates 96 can be formed from a metal. For example, the plates 50 can be formed from nylon, polyetherimide (such as Ultem), silicone, and the like. The plates 96 can be formed from stainless steel, anodized aluminum, and the like.

Referring to FIGS. 3A, 3B, 4C, 18A, and 18C, the plates 98 are arranged at a bottom end or below the plates 50, 96. The plates 98 are shim or washer discs. The shim discs are disposed toward a most inferior end of the locking assembly. The shim discs have a central through hole 154 and internal splines 152 complementary to the external splines 174 of the sleeve 88. The internal splines of the shim discs engage the external splines of the sleeve which extends through the central through hole.

Referring to FIGS. 3A, 3B, 4B, 4C, and 19, the plate 90 of the locking assembly 24 is disposed at a most inferior end of the quick connect 10. The plate extends beyond an inferior surface 29 of the housing 20. The plate has a larger diameter portion 160 about its superior end 156 and a smaller diameter portion 162 about its inferior end 158. The larger diameter portion has an annular body having internal splines 164 complementary shaped to the external splines 174 of the sleeve 88. The annular opening is sized to receive the sleeve therein. The smaller diameter portion has a central through hole 166. The smaller diameter portion of the plate is engageable with the flange of the connection adapter beyond the inferior surface of the housing. The central through hole is sized so as to be smaller than a through hole or overall diameter of the sleeve while still being adapted to receive the shaft of the connection adapter therethrough.

Figure 9:
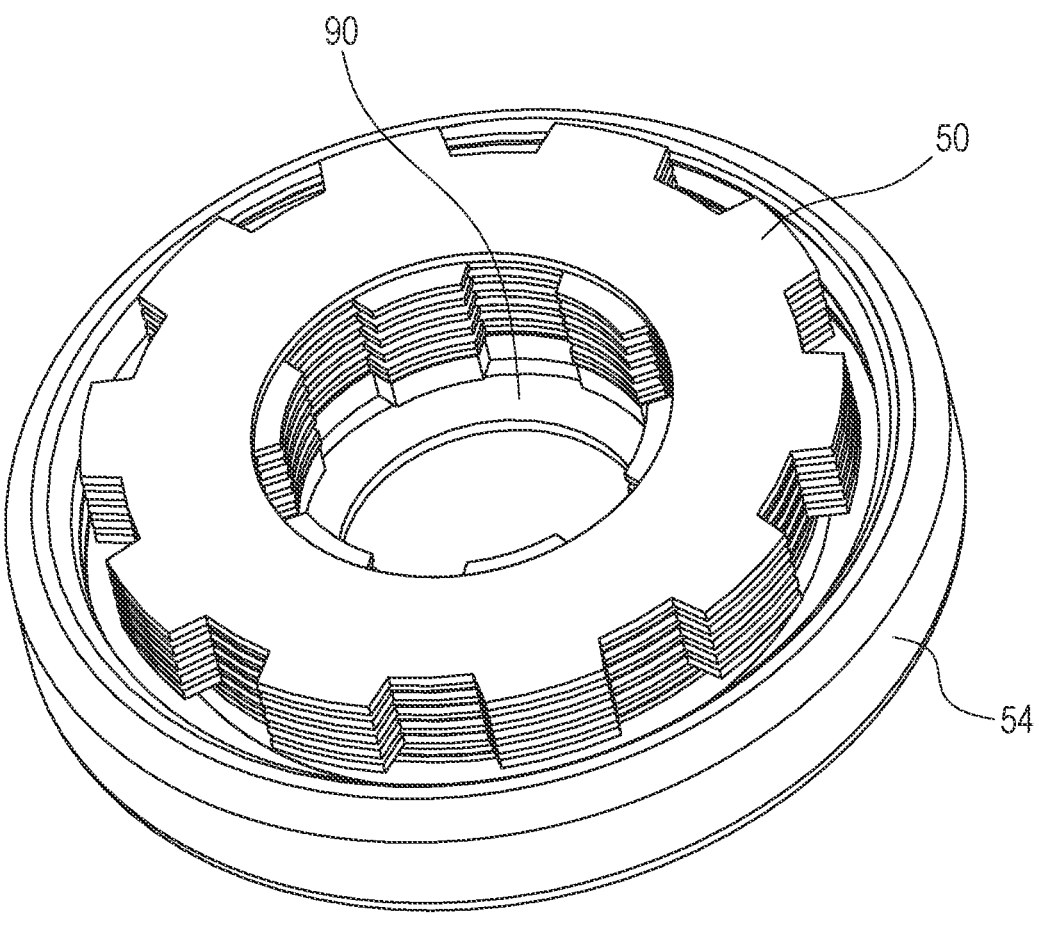
Figure 10:
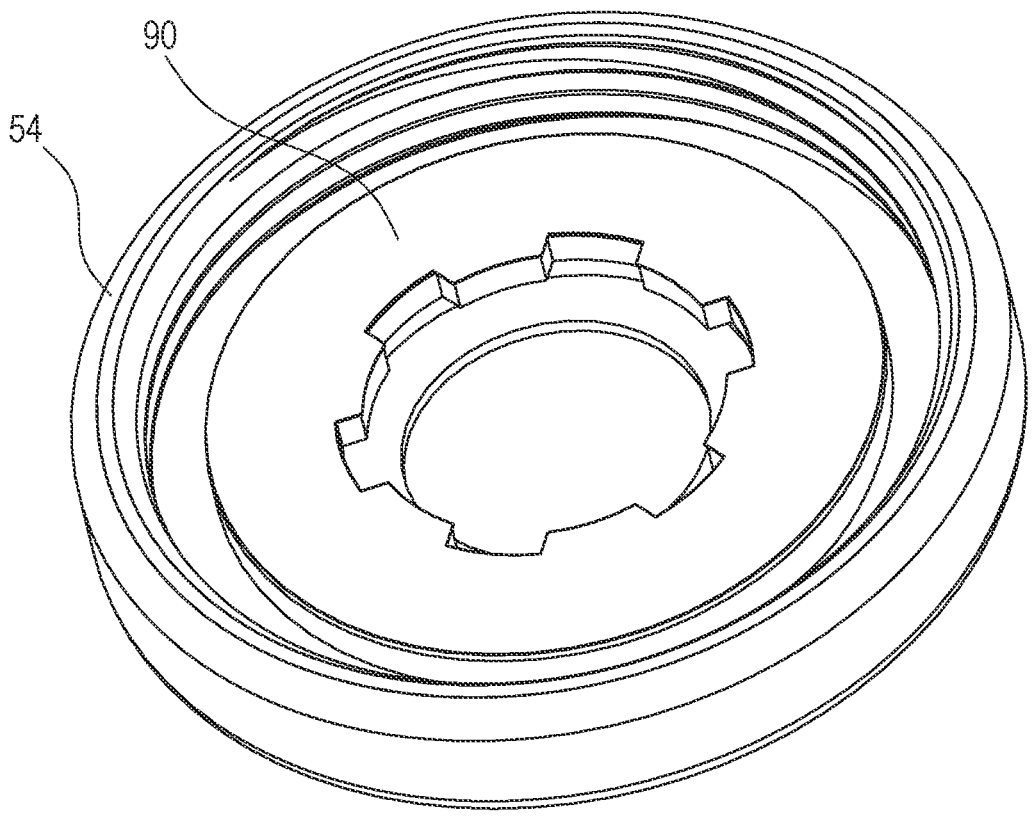
Figure 11A:
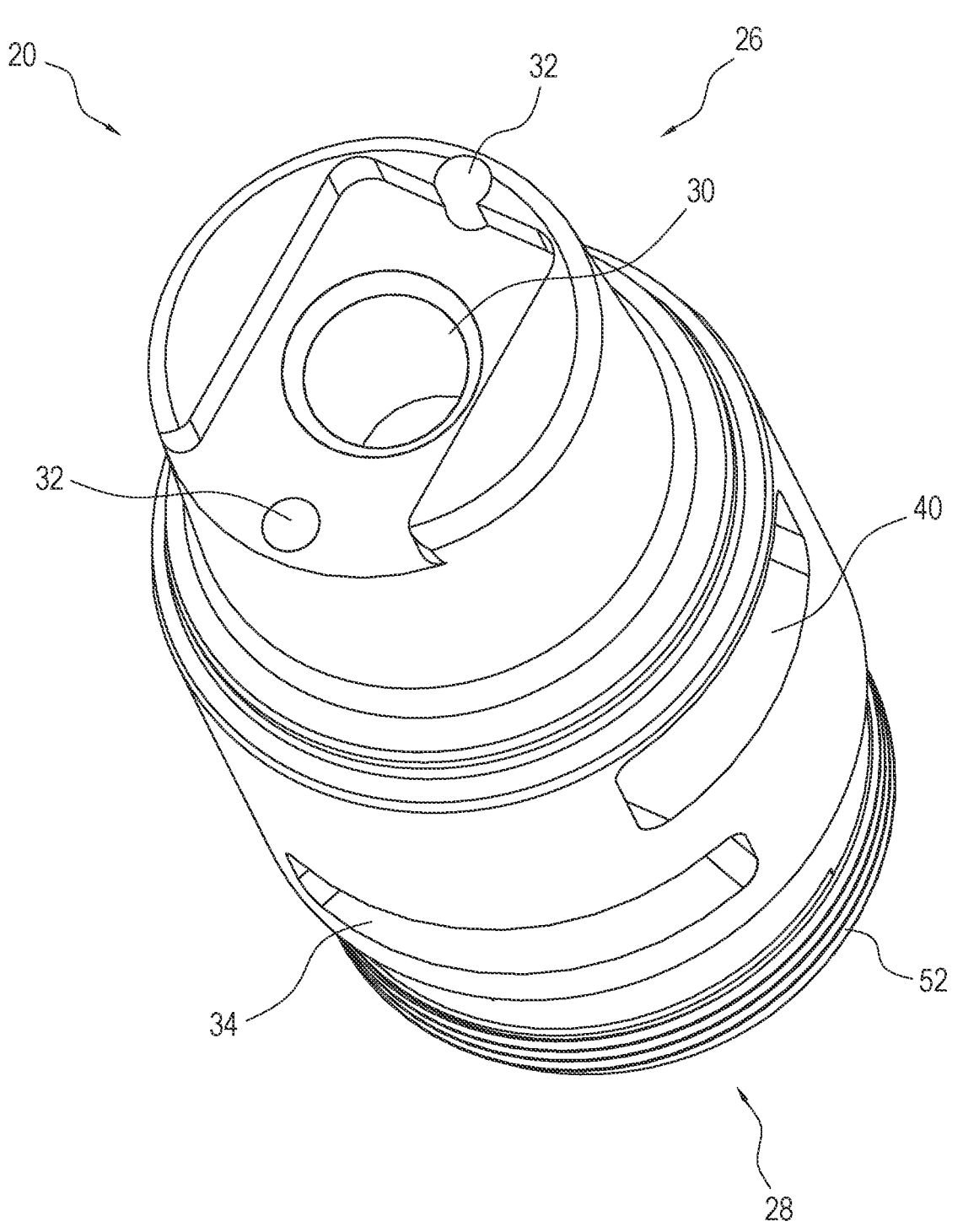
FIGS. 11A-11C are various views of a housing of the quick connect of FIG. 1A.
Figure 11B:
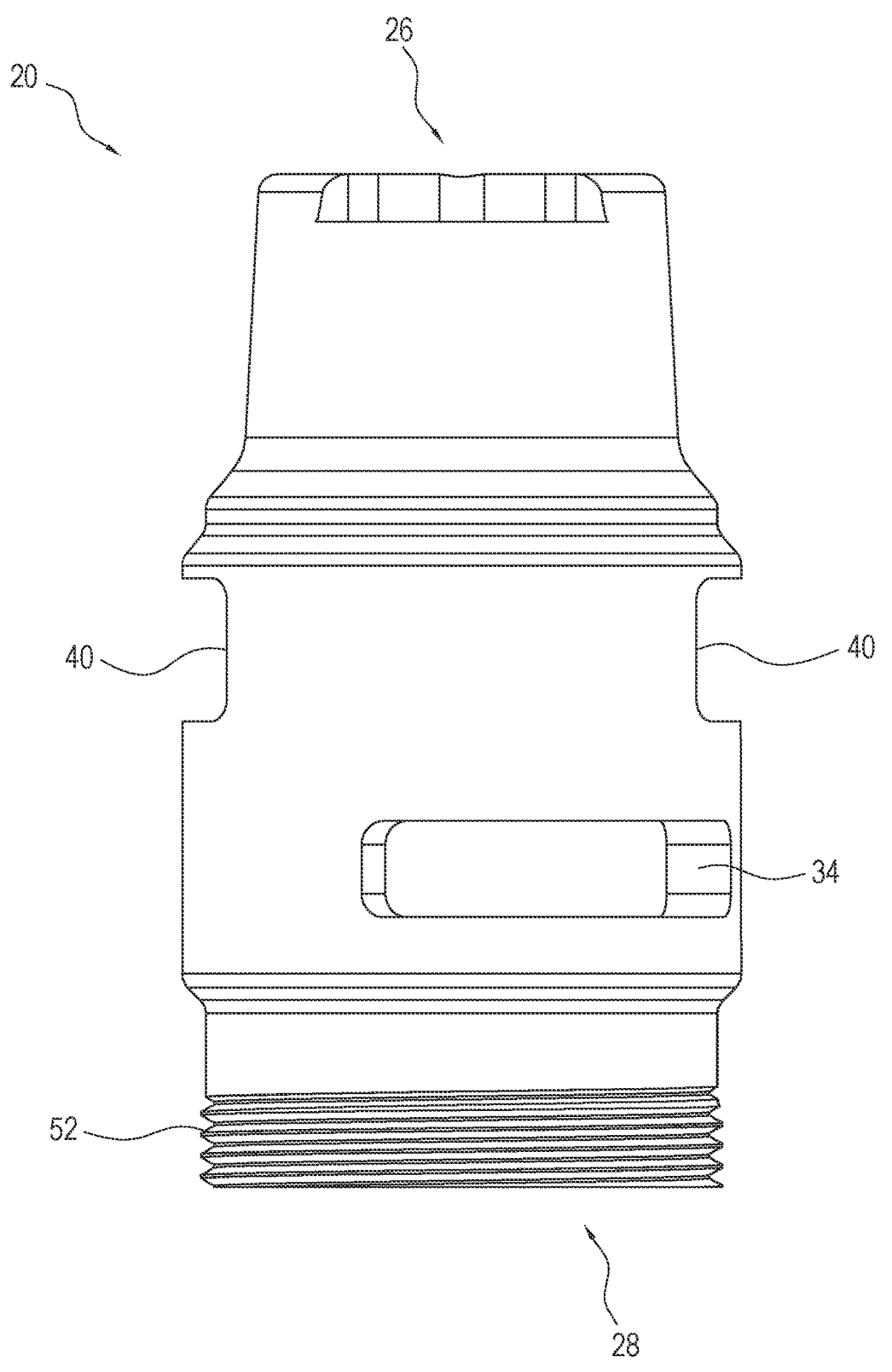
Figure 11C:
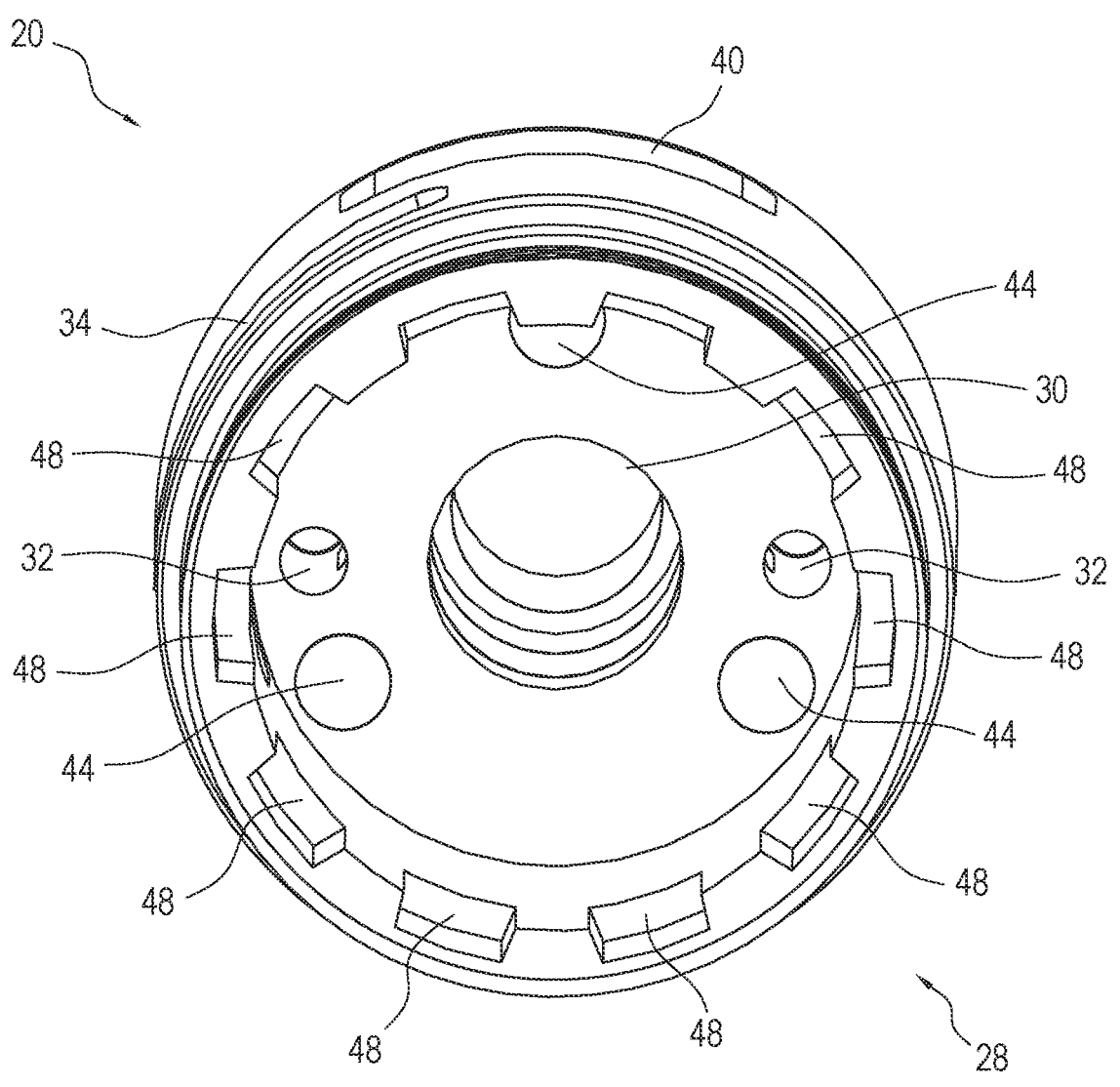
Figure 20:
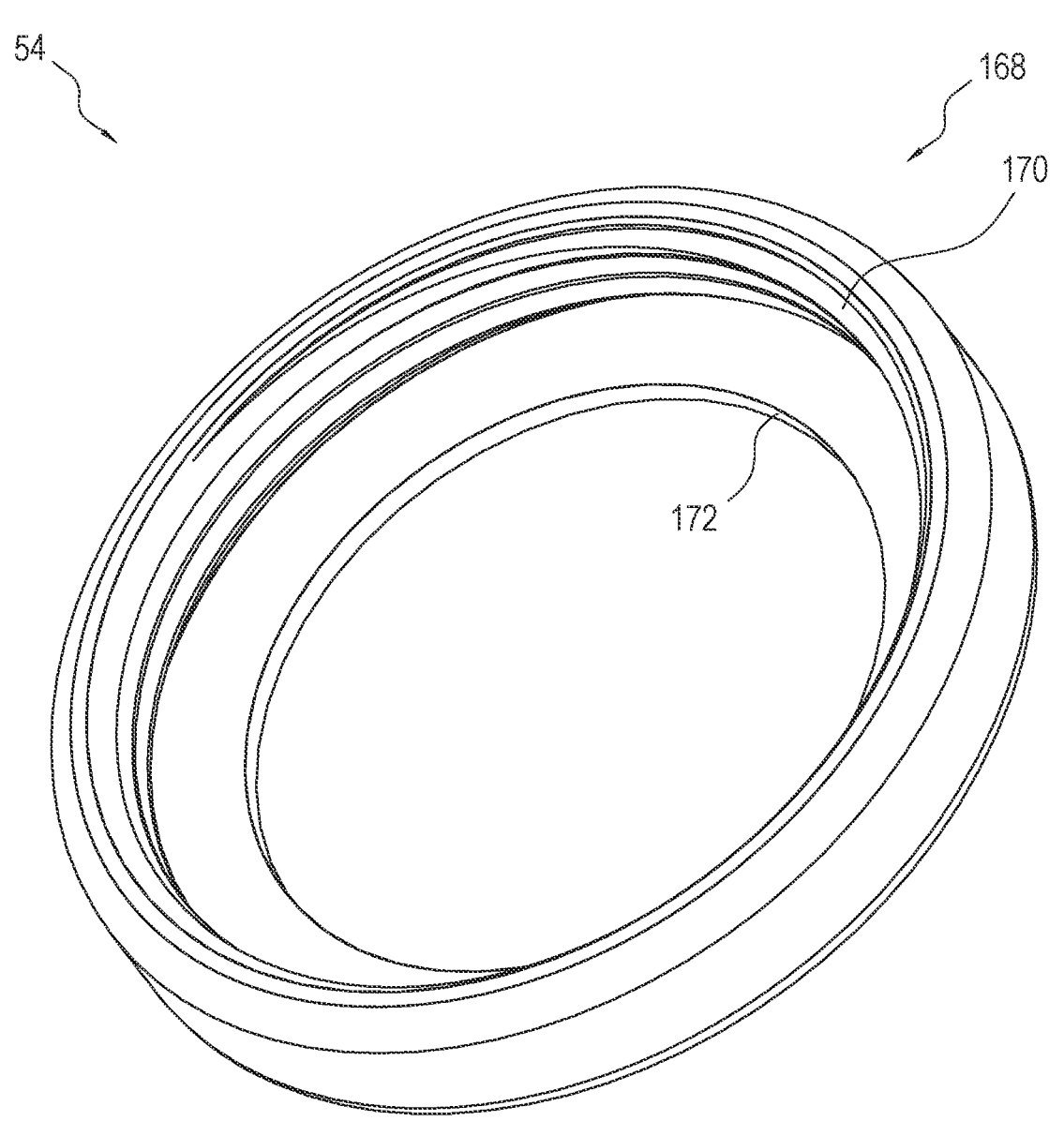
FIG. 20 is a perspective view of a base of the quick connect of FIG. 1A.

Referring to FIGS. 4C and 20, the base 54 of the quick connect 10 has internal threads 170 about its superior end 168 and a central through hole 172. The internal threads of the base engage the external threads of the housing 20. The central through hole 172 is sized so as to be smaller than an overall diameter of the larger diameter portion 160 of the plate 90 but larger than the smaller diameter portion 162 of the plate, to allow the smaller diameter portion to pass through. Referring to FIG. 9, the base and the central through hole are sized so as to be able to retain the plates 50, 96, 98 of the locking adapter inside the housing while also allowing a portion of the plate 90 to pass through and extend beyond a most inferior end of the housing.

FIGS. 21-31 illustrate another exemplary embodiment of a quick connect 210 in accordance with the subject disclosure. This exemplary embodiment of the quick connect includes various features substantially as disclosed for the above embodiment, for example, the cooperating connection adapter and the slide locking mechanism.

Figure 21:
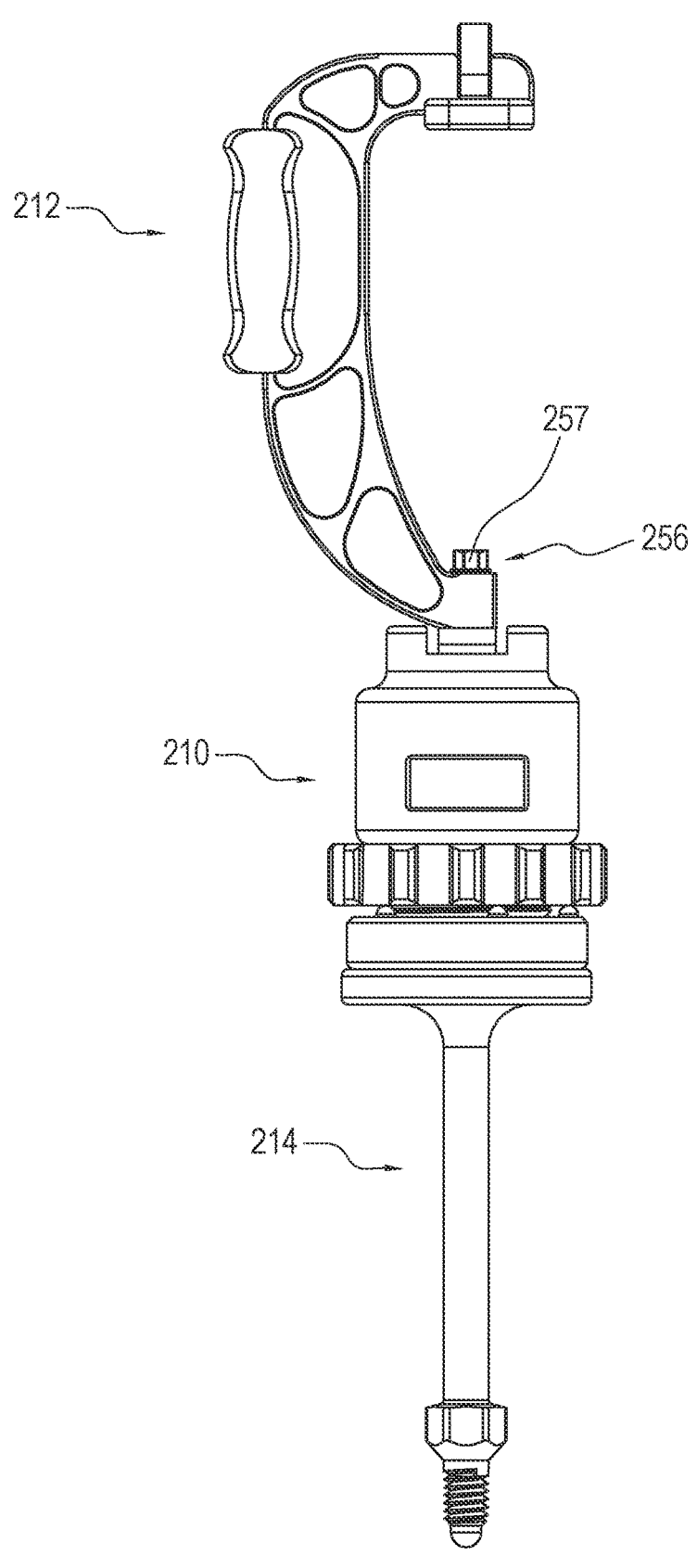
FIG. 21 is a right side view of an exemplary quick connect in accordance with another exemplary embodiment of the subject disclosure.

Referring to FIG. 21, the quick connect 210 is cooperatively engageable with a connection adapter 214. The quick connect also includes a fastener 256 for connecting a secondary device thereto, e.g., a C-frame extractor 212, as generally configured as discussed above for the C-frame device 12.

Figure 23A:
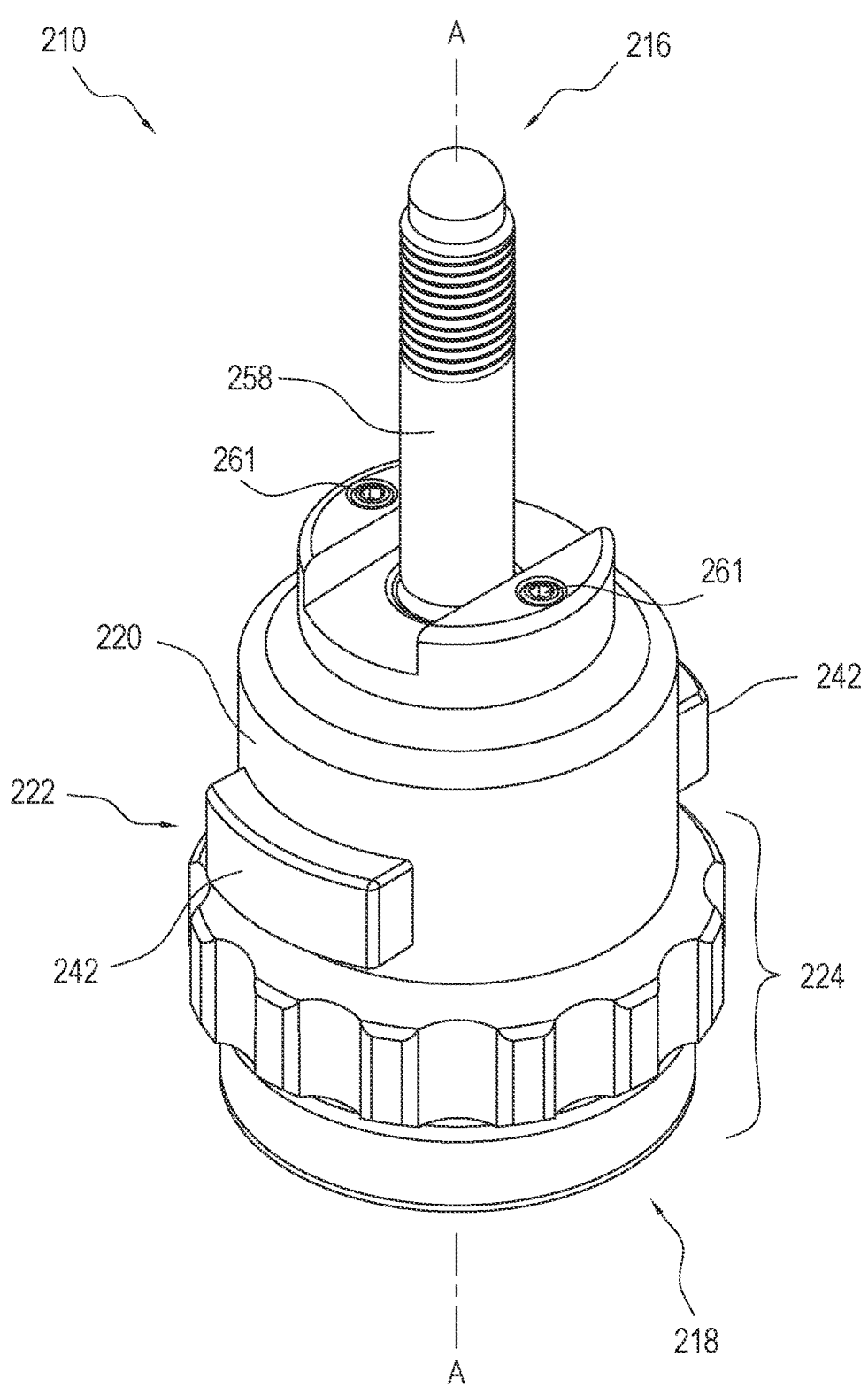
FIGS. 23A-23E are various views of the quick connect of FIG. 21 in a locked or disengaged state with certain components omitted and/or in phantom for purposes of illustration.
Figure 23B:
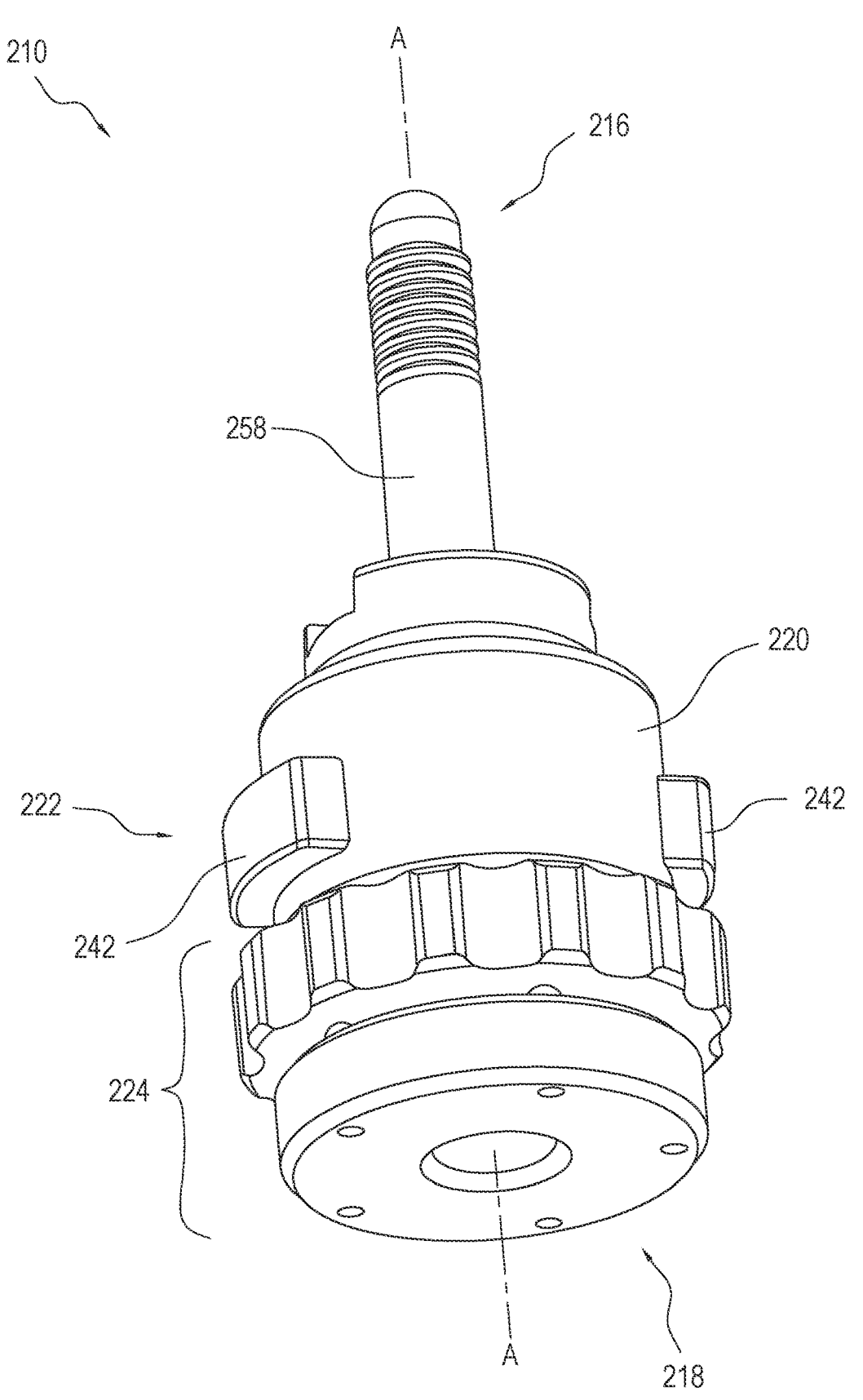

Referring to FIGS. 23A-23B, the quick connect 210 has a superior end 216 and an inferior end 218. The quick connect includes a housing 220, a slide locking mechanism 222 mounted within the housing, and a collar assembly 224.

Figure 27A:
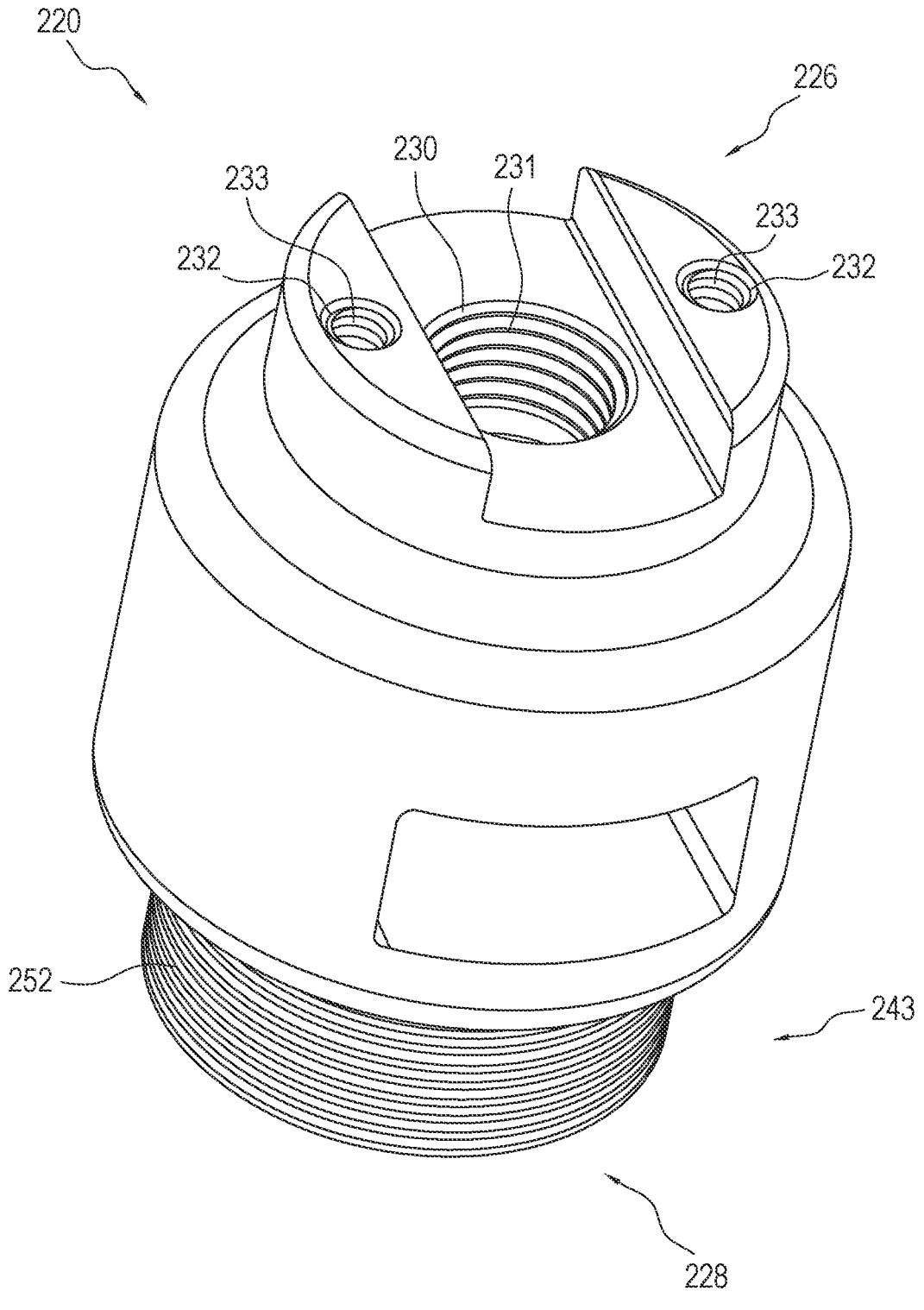
FIGS. 27A-27B are various views of a housing of the quick connect of FIG. 21, FIGS. 28A-28C are various views of a slide locking mechanism of the quick connect of FIG. 21.
Figure 27B:
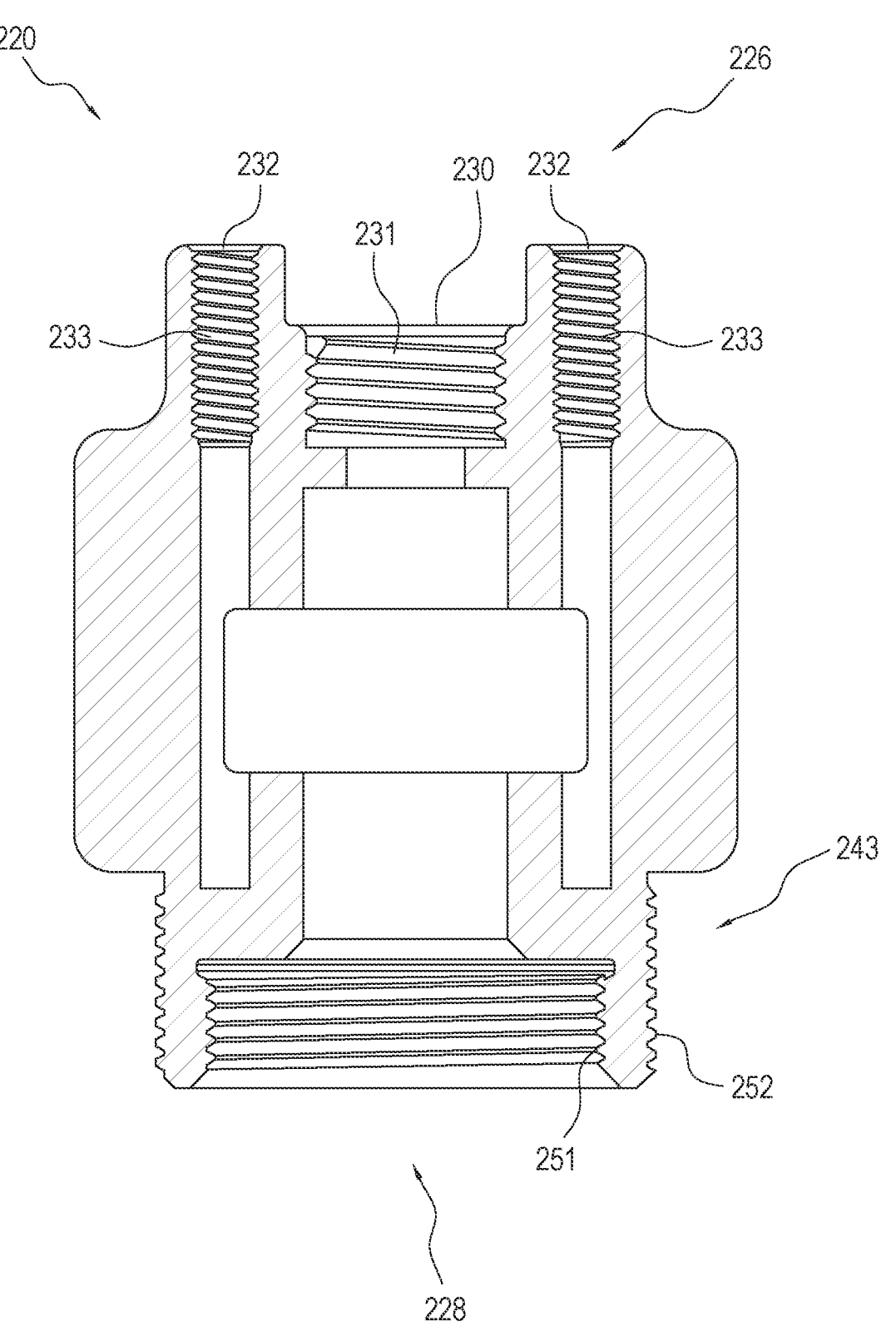

Referring to FIGS. 27A-27B, the housing 220 has a superior end 226 and an inferior end 228. The housing includes a central through hole 230 and one or more through holes 232 laterally spaced from the central through hole. The housing also includes a reduced diameter portion 243 about its inferior end.

The central through hole 230 of the housing 220 is structured for receiving the fastener 256. For example, the central through hole is configured with internal threads 231. Referring to FIGS. 21 and 23A-23E, the fastener includes a shaft 258 that is received and secured within the central through hole, along with a nut 257 for fastening the secondary device 212 thereto. The internal threads of the central through hole engage with external threads about an inferior end of the shaft. The fastener connects to the housing such that the secondary device extends superiorly from the housing.

Referring to FIGS. 23A-23E and 27A-27B, the through holes 232 of the housing 220 are arranged on opposing lateral sides of and laterally spaced from the central through hole. Each through hole includes internal threads 233 and is adapted to receive a pin 259 that operates to limit the lateral movement (e.g., travel) of each lock button 242 of the slide locking mechanism 222, as described in further detail below. The internal threads of each through hole are engageable with external threads of a plug 261 that is configured to retain the pins inside the housing.

Figure 23C:
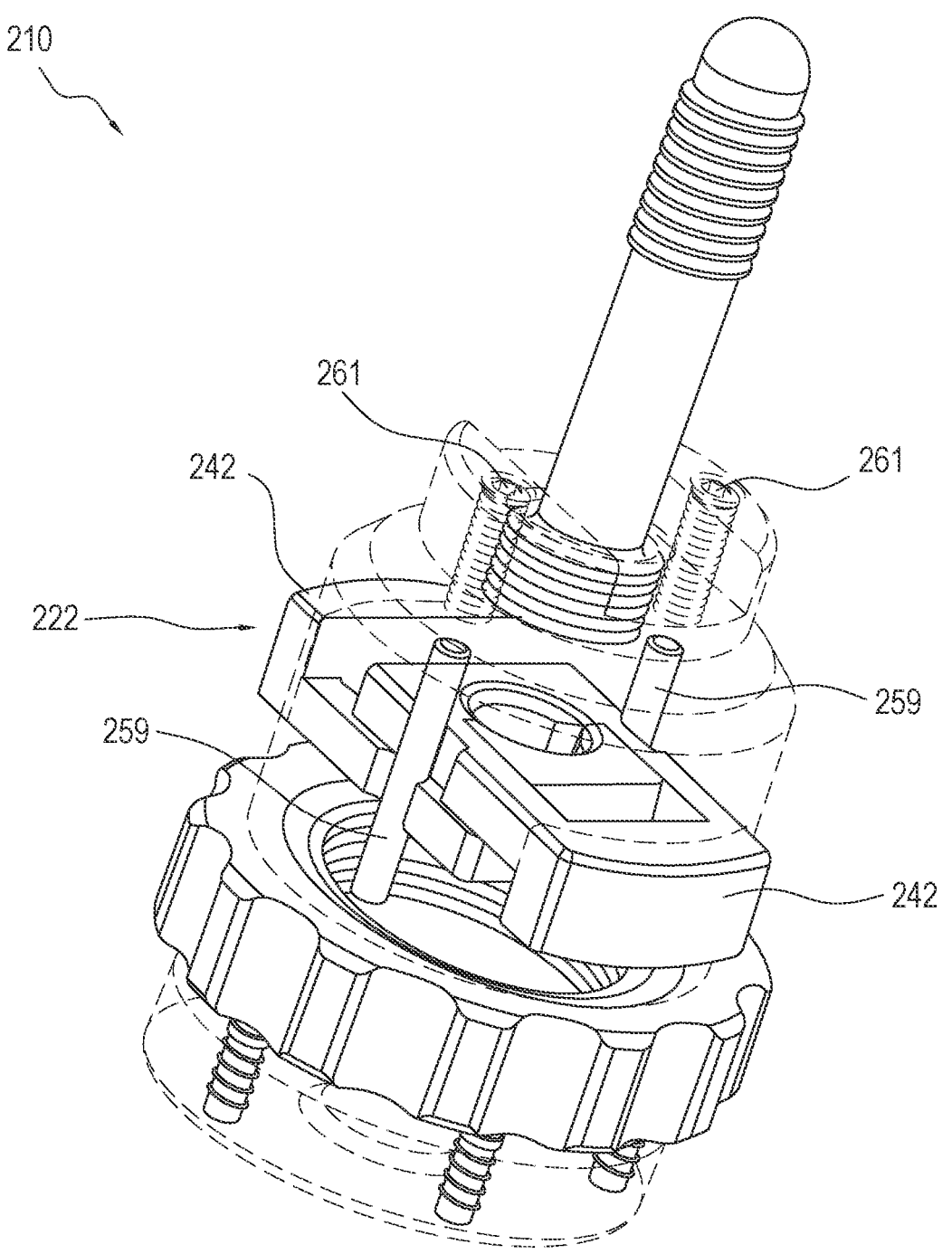
Figure 23D:
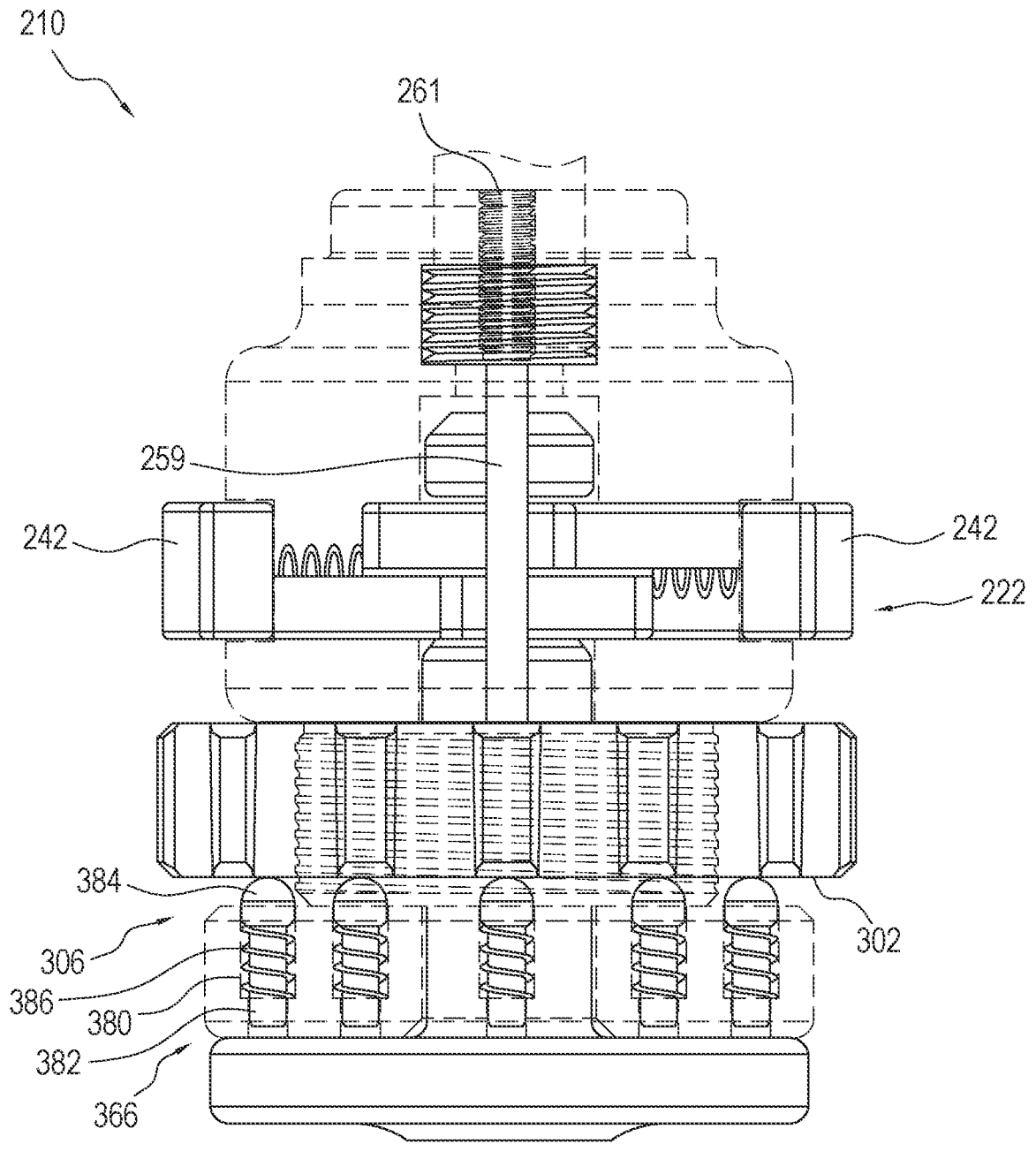
Figure 23E:
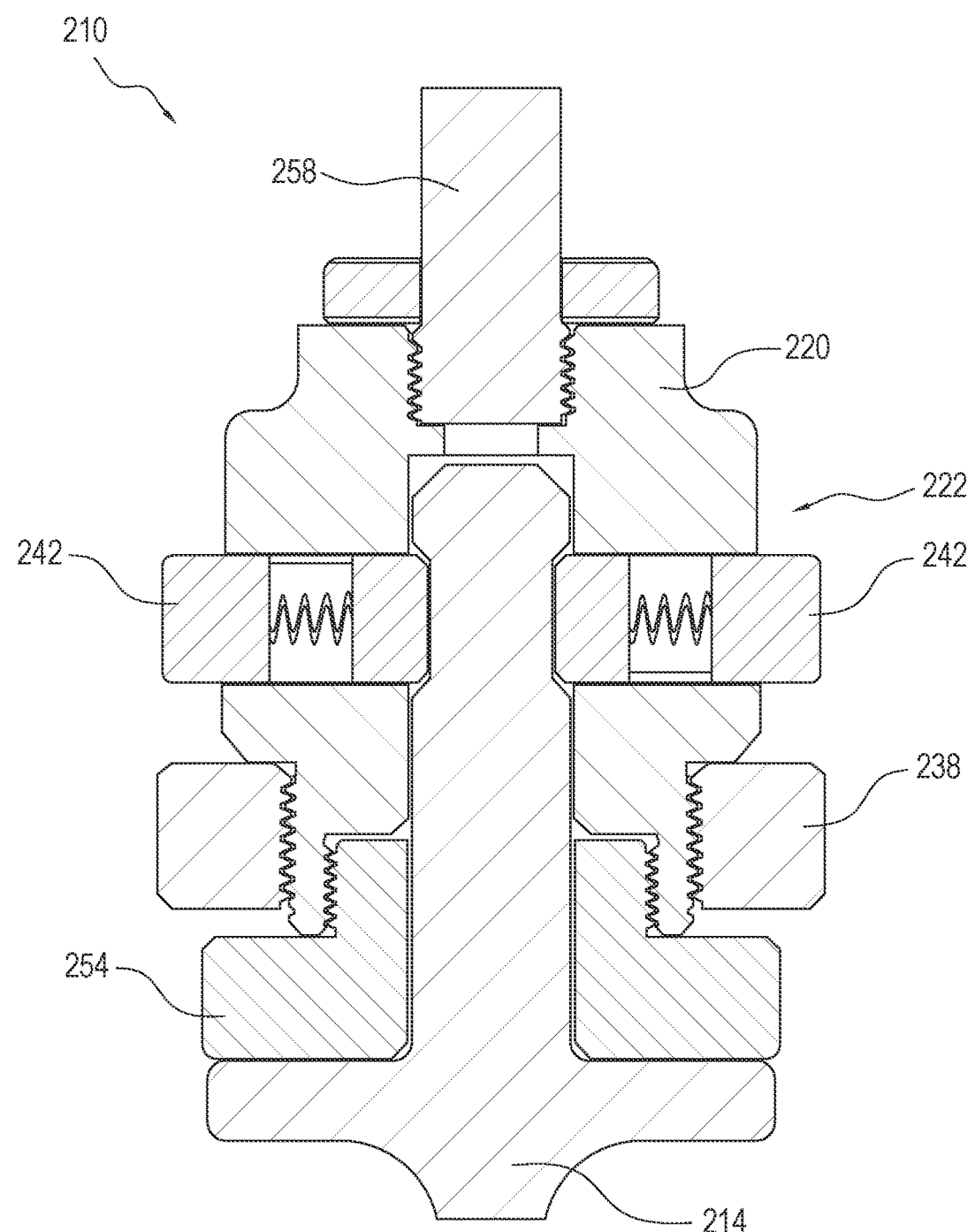

Referring to FIGS. 23E, 27A, and 27B, the reduced diameter portion 243 of the housing 220 has internal threads 251 and external threads 252. The internal threads of the reduced diameter portion are engageable with a base of the quick connect. The external threads of the reduced diameter portion are engageable with a collar lock of the collar assembly.

Figure 28A:
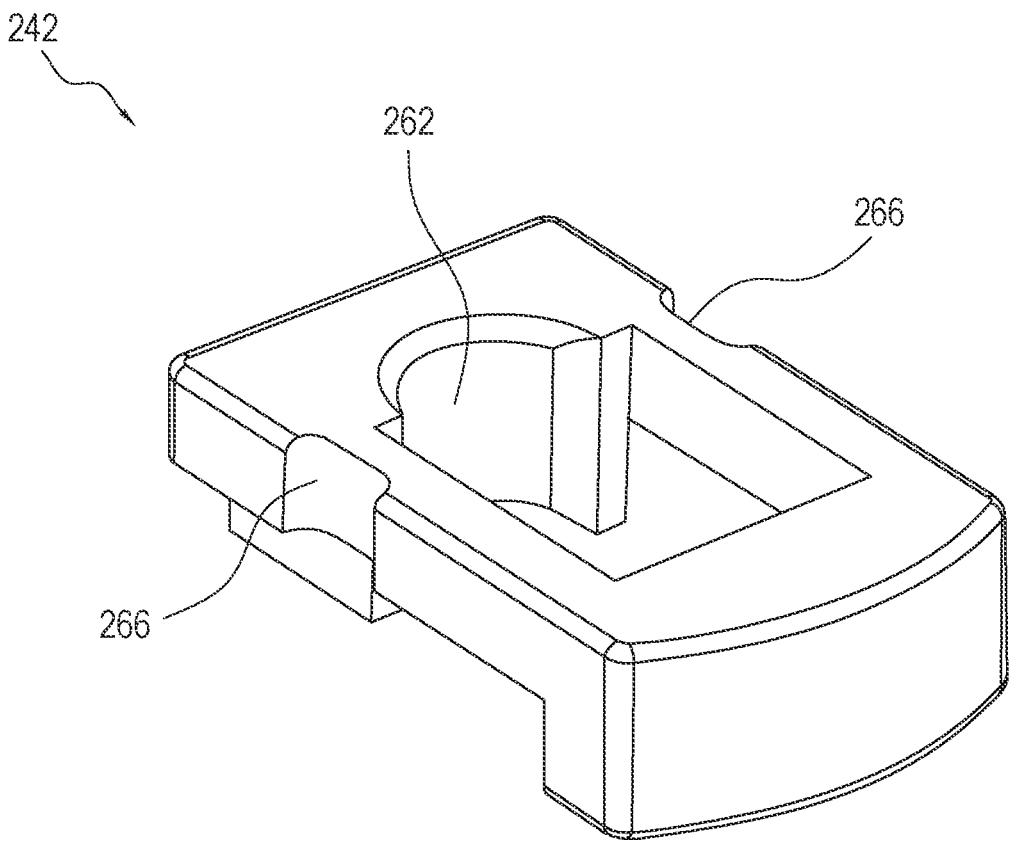
Figure 28B:
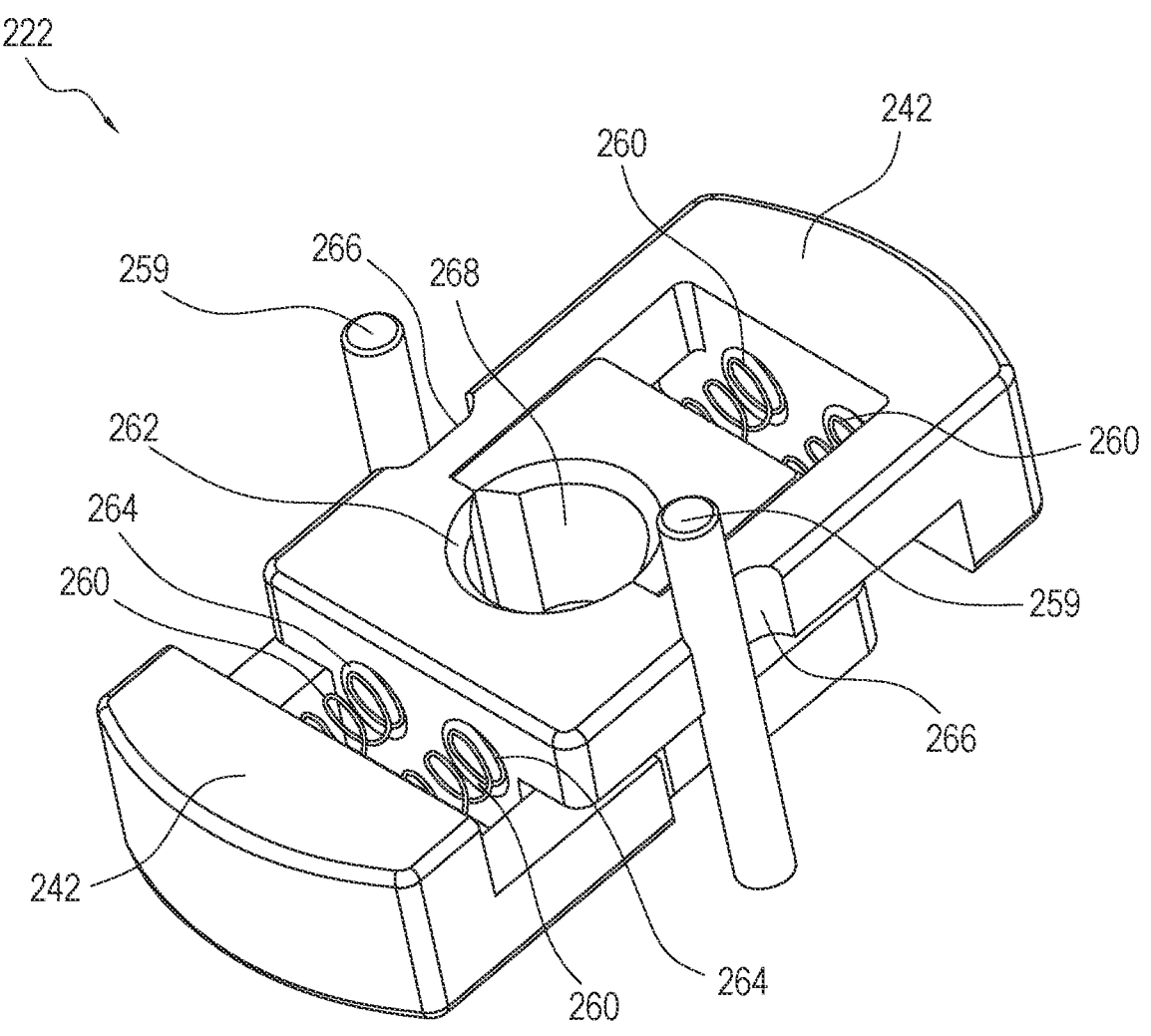
Figure 28C:
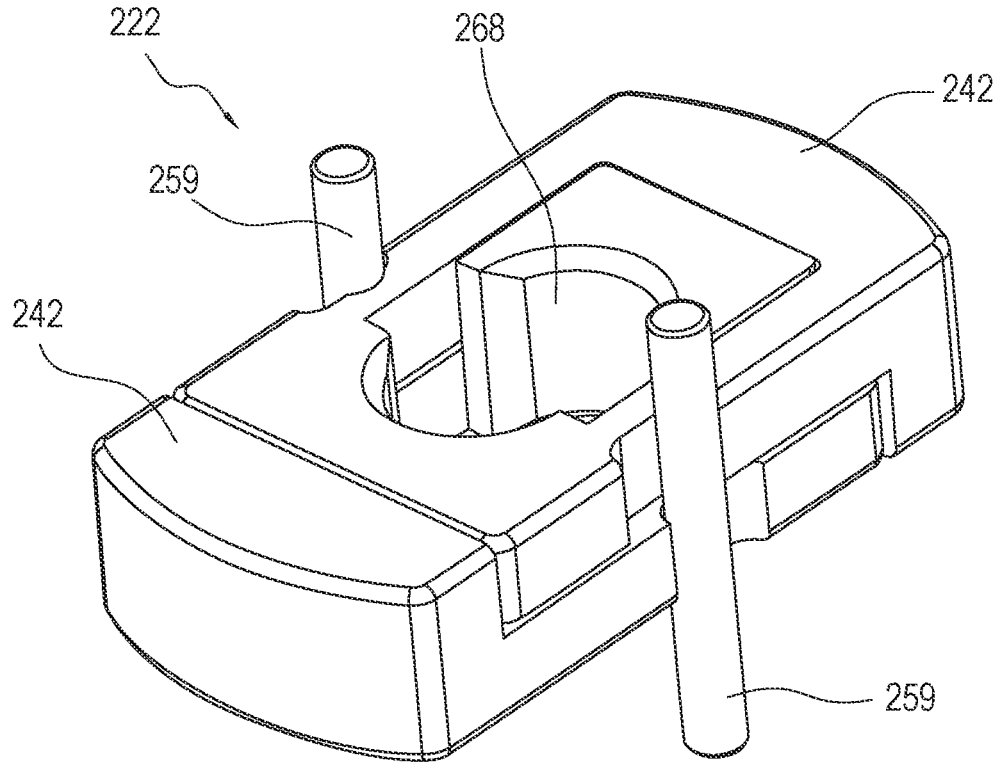

Referring to FIGS. 23A-23E, 26A-26C, and 28A-28C, the slide locking mechanism 222 of the quick connect 210 is mounted within the housing 220 for receiving the connection adapter. The slide locking mechanism includes one or more lock buttons 242, one or more pins 259, and one or more biasing members 260, and is generally configured as discussed above for the slide lock 22. The slide locking mechanism extends between opposing lateral sides of the housing. The slide locking mechanism is movable from a locked position (FIG. 28B) to an unlocked position (FIG. 28C). In the locked position the lock buttons extend between opposing lateral sides of the housing once the quick connect is connected to the connection adapter. In the unlocked position the user depresses each lock button inwardly which operates to release the quick connect from the connection adapter.

Referring to FIG. 28B, the lock buttons 242 of the slide lock each have a clamping face 262, one or more blind holes 264, and one or more recesses 266. One of the lock buttons can be a first clamping portion and the other lock button can be a second clamping portion. The first and second clamping portions are movable relative to each other. When the slide lock is in the locked position, the clamping faces of the cooperating lock buttons are adapted to define a central through hole 268. Referring to FIG. 23E, the central through hole of the slide lock is operable to receive the connection adapter 214, as described in further detail below. When the slide lock is transitioning from the locked position (FIG. 28B) to the unlocked position (FIG. 28C), the lock buttons move relative to one another, thereby enlarging the size of the central through hole or the spacing between the first and second clamping portions in the unlocked position so as to release the connection adapter or allow the connection adapter to pass through. The structure of the slide locking mechanism 222 and the pins 259 are the same as discussed above for the slide lock 22 and the pins 59.

Figure 22:
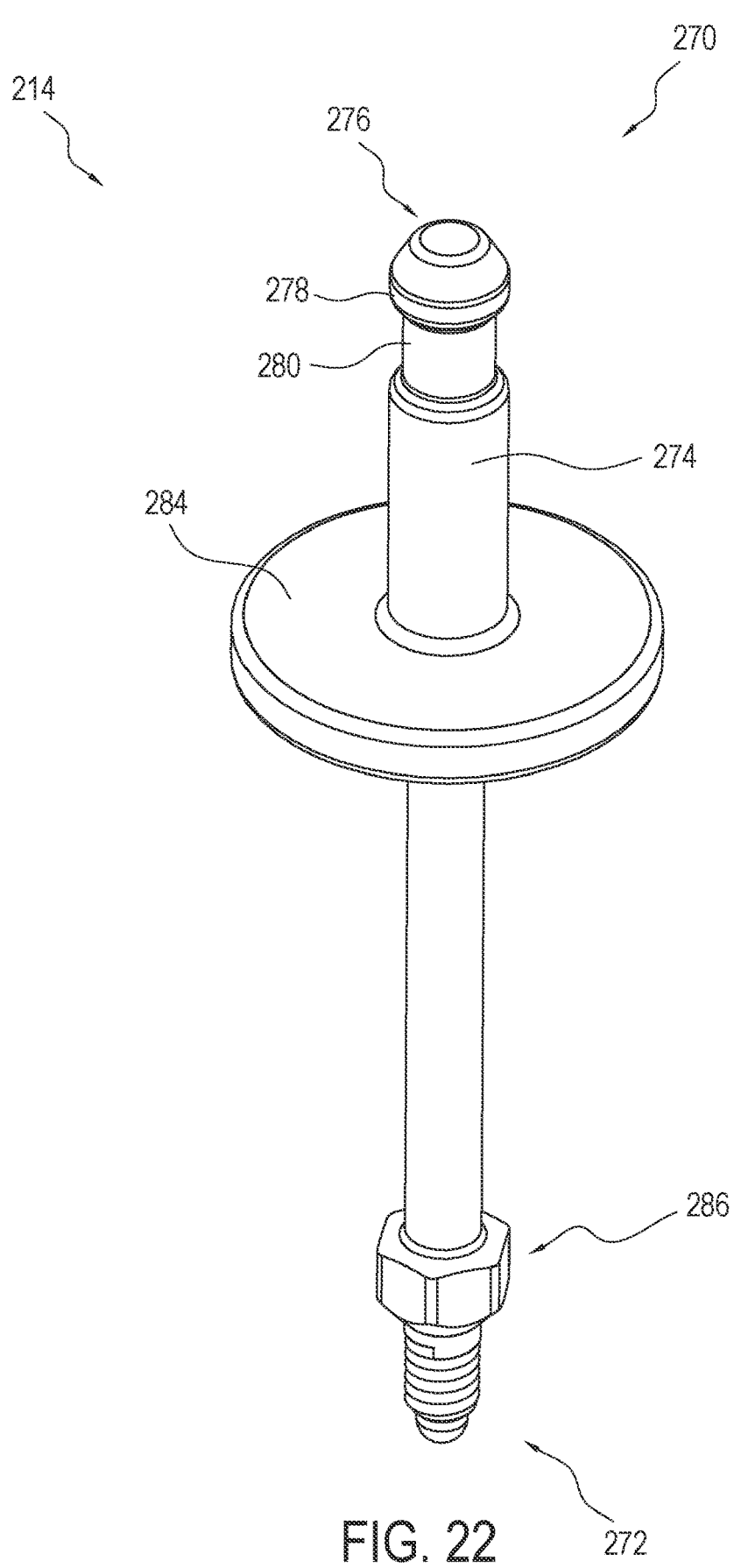
FIG. 22 is a perspective view of a connection adapter for cooperating engagement with the quick connect of FIG. 21.

Referring to FIG. 22, the connection adapter 214 has a superior end 270 and an inferior end 272, and is configured similarly as discussed above for the cooperating connection adapter 14. The connection adapter is referred to as a connection rod. The connection adapter includes a shaft 274 having a head that includes a substantially conical end 276 with a cylindrical base 278 about its superior end, and a reduced diameter portion 280. The connection adapter also includes a flange 284 adjacent its superior end. The connection adapter also includes a fastener 286 about its inferior end. The fastener allows the connection adapter to connect to a medical tool for extraction, such as a surgical implant extractor.

The substantially conical end 276 of the connection adapter can be a frustoconical end. The tapered end of the substantially conical end 276 is operable to push or drive the lock buttons of the slide lock outwardly upon insertion of the connection adapter 214 into the quick connect. Referring to FIGS. 23D and 23E, the cylindrical base 278 and the reduced diameter portion 280 of the connection adapter are operable in combination with the slide lock to keep the quick connect connected to the connection adapter.

The shaft 274 of the connection adapter is inserted and received in the central through hole of the base 254. Upon being fully inserted and engaged with the quick connect, the flange 284 is positioned adjacent the base.

Referring to FIGS. 23A-23B, the collar assembly 224 of the quick connect 210 circumscribes the housing 220. The collar assembly includes a collar lock 238 and a base 254. The collar assembly engages the housing to the connection adapter. Specifically, the collar assembly is movable along a longitudinal axis A of the housing 220 upon rotation of the collar lock via the internal threads 312.

Figure 29:
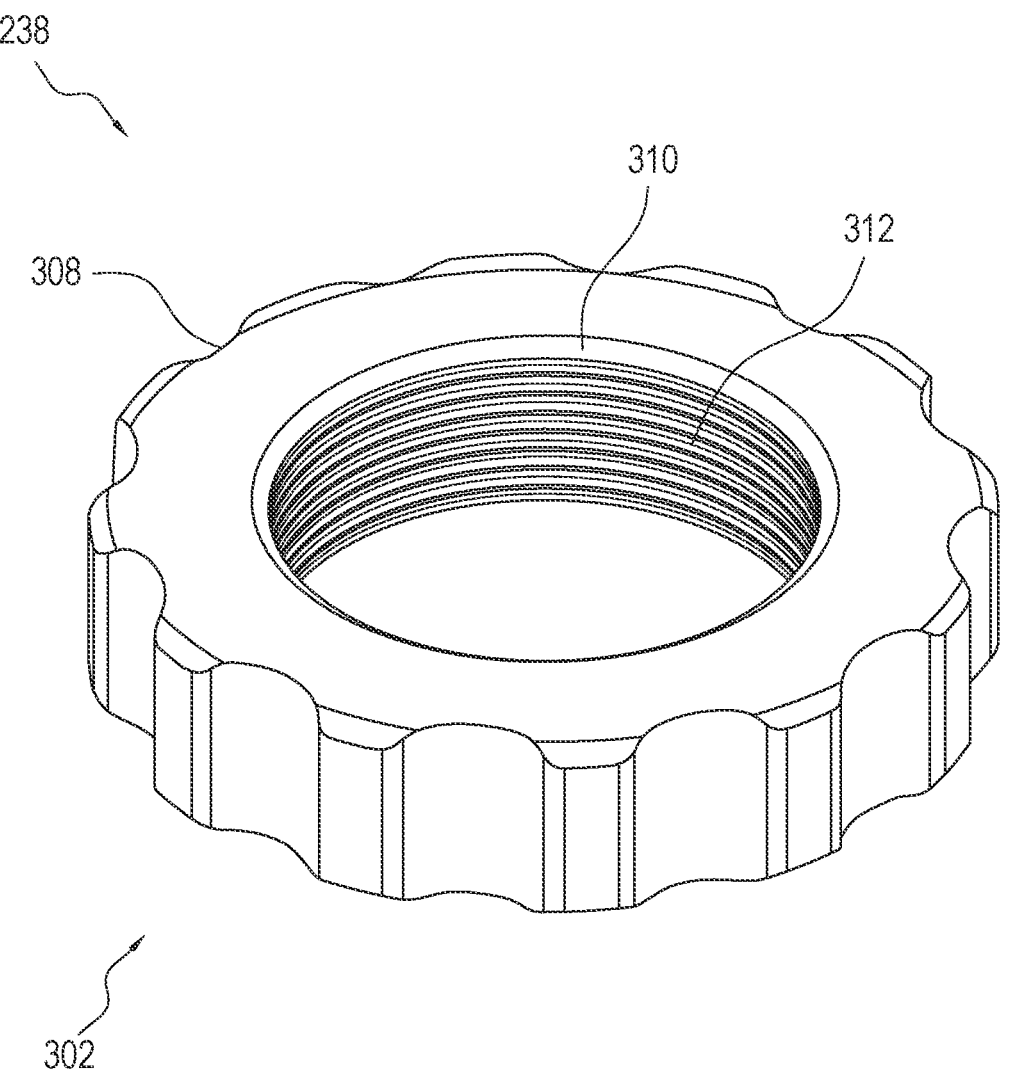
FIG. 29 is a perspective view of a collar lock of the quick connect of FIG. 21.

Referring to FIG. 29, the collar lock 238 of the collar assembly engages the housing. The collar lock has a substantially annular body with a central through hole 310 having internal threads 312 that engage the external threads of the housing. The collar lock is movable along a longitudinal axis A of the housing upon rotation of the collar lock relative to the housing. The collar lock has an inferior surface 302. The inferior surface abuts a biasing device 306 of the base (FIG. 23D) upon rotating or twisting the collar lock about the longitudinal axis of the housing downwardly. That is, the collar lock moves inferiorly along the longitudinal axis of the housing and imparts an inferiorly directed force on the biasing device. The collar lock also includes scalloped edges or scalloped external walls 308. The scalloped edges are concave edges and adapted to facilitate rotating or twisting the collar lock about the longitudinal axis of the housing so as to move the collar lock in the inferior-superior directions.

Figure 30:
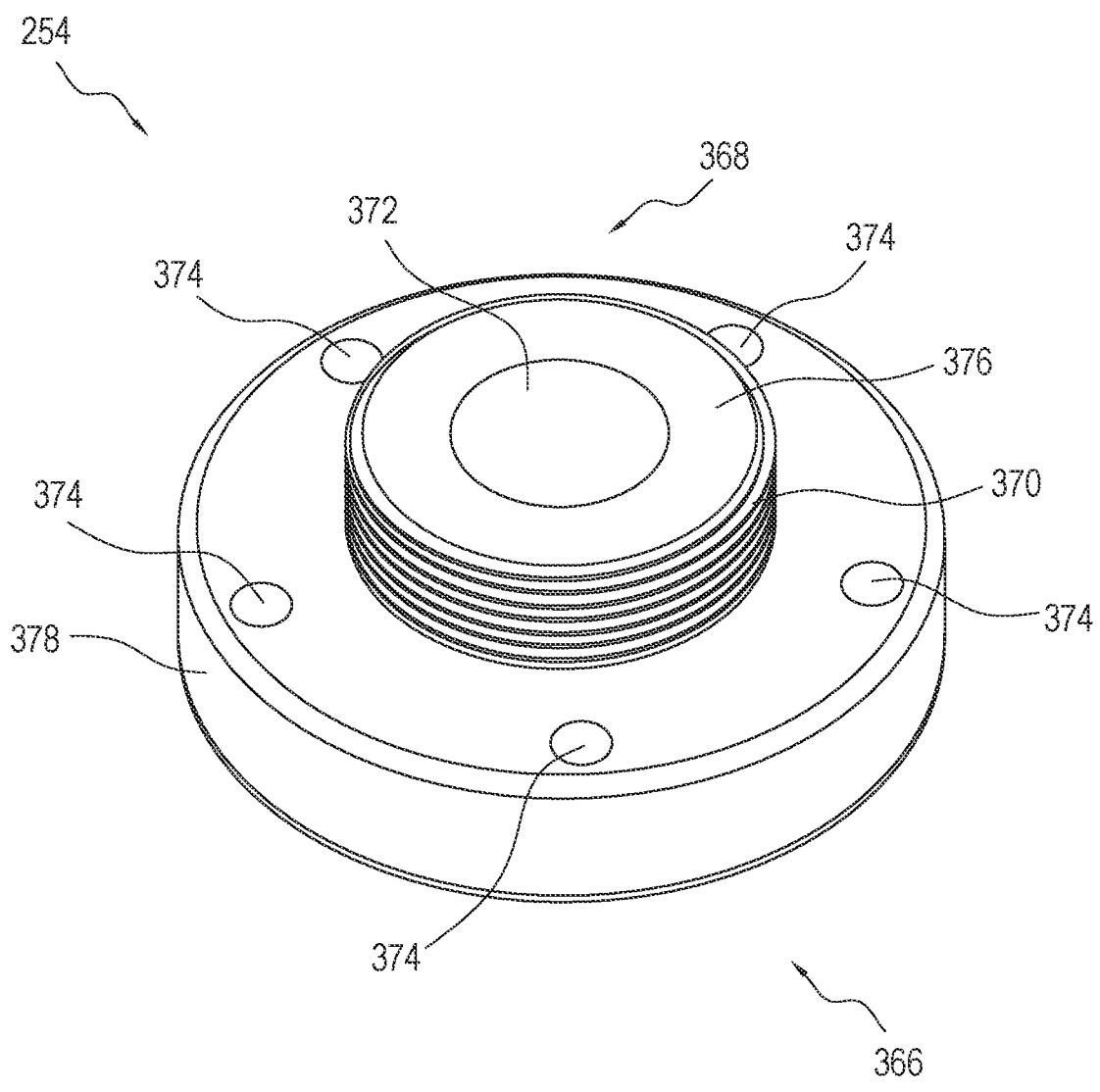
FIG. 30 is a perspective view of a base of the quick connect of FIG. 21.

Referring to FIG. 30, the base 254 of the collar assembly is engageable with the housing of the quick connect. The base has an inferior end 366 and a superior end 368. The base has a reduced diameter portion 376 about its superior end and a larger diameter portion 378 about its inferior end. The reduced diameter portion has external threads 370 and a central through hole 372. The external threads are engageable with the internal threads of the housing (FIG. 23E). The central through hole is configured and sized to receive the shaft of the connection adapter therethrough.

The larger diameter portion 378 of the base 254 has one or more through holes 374 laterally spaced from the central through hole 372. Although FIG. 30 illustrates the base having five through holes, the base can include 1, 2, 3, 4, 6, 7, 8, 9, 10, or any number of through holes suitable for containing a sufficient number of biasing devices so as to transmit the inferiorly directed force from the collar lock to the flange of the connection adapter. Referring to FIG. 23D, the through holes are counterbored to have a larger diameter portion 380 and a smaller diameter portion 382. The larger diameter portion is adapted to receive a pin or shaft 384 along with a biasing member 386 circumscribing the pin. The smaller diameter portion is adapted to receive a pin or shaft of the biasing device and sized to prevent the pin from falling out of the inferior end 366 of the base.

Figure 31:
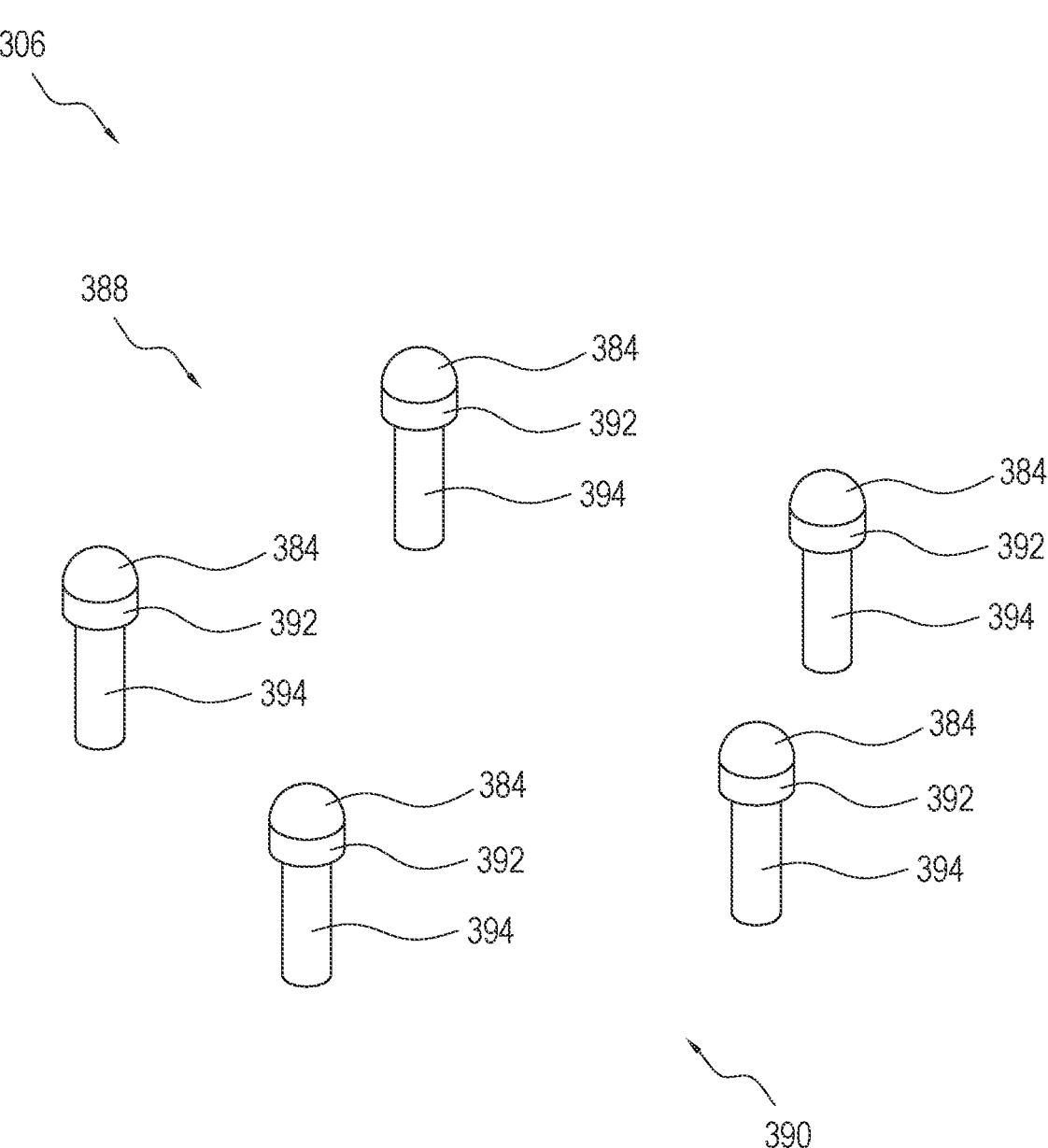
FIG. 31 is a perspective view of a biasing member of the quick connect of FIG. 21.

Referring to FIGS. 23D and 31, the biasing device includes a shaft or pin 384 that extends proud from a superior facing surface of the base, and a biasing member 386. Referring back to FIG. 36, each pin has a superior end

388 and an inferior end 390. Each pin has a head portion 392 about its superior end and a body portion 394 about its inferior end. The head portion is a larger diameter portion and the body portion is a smaller diameter portion. The head portion can have a generally rounded or hemispherical superior facing surface so as to reduce friction with the collar lock.

Referring to FIG. 23D, the biasing device 306 further includes a biasing member 386 circumscribing each pin 384. The biasing member circumscribes the body portion of the pin and abuts an inferior facing surface of the head portion of the pin. Each biasing member biases the head portion of the corresponding pin in the superior direction relative to the base so as to urge the pin into abutment with the inferior facing surface 302 of the collar lock.

Operation

Operation of the quick connect 10 can be broken down into four operational states: a first stage, a second stage, a third stage, and a fourth stage. Example states can include, but are not limited to, the first stage corresponding to an initial locked state (FIGS. 4A-4D), the second stage corresponding to an engaged state (FIGS. 6A-6B), the third stage corresponding to a disengaged state (FIGS. 4A-4D), and the fourth stage corresponding to an unlocked state (FIGS. 7A-7B). FIGS. 5A-5D illustrate the quick connect in transition between the various states.

Locked State

In operation, the user can connect a secondary device, e.g., a C-frame 12, onto the superior end of the quick connect. The user inserts the connection adapter 14 into the quick connect until it engages and is locked by the slide lock. Referring to FIGS. 4A-4D, in the locked state the lock buttons 42 of the slide lock 22 are fully extended laterally outward and the arm 36 extending from the substantially annular member 38 is in the furthest counterclockwise position relative to the corresponding slot 34 of the housing when viewed from a superior perspective (e.g., a top plan perspective). In this position, the planar side walls 178 in the central through hole 176 of the sleeve 88 of the locking assembly (FIG. 17) engage with or are aligned with the cooperating planar wall segments 82 of the connection adapter 14 (FIG. 2). During insertion of the connection adapter, the frustoconical end 76 of the connection adapter interacts with the slide lock to engage the slide lock in the first position (e.g., the locked position) and emit a sound, such as a click, that indicates successful connection of the quick connect to the connection adapter. Referring to FIG. 4C, the sound is generated, for example, when the lock buttons 42 of the slide lock 22 move past the cylindrical base 78 of the connection adapter and subsequently engage the reduced diameter portion 80 of the connection adapter. After connecting the quick connect to the connection adapter, the user rotates the quick connect including the C-frame to a position suitable for performing a desired action, e.g., an extraction of the medical tool or surgical implant.

Engaged State

Figure 5C:
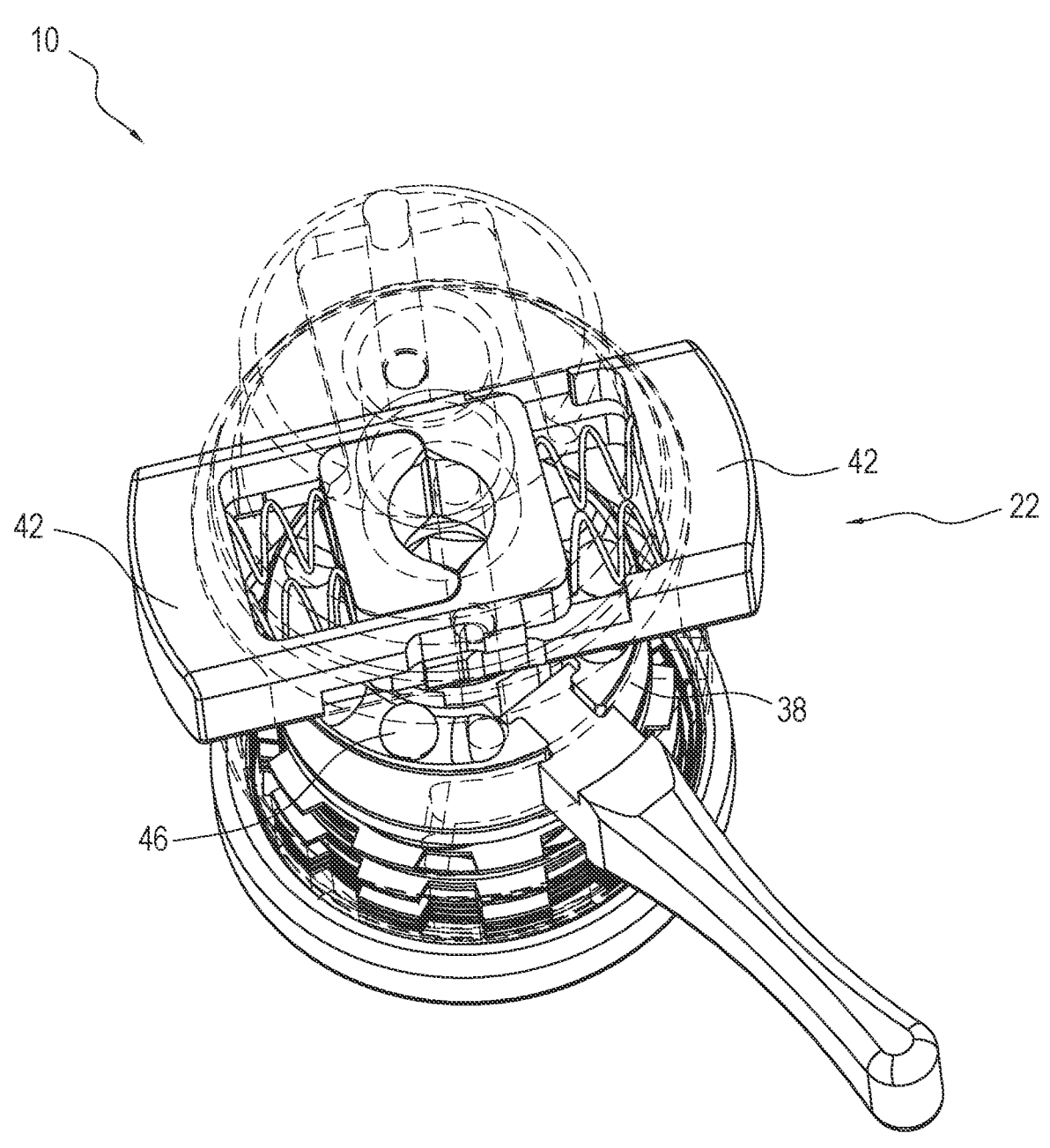
Figure 5D:
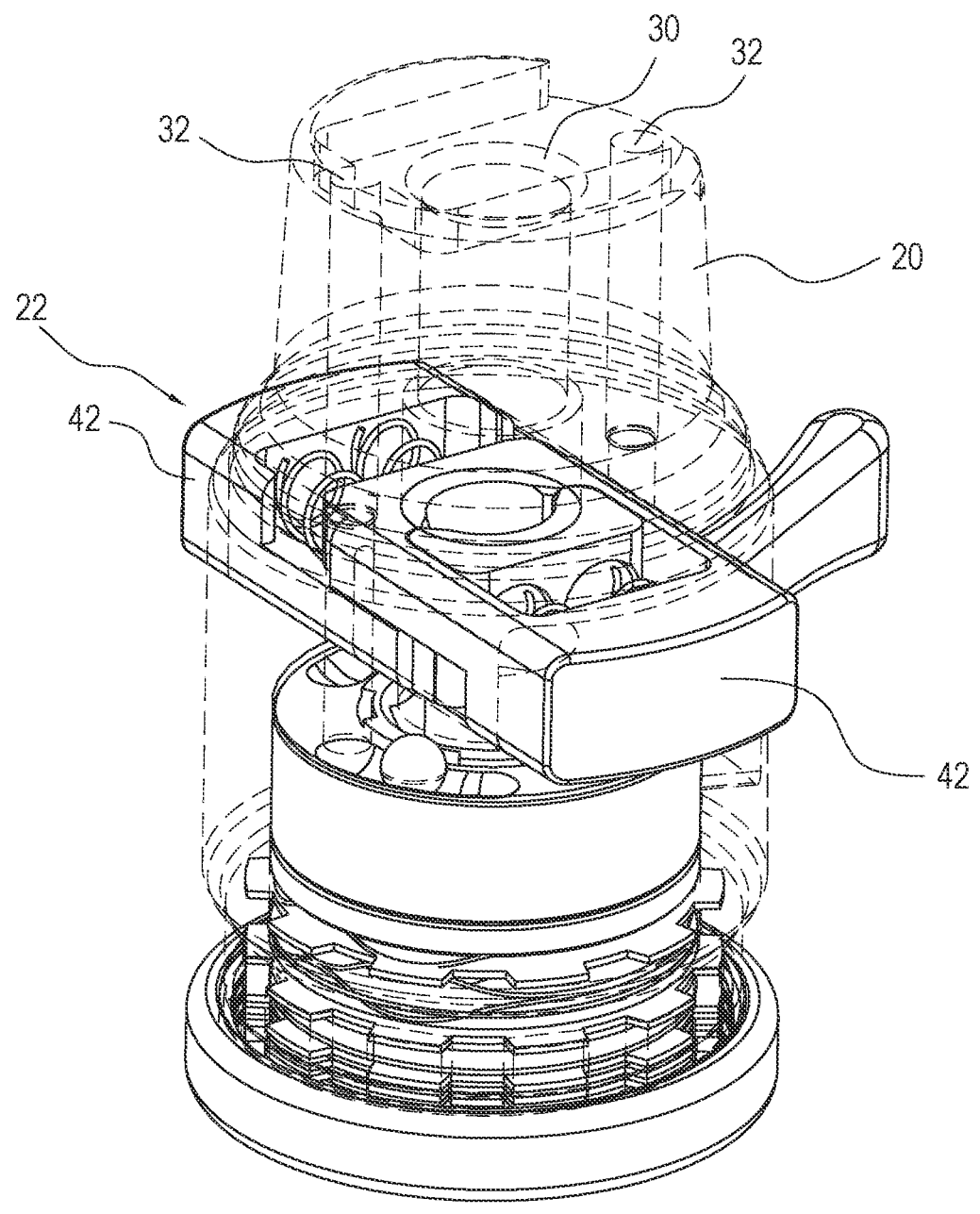

After the connection adapter has been inserted into the quick connect, the user rotates the arm extending from the substantially annular member in a clockwise direction (when viewed from its superior end) so as to fix the quick connect in place relative to the connection adapter. FIGS. 5A-5D show the quick connect in transition from the locked state to the engaged state. Rotating the arm about the longitudinal axis of the housing transmits torque from the arm rotation into linear movement of the locking assembly along the longitudinal axis of the housing. Referring to FIGS. 5B and 5C, as the substantially annular member rotates with the arm, the superiorly facing sloped recesses of the substantially annular member move relative to the balls that are fixedly mounted within the recesses in the inferior surface of the housing.

Figure 6A:
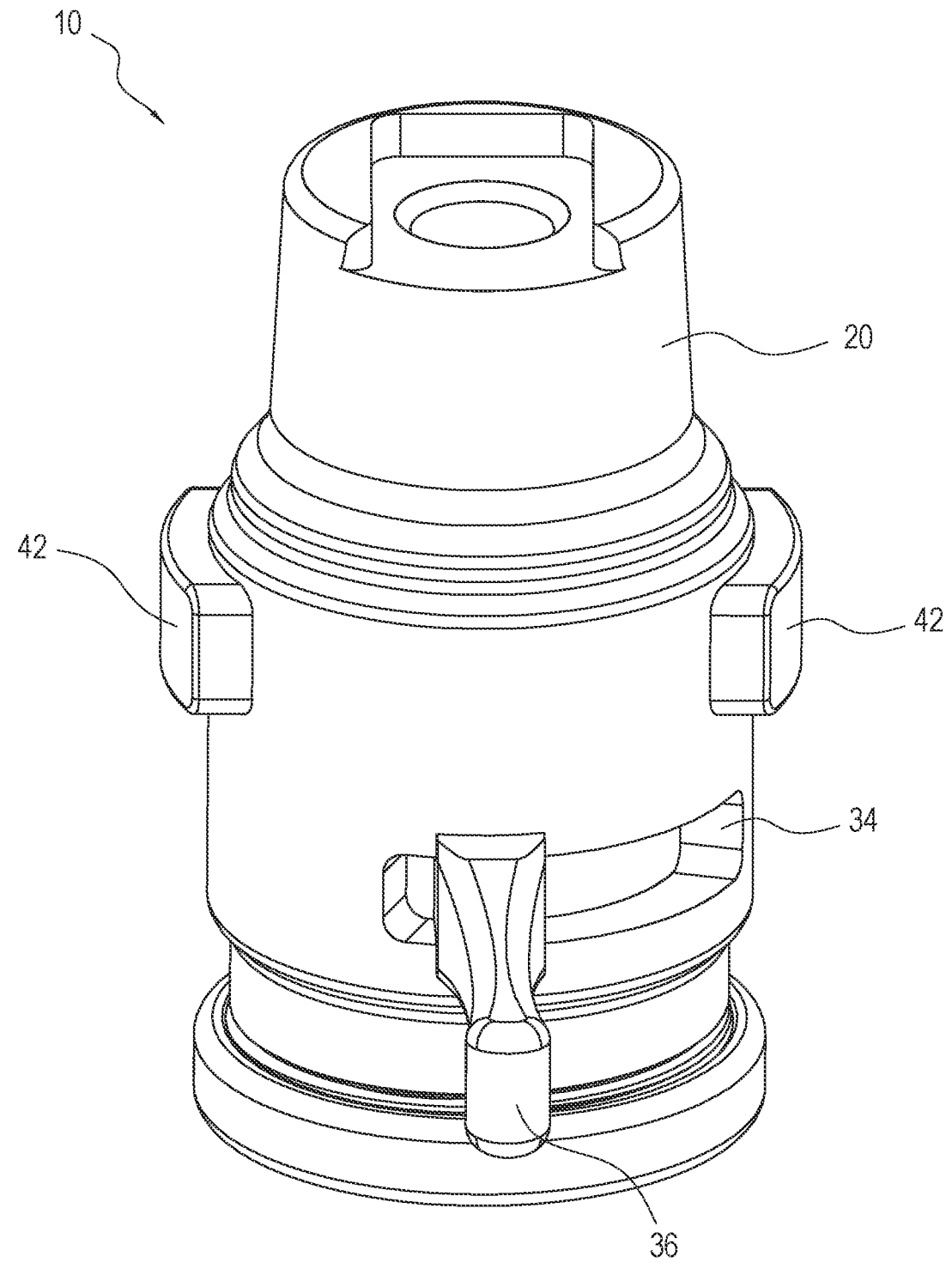
FIGS. 6A-6B are perspective views of the quick connect of FIG. 1A in an engaged state with certain components omitted and/or in phantom for purposes of illustration.
Figure 6B:
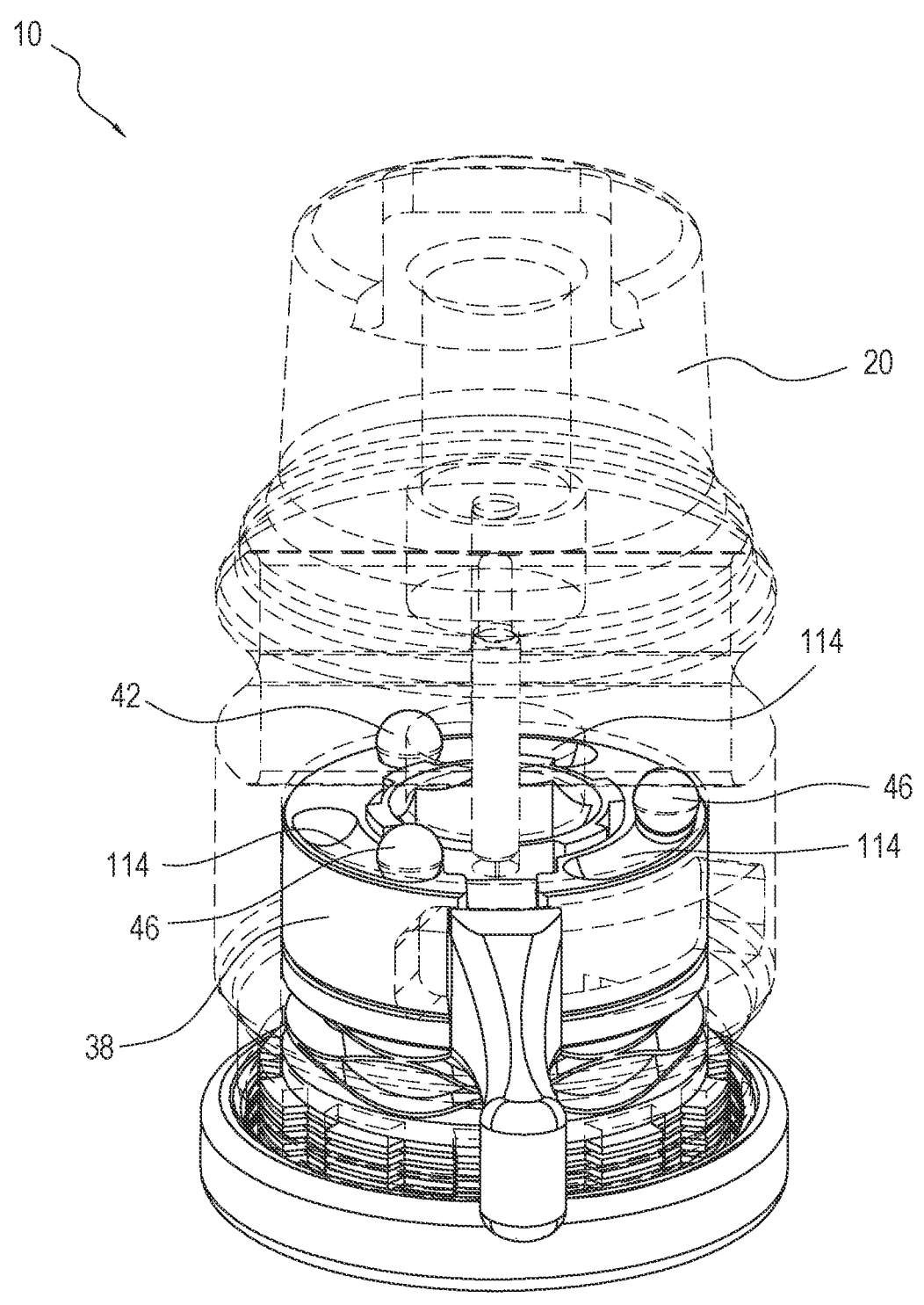
Figure 7A:
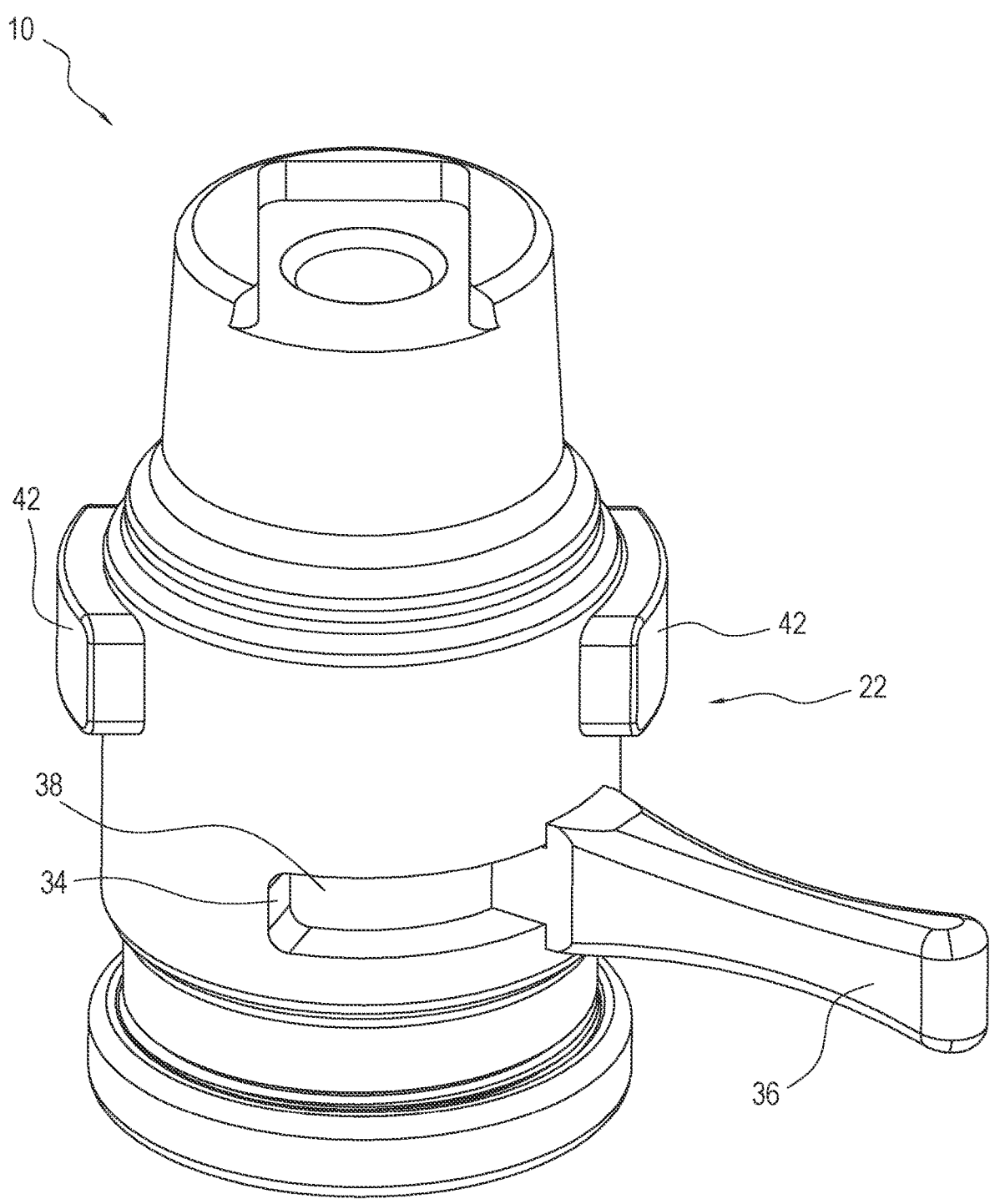
FIGS. 7A-7B are perspective views of the quick connect of FIG. 1A in an unlocked state with certain components omitted and/or in phantom for purposes of illustration.
Figure 7B:
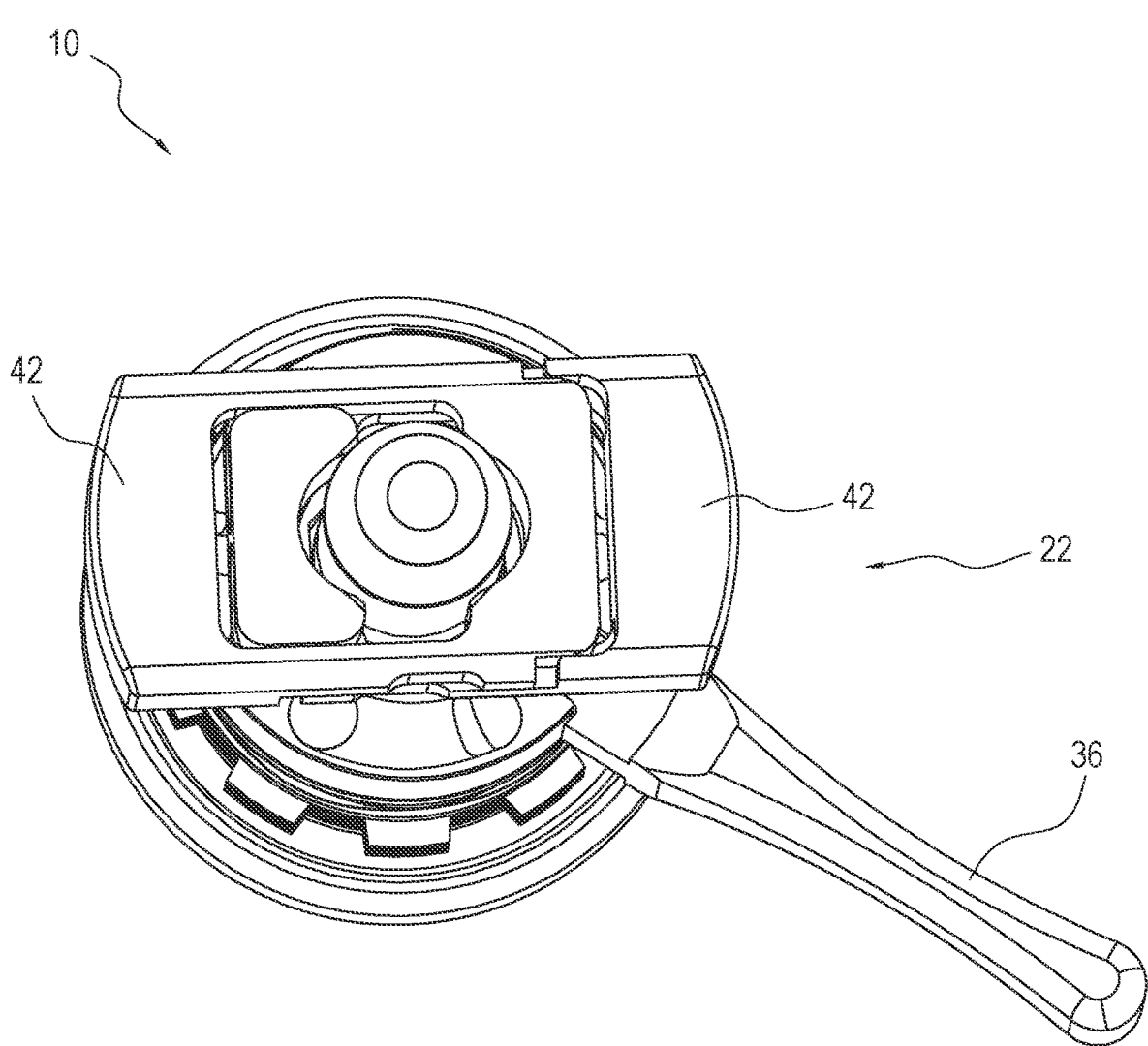

FIGS. 6A and 6B show the quick connect upon completion of the arm's clockwise rotation relative to the housing. In the engaged state the lock buttons 42 of the slide lock 22 are fully extended laterally outwardly with the arm 36 extending from the substantially annular member 38 in the furthest clockwise position (when viewed from a top plan perspective) relative to the corresponding slot 34 of the housing. When the arm completes its clockwise rotation (when viewed from a superior perspective), the shallow ends 114 of the recesses abut the balls, thereby moving the locking assembly in the inferior direction relative to the housing along its longitudinal axis and closer to the connection adapter.

As the substantially annular member moves inferiorly, the balls mounted in the inferior recesses of the substantially annular member exert an inferiorly directed force on the plates of the locking assembly, thereby moving the plates in the inferior direction. Referring to FIGS. 3B and 4B, the plate 90 of the locking assembly 24 that is disposed at the most inferior end 18 of the quick connect 10 moves inferiorly along the longitudinal axis A of the quick connect so as to engage the flange of the connection adapter. The interaction of the external splines of the plates 50 of the locking assembly with the internal splines at the inferior end of the housing operate to fix the position of the quick connect relative to the connection adapter without allowing undesired rotation once the arm extending from the substantially annular member is actuated. Similarly, the interaction of the internal splines of the plates 96, 98 with the external splines of the sleeve 88 of the locking assembly operate to fix the position of the quick connect relative to the connection adapter without allowing undesired rotation once the arm extending from the substantially annular member is actuated.

Disengaged State

Following a successful use of the medical device, the user is ready to disengage the housing of the quick connect from the connection adapter. The user rotates the arm extending from the substantially annular member counterclockwise (when viewed from a top plan view of the housing). FIGS. 5A-5D show the quick connect in transition from the engaged state to the disengaged state.

Referring to FIGS. 4A-4D, in the disengaged state the lock buttons 42 of the slide lock 22 are fully extended laterally outwardly with the arm 36 extending from the substantially annular member 38 in the furthest counterclockwise position relative to the corresponding slot 34 of the housing. Referring to FIG. 4D, when the arm 36 completes its counterclockwise rotation relative to the housing, the deep ends 112 of the superiorly facing sloped recesses abut the balls 46 mounted within the recesses in the inferior surface of the housing 20, thereby releasing the inferiorly directed force that was generated during the engaged state. Releasing the force allows the biasing member circumscribing the annular shim of the locking assembly to bias the annular shim and the substantially annular member in the superior direction. This operates to relieve the inferiorly directed force on the plates of the locking assembly.

Unlocked State

Referring to FIGS. 7A-7B, in the unlocked state the lock buttons 42 of the slide lock 22 are fully depressed laterally inwardly and the arm 36 extending from the substantially annular member is in the furthest counterclockwise position relative to the corresponding slot 34 of the housing. Referring to FIG. 7A, after rotating the arm extending from the substantially annular member counterclockwise, the user depresses the opposing lock buttons of the slide lock inwardly. Depressing the lock buttons operates to move the slide lock to the second position (e.g., the unlocked position) and thereby releases the quick connect from the connection adapter. When the slide lock transitions from the first to the second position, the lock buttons move relative to one another, enlarging the size of the central through hole of the slide lock in the second position so as to release the connection adapter and allow the connection adapter to be withdrawn from the quick connect.

Figure 24A:
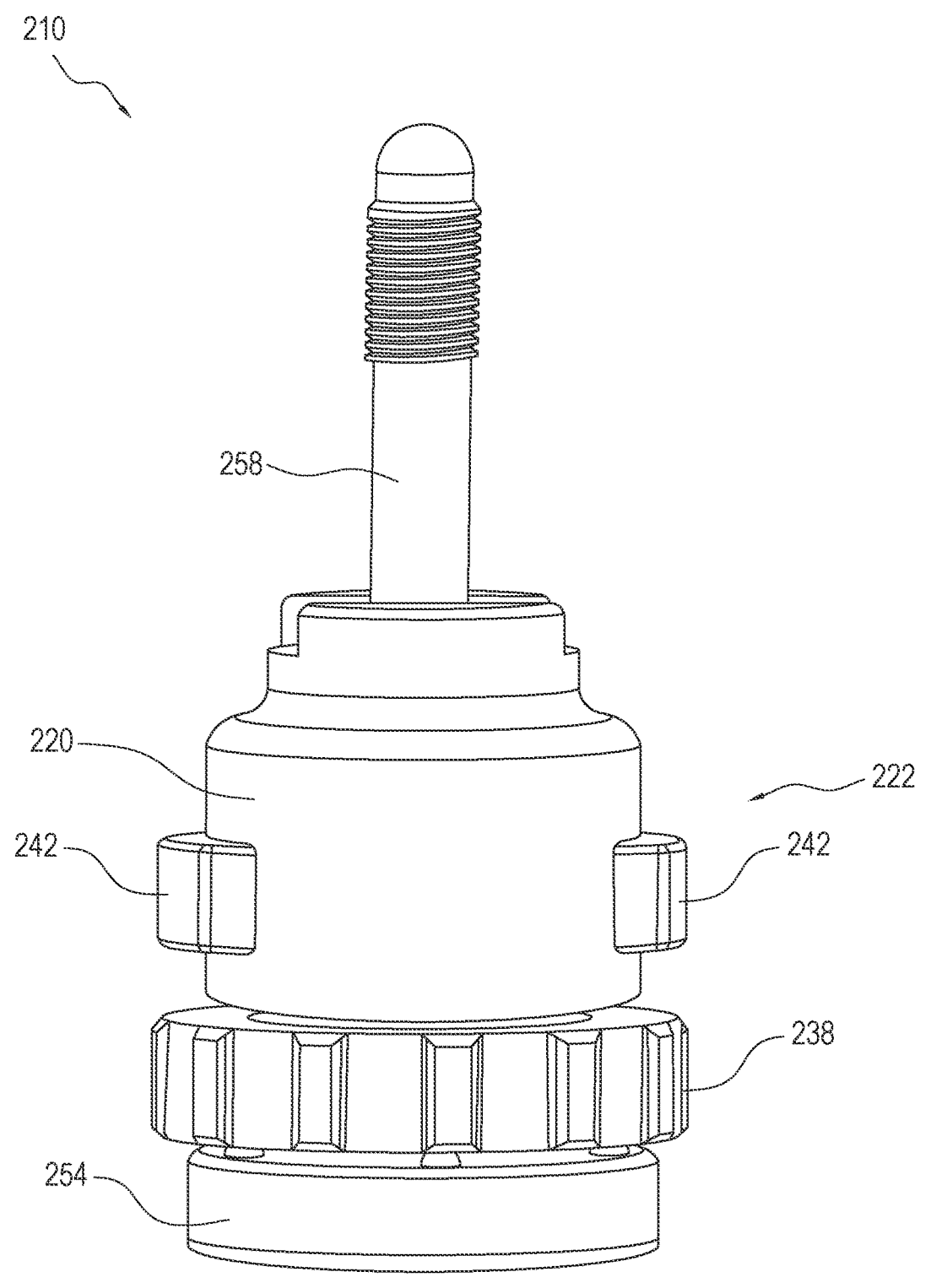
FIGS. 24A-24B are various views of the quick connect of FIG. 21 in transition to an engaged, disengaged, or unlocked state with certain components omitted and/or in phantom for purposes of illustration.
Figure 24B:

As with the quick connect 10, operation of the quick connect 210 can also be broken down into four operational states: a first stage, a second stage, a third stage, and a fourth stage. Example states can include, but are not limited to, the first stage corresponding to an initial locked state (FIGS. 23A-23E), the second stage corresponding to an engaged state (FIGS. 25A-25C), the third stage corresponding to a disengaged state (FIGS. 23A-23E), and the fourth stage corresponding to an unlocked state (FIGS. 26A-26C). FIGS. 24A-24B illustrate the quick connect in transition between the various states.

Locked State

Operation of the quick connect 210 begins with the user connecting a secondary device, e.g., a C-frame 212, onto the superior end of the quick connect. Specifically, the user connects the secondary device onto the shaft of the quick connect and tightens the nut 257 onto the superior end of the shaft. The user next inserts the connection adapter 214 into the quick connect until it engages and is locked by the slide locking mechanism 222. The shaft about the superior end of the connection adapter extends through the central through hole of the base of the collar assembly. Referring to FIGS. 23A-23E, in the locked state the lock buttons 242 of the slide locking mechanism are fully extended laterally outwardly and the collar lock is in the furthest superior position relative to the housing 220. During insertion of the connection adapter, the frustoconical end of the connection adapter interacts with the slide locking mechanism to move the slide locking mechanism into the locked position and emit a sound, such as a click, that indicates successful connection of the quick connect to the connection adapter. Referring to FIGS. 23C-23E, the sound is generated, for example, when the lock buttons of the slide locking mechanism move past the conical base of the connection adapter and subsequently engage the reduced diameter portion of the econnection adapter. After connecting the quick connect to the connection adapter, the user rotates the quick connect including the C-frame to a position suitable for performing a desired action, e.g., an extraction of the medical tool or surgical implant.

Engaged State

After the connection adapter has been inserted into the quick connect, the user rotates the collar lock of the collar assembly in a clockwise direction (when viewed from its superior end) so as to fix the quick connect in place relative to the connection adapter. FIGS. 24A-24B show the quick connect in transition from the locked state to the engaged state. Rotating the collar lock about the longitudinal axis of the housing transmits torque from the collar lock rotation into linear movement of the collar assembly along the longitudinal axis of the housing. As the collar lock 238 rotates, the biasing device of the base moves relative to the housing, thereby biasing the collar assembly in the inferior direction along the longitudinal axis of the housing and closer to the connection adapter.

Figure 25A:
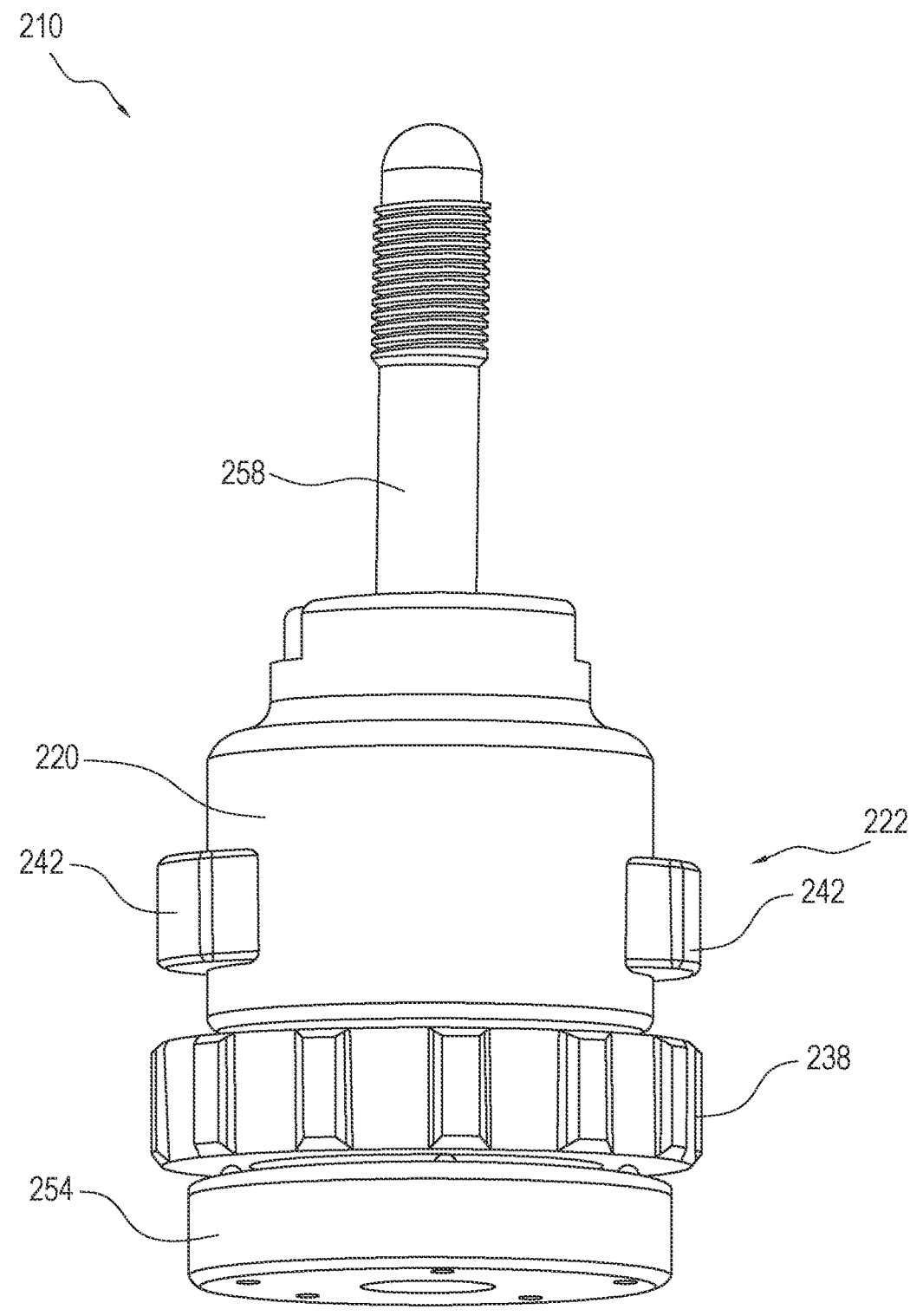
FIGS. 25A-25C are various views of the quick connect of FIG. 21 in an engaged state with certain components omitted and/or in phantom for purposes of illustration.
Figure 25B:
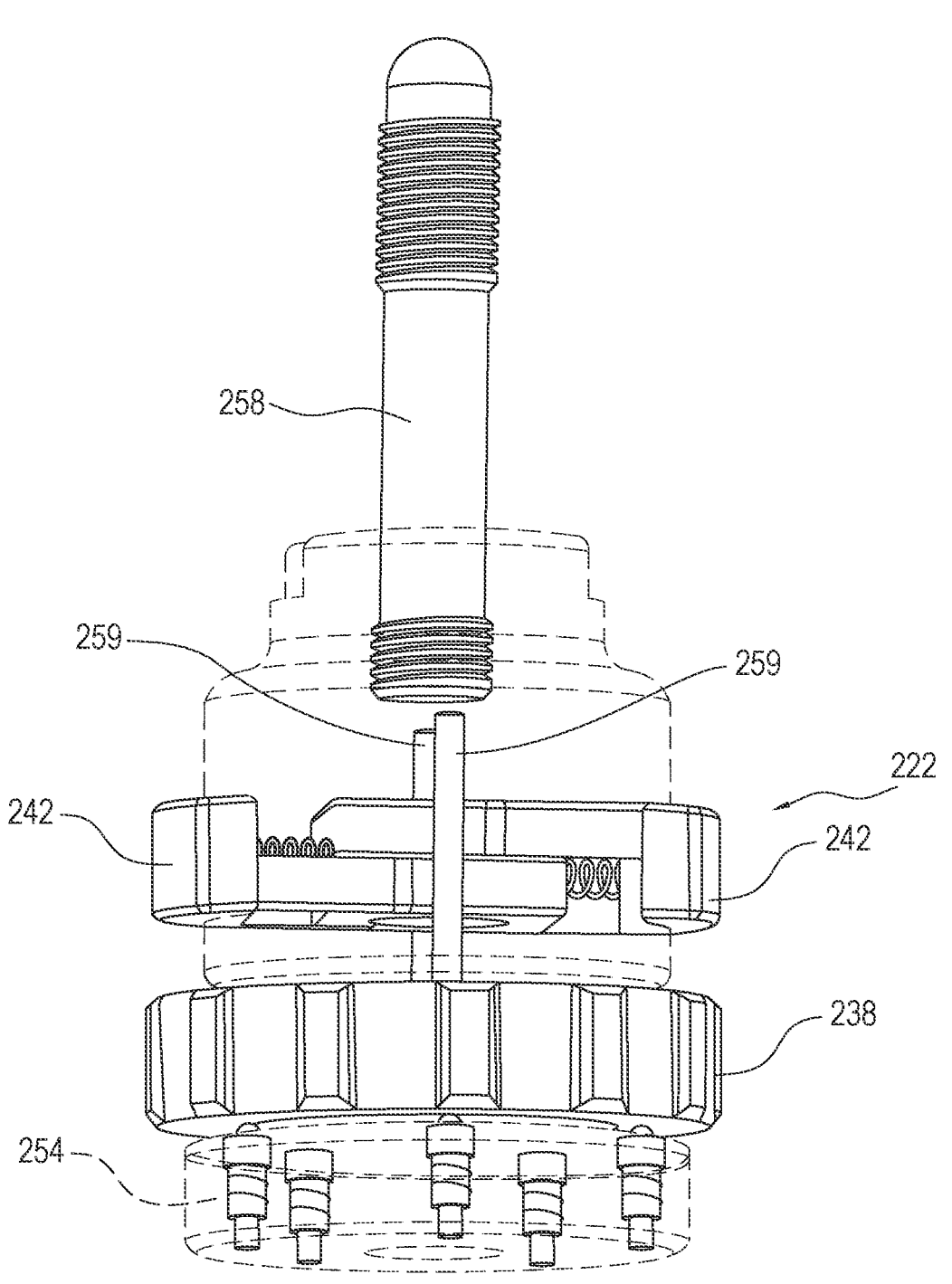
Figure 25C:
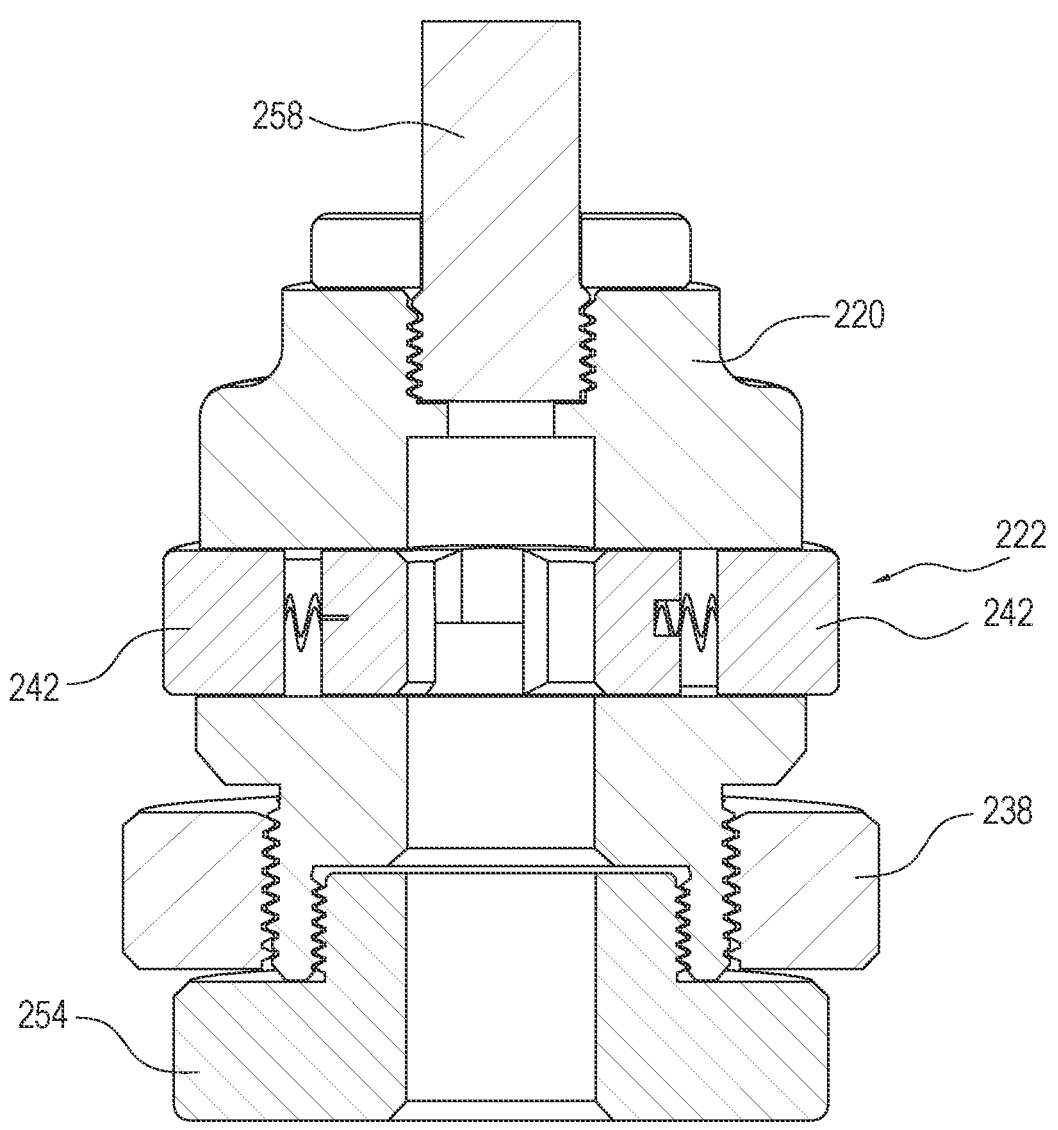
Figure 26A:
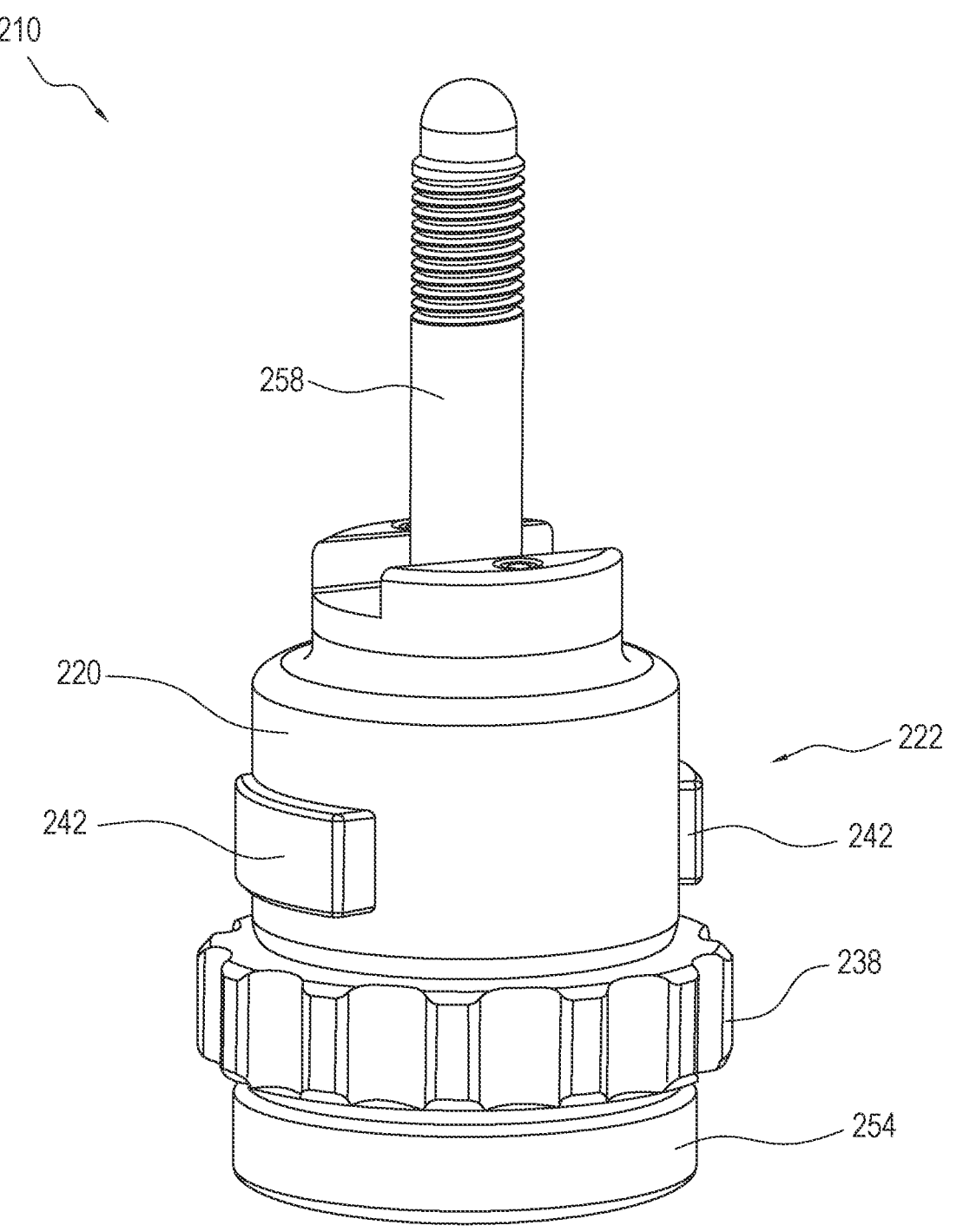
FIGS. 26A-26C are various views of the quick connect of FIG. 21 in an unlocked state with certain components omitted and/or in phantom for purposes of illustration.
Figure 26B:
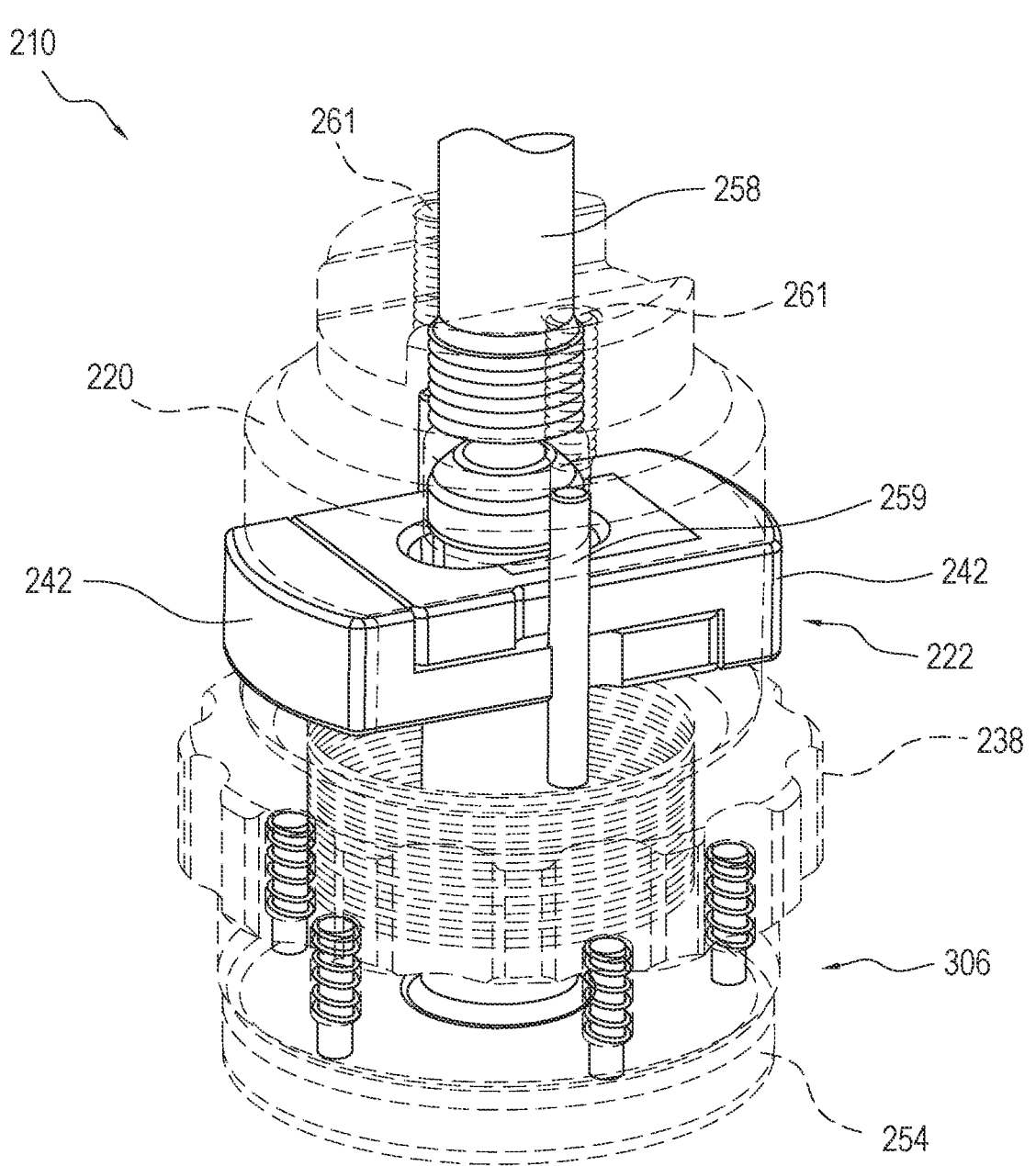
Figure 26C:
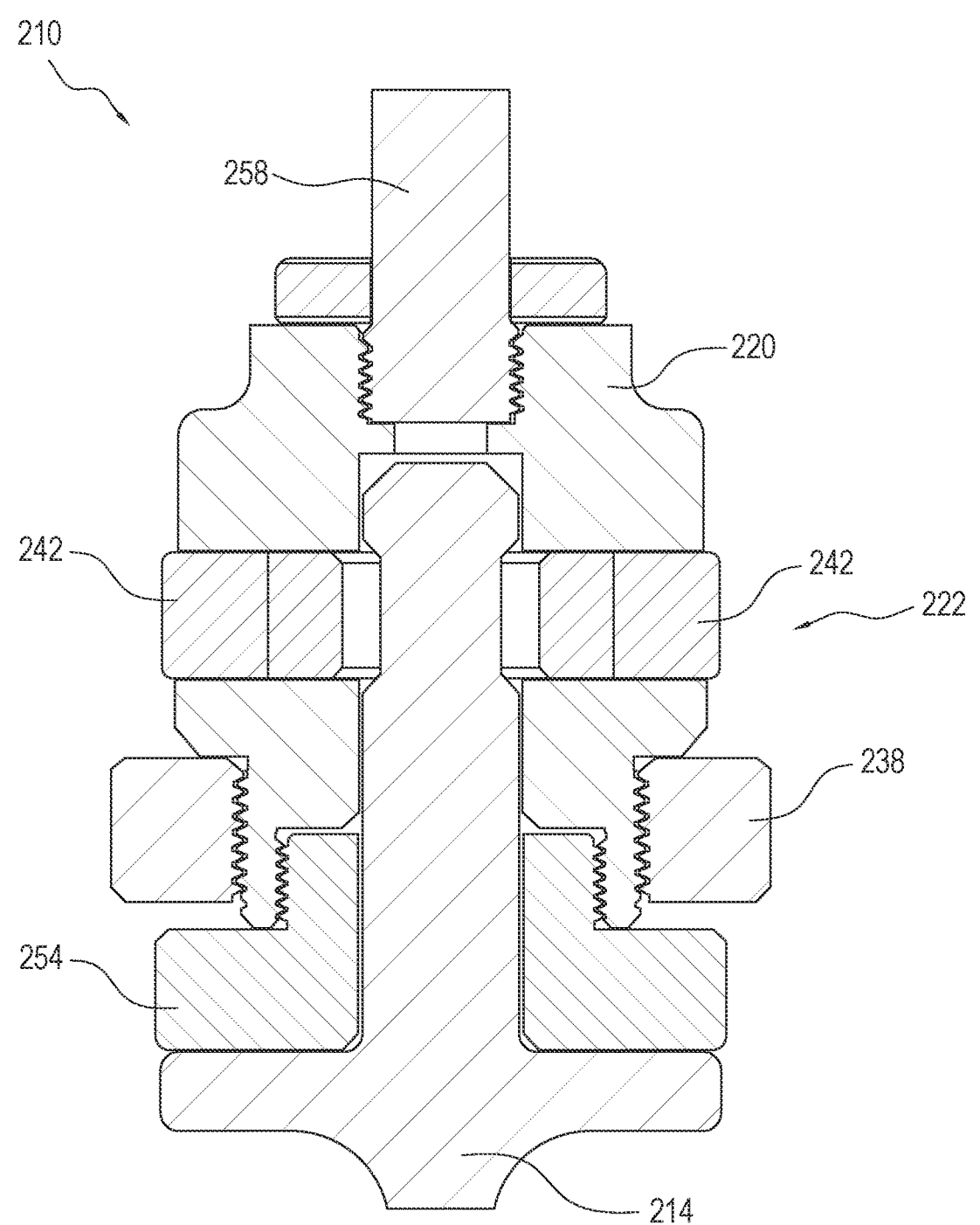

FIGS. 25A-25C show the quick connect upon completion of the collar lock's clockwise rotation relative to the housing. As the collar lock moves inferiorly, the collar lock exerts an inferiorly directed force on the head portions of the pins of the biasing device, thereby moving the pins in the inferior direction relative to the housing. The body portions of the pins move inferiorly and ultimately abut the flange about the superior end of the connection adapter. In the engaged state the lock buttons of the slide locking mechanism are fully extended laterally outwardly, and the collar lock of the collar assembly and the pins of the biasing member are in the furthest inferior position relative to the housing. The abutment of the pins at the inferior end of the base operates to reduce or eliminate undesired movement, or "play," relative to the flange of the connection adapter once the collar lock is rotated.

Disengaged State

Following a successful use of the medical device, the user is ready to release the housing of the quick connect from the connection adapter. The user rotates the collar lock counterclockwise (when viewed from a top plan view). FIGS. 24A-24B show the quick connect in transition from the engaged state to the disengaged state.

Referring to FIGS. 23A-23E, in the disengaged state the lock buttons of the slide locking mechanism are fully extended laterally outwardly and the collar lock of the collar assembly is in the furthest superior position relative to the housing. Referring to FIG. 23D, when the collar lock completes its counterclockwise rotation relative to the housing, the biasing members circumscribing each pin of the biasing device urge each pin in the superior direction, thereby releasing the inferiorly directed force on each pin and relieving the abutting engagement with the flange of the connection adapter.

Unlocked State

Referring to FIGS. 26A-26C, in the unlocked state the lock buttons 242 of the slide locking mechanism 222 are fully depressed laterally inwardly and the collar lock 238 of the collar assembly is in the furthest superior position relative to the housing. After rotating the collar lock of the collar assembly counterclockwise, the user depresses the opposing lock buttons of the slide locking mechanism inwardly. Depressing the lock buttons operates to move the slide locking mechanism to the unlocked position and thereby releases the quick connect from the connection adapter. When the slide lock is transitioning from the locked to the unlocked position, the lock buttons move relative to one another. Referring to FIGS. 26B and 26C, in the unlocked position the interaction of the lock buttons thereby enlarges the size of the central through hole of the slide locking mechanism so as to release the connection adapter and allow the connection adapter to be withdrawn from the quick connect.

The various exemplary embodiments of the quick connect discussed herein provide numerous advantages over conventional quick connects. For example, the present quick connect provides a slide lock and a locking assembly. The slide lock and locking assembly are adapted to reduce or eliminate undesired movement and rotation (e.g., "play") relative to a cooperating connection adapter.

Another advantage of the exemplary quick connect embodiments is the inclusion of a substantially annular member, in the locking assembly. The substantially annular member is adapted to transmit torque from rotation of the annular member into linear movement of the locking assembly along the longitudinal axis of the quick connect and reduce or eliminate undesired movement and rotation relative to the cooperating connection adapter.

An additional advantage of the exemplary quick connect embodiments is the inclusion of one or more plates in the locking assembly, e.g., plates 50, 90, 92, 94, 96, 98. The plates are splined so as to engage with cooperating splines on a sleeve and a housing of the quick connect and thereby reduce undesired rotation and play relative to the cooperating connection adapter.

Furthermore, an advantage of the exemplary quick connect embodiments is the inclusion of a slide locking mechanism and a collar assembly, e.g., slide locking mechanism 222 and collar assembly 224. The slide locking mechanism and collar assembly are adapted to reduce undesired movement (e.g., "play") relative to a cooperating connection adapter.

A still further advantage of the exemplary quick connect embodiments is the inclusion of one or more pins in a biasing device of the collar assembly. The pins and biasing device are adapted to transmit torque from rotation of the collar lock into linear movement of the pins along the longitudinal axis of the quick connect and reduce undesired movement relative to the cooperating connection adapter.

It will be appreciated by those skilled in the art that changes could be made to the exemplary embodiments described above without departing from the broad inventive concept thereof. It is to be understood, therefore, that this disclosure is not limited to the particular embodiments disclosed, but it is intended to cover modifications within the spirit and scope of the subject disclosure as defined by the appended claims.

We claim:

1. A quick connect for a medical device comprising:
a housing having a proximal end and a distal end;
a slide lock including a depressible lock button mounted within the housing for receiving a cooperating connection adapter; and
a locking assembly mounted within the housing, the locking assembly including a substantially annular member having a proximally facing end surface substantially perpendicular to a longitudinal axis of the annular member, the proximally facing end surface comprising at least one sloped recess therein, wherein the substantially annular member is movable along a longitudinal axis of the housing upon rotation of the substantially annular member.

2. The quick connect of claim 1, wherein the locking assembly further comprises a ball mounted within the at least one sloped recess.

3. The quick connect of claim 1, wherein the locking assembly further comprises a plurality of plates movable along the longitudinal axis of the housing upon movement of the substantially annular member, wherein one of the plurality of plates extends beyond the distal end of the housing.

4. The quick connect of claim 1, wherein the locking assembly further comprises a plate movable along the longitudinal axis of the housing upon movement of the substantially annular member.

5. The quick connect of claim 4, wherein the plate extends beyond the distal end of the housing.

6. The quick connect of claim 1, wherein the housing includes a recess for receiving a ball.

7. The quick connect of claim 1, wherein the substantially annular member includes a recess about a distal end thereof for receiving a ball.

8. The quick connect of claim 1, wherein the locking assembly further comprises a sleeve circumscribed by the housing and including a plurality of splines, or wherein the locking assembly further comprises a biasing member biasing the substantially annular member.

9. The quick connect of claim 1, wherein the slide lock extends between opposing lateral sides of the housing, or wherein the slide lock further comprises a biasing member for biasing a first clamping portion and a second clamping portion.

10. The quick connect of claim 1, wherein the slide lock comprises:

a first clamping portion; and a second clamping portion moveable relative to the first clamping portion.

11. The quick connect of claim 1, wherein the cooperating connection adapter releasably connects with the slide lock.

12. A quick connect for a medical device comprising:

a housing having a proximal end and a distal end;

a slide lock including a depressible lock button mounted within the housing for receiving a cooperating connection adapter; and a locking assembly mounted within the housing, the locking assembly including a substantially annular member having a proximal end comprising a proximally facing sloped recess, wherein:

the substantially annular member is movable along a longitudinal axis of the housing upon rotation of the substantially annular member; and the locking assembly further comprises a plurality of plates movable along the longitudinal axis of the housing upon movement of the substantially annular member, where one of the plurality of plates extends beyond the distal end of the housing.

13. The quick connect of claim 12, wherein the locking assembly further comprises a ball mounted within the proximally facing sloped recess.

14. The quick connect of claim 12, wherein the housing includes a recess for receiving a ball.

15. The quick connect of claim 12, wherein the locking assembly further comprises a sleeve circumscribed by the housing and including a plurality of splines, or wherein the locking assembly further comprises a biasing member biasing the substantially annular member.

16. The quick connect of claim 12, wherein the slide lock extends between opposing lateral sides of the housing, or wherein the slide lock further comprises a biasing member for biasing a first clamping portion and a second clamping portion.

17. The quick connect of claim 12, wherein the slide lock comprises:

a first clamping portion; and a second clamping portion moveable relative to the first clamping portion.

18. A quick connect for a medical device comprising:

a housing having a proximal end and a distal end;

a slide lock including a depressible lock button mounted within the housing for receiving a cooperating connection adapter; and a locking assembly mounted within the housing, the locking assembly including a substantially annular member having a proximal end comprising a proximally facing sloped recess, wherein:

the substantially annular member is movable along a longitudinal axis of the housing upon rotation of the substantially annular member; and the substantially annular member includes a recess about a distal end thereof for receiving a ball.

19. The quick connect of claim 18, wherein the locking assembly further comprises a ball mounted within the proximally facing sloped recess.

20. The quick connect of claim 18, wherein the locking assembly further comprises a plurality of plates movable along the longitudinal axis of the housing upon movement of the substantially annular member, wherein one of the plurality of plates extends beyond the distal end of the housing.

*    *    *    *    *